US009278963B2

(12) United States Patent
van Duzer et al.

(10) Patent No.: US 9,278,963 B2
(45) Date of Patent: Mar. 8, 2016

(54) PYRIMIDINE HYDROXY AMIDE COMPOUNDS AS HISTONE DEACETYLASE INHIBITORS

(71) Applicant: Acetylon Pharmaceuticals, Inc., Boston, MA (US)

(72) Inventors: John H. van Duzer, Georgetown, MA (US); Ralph Mazitschek, Belmont, MA (US); Simon Stewart Jones, Harvard, MA (US); Min Yang, Newton, MA (US); David Lee Tamang, Watertown, MA (US)

(73) Assignee: Acetylon Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 14/510,711

(22) Filed: Oct. 9, 2014

(65) Prior Publication Data

US 2015/0105384 A1 Apr. 16, 2015

Related U.S. Application Data

(60) Provisional application No. 61/889,295, filed on Oct. 10, 2013, provisional application No. 61/944,754, filed on Feb. 26, 2014, provisional application No. 61/979,694, filed on Apr. 15, 2014.

(51) Int. Cl.
*A61K 31/506* (2006.01)
*C07D 417/12* (2006.01)
*C07D 401/12* (2006.01)
*C07D 401/14* (2006.01)
*C07D 239/42* (2006.01)

(52) U.S. Cl.
CPC ............ *C07D 417/12* (2013.01); *C07D 239/42* (2013.01); *C07D 401/12* (2013.01); *C07D 401/14* (2013.01); *A61K 31/506* (2013.01)

(58) Field of Classification Search
CPC .............................. C07D 401/12; A61K 31/506
See application file for complete search history.

(56) References Cited

U.S. PATENT DOCUMENTS

| | | | |
|---|---|---|---|
| 3,549,633 A | 12/1970 | Grabowski et al. | |
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,501,417 B2* | 3/2009 | Van Emelen | C07D 207/09 514/252.14 |
| 7,541,369 B2* | 6/2009 | Angibaud | C07D 207/09 514/316 |
| 7,868,205 B2* | 1/2011 | Moradei | C07C 233/25 544/295 |
| 7,994,362 B2 | 8/2011 | Schreiber et al. | |
| 8,148,526 B1 | 4/2012 | van Duzer et al. | |
| 8,394,810 B2 | 3/2013 | van Duzer et al. | |
| 8,524,711 B2* | 9/2013 | Angibaud | C07D 207/09 514/235.8 |
| 8,609,678 B2 | 12/2013 | van Duzer et al. | |
| 8,614,223 B2* | 12/2013 | van Duzer | 514/275 |
| 9,096,549 B2* | 8/2015 | van Duzer | C07D 235/06 |
| 9,139,583 B2* | 9/2015 | van Duzer | C07D 471/04 |
| 9,145,412 B2* | 9/2015 | van Duzer | C07D 471/04 |
| 9,150,560 B2* | 10/2015 | Van Emelen | C07D 413/12 |
| 2004/0266769 A1 | 12/2004 | Bressi et al. | |
| 2005/0096468 A1* | 5/2005 | Van Emelen | C07D 207/09 544/238 |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2008/0039509 A1 | 2/2008 | Lu et al. | |
| 2008/0207590 A1 | 8/2008 | Deziel et al. | |
| 2009/0023786 A1 | 1/2009 | Miller et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |
| 2010/0152254 A1 | 6/2010 | Bialer et al. | |
| 2010/0168463 A1 | 7/2010 | Hirata et al. | |
| 2010/0317678 A1 | 12/2010 | Moffat et al. | |
| 2011/0218154 A1 | 9/2011 | Schreiber et al. | |
| 2011/0300134 A1* | 12/2011 | van Duzer | C07C 259/06 424/133.1 |
| 2012/0121502 A1* | 5/2012 | van Duzer | C07D 239/42 424/1.11 |
| 2013/0225543 A1* | 8/2013 | Jones | A61K 31/165 514/171 |
| 2014/0011767 A1 | 1/2014 | Yang et al. | |
| 2014/0142104 A1* | 5/2014 | van Duzer | C07D 239/42 514/235.8 |
| 2014/0142117 A1 | 5/2014 | van Duzer et al. | |
| 2014/0243345 A1 | 8/2014 | van Duzer et al. | |

(Continued)

FOREIGN PATENT DOCUMENTS

EP 2 524 918 A1 11/2012
WO 03/037869 A1 5/2003

(Continued)

OTHER PUBLICATIONS

T. Abel et al., Current Opinion in Pharmacology, 57-64 (2008).*

(Continued)

*Primary Examiner* — Alexander R Pagano
(74) *Attorney, Agent, or Firm* — Lathrop & Gage LLP; Brian C. Trinque

(57) ABSTRACT

Provided herein are compounds, pharmaceutical compositions comprising such compounds, and methods of using such compounds to treat or prevent diseases or disorders associated with HDAC activity, particularly diseases or disorders that involve activity of HDAC1, HDAC2, and/or HDAC6. Also provided herein are methods for inhibiting migration of a neuroblastoma cell, inducing maturation of a neuroblastoma cell, and altering cell cycle progression of a neuroblastoma cell comprising administering to the cell a therapeutically effective amount of a HDAC1, HDAC2, and/or HDAC6 selective inhibitor or a pharmaceutically acceptable salt thereof.

24 Claims, 34 Drawing Sheets

(56) References Cited

U.S. PATENT DOCUMENTS

| | | | |
|---|---|---|---|
| 2014/0249148 A1 | 9/2014 | van Duzer et al. | |
| 2014/0357512 A1* | 12/2014 | Yang | G01N 33/57407 506/9 |
| 2015/0045380 A1 | 2/2015 | van Duzer et al. | |
| 2015/0099744 A1* | 4/2015 | Tamang | C07D 239/42 514/234.2 |
| 2015/0105358 A1* | 4/2015 | Quayle | A61K 31/505 514/171 |
| 2015/0105383 A1* | 4/2015 | Quayle | C07D 239/42 514/234.2 |
| 2015/0105384 A1 | 4/2015 | Jones et al. | |
| 2015/0105409 A1* | 4/2015 | Quayle | C07D 239/42 514/262.1 |
| 2015/0150871 A1* | 6/2015 | Quayle | A61K 31/4439 424/278.1 |
| 2015/0176076 A1* | 6/2015 | Yang | A61K 31/505 514/275 |

FOREIGN PATENT DOCUMENTS

| | | | |
|---|---|---|---|
| WO | 03/076401 A1 | 9/2003 | |
| WO | 03/076430 A1 | 9/2003 | |
| WO | WO 03076430 A1 * | 9/2003 | C07D 207/09 |
| WO | 03/087057 A1 | 10/2003 | |
| WO | 2004/052869 A1 | 6/2004 | |
| WO | 2005/012261 A1 | 2/2005 | |
| WO | 2005/028447 A1 | 3/2005 | |
| WO | 2005/030705 A1 | 4/2005 | |
| WO | 2006/102557 A2 | 9/2006 | |
| WO | 2006/123121 A1 | 11/2006 | |
| WO | 2007/022638 A1 | 3/2007 | |
| WO | 2007/091703 A2 | 8/2007 | |
| WO | 2007/130429 A2 | 11/2007 | |
| WO | 2008/055068 A2 | 5/2008 | |
| WO | 2008/091349 A1 | 7/2008 | |
| WO | 2009/137462 A1 | 11/2009 | |
| WO | 2009/137503 A1 | 11/2009 | |
| WO | 2010/009155 A2 | 1/2010 | |
| WO | 2010/011296 A2 | 1/2010 | |
| WO | 2010/080996 A1 | 7/2010 | |
| WO | 2011/011186 A1 | 1/2011 | |
| WO | 2011/019393 A2 | 2/2011 | |
| WO | 2011/084991 A2 | 7/2011 | |
| WO | WO 2011091213 A2 * | 7/2011 | C07C 259/06 |
| WO | 2012/098132 A1 | 7/2012 | |

OTHER PUBLICATIONS

R.M Stilling et al., 96 Neurobiology of Learning and Memory, 19-26 (2011).*
Y.N. Sung et al., 239 Experimental Neurology, 192-201 (2013).*
D-M Chuang et al., 32 Trends in Neurosciences, 591-601 (2009).*
A. Fischer et al., 31 Trends in Neurosciences, 591-601 (2010).*
O. Witt et al., 277 Cancer Letters, 8-21 (2009).*
W. Weichert et al., 280 Cancer Letters, 168-176 (2009).*
V.M. Richon et al., 280 Cancer Letters, 201-210 (2009).*
P. Bertrand, 45 European Journal of Medicinal Chemistry, 2095-2116 (2010).*
S. Ropero et al., 1 Molecular Oncology, 19-25 (2007).*
Angibaud et al. (2005) "Discovery of Pyrimidyl-5-hydroxamic acids as New Potent Histone Deacetylase Inhibitors," European Journal of Medicinal Chemistry. 40(6):597-606.
Brana et al. (2002) "Synthesis and biological evaluation of novel 2-(1H-imidazol-4-yl)cyclopropane carboxylic acids: key intermediates for H3 histamine receptor ligands," BioOrganic & Medicinal Chemistry Letter. 12(24):3561-3563.
Broxterman et al. (1992) "Synthesis of (optically active) sulfur-containing trifunctional amino acids by radical addition to (optically active) unsaturated amino acids," The Journal of Organic Chemistry. 57(23):6286-6294.
Butler et al. (2000) "Suberoylanilide Hydroxamic Acid, an Inhibitor of Histone Deacetylase, Suppresses the Growth of Prostate Cancer Cells in Vitro and in Vivo," Cancer Research. 60:5165-5170.
Carey et al. (2006) "Histone deacetylase inhibitors: gathering pace," Current Opinion in Pharmacology. 6:369-375.
Chuang et al. (2009) "Multiple roles of Hdac inhibition in neurodegenerative conditions," Trends in Neurosciences. 32 (11):591-601.
Dallavalle et al. (2012) "Development and therapeutic impact of HDAC6-selective inhibitors," Biochemical Pharmacology. 84:756-765.
Elaut et al. (2007) "The Pharmaceutical Potential of Histone Deacetylase Inhibitors," Current Pharmaceutical Design. 13:2584-2620.
Foks et al. (1972) "Investigations on Pyrazine Derivatives Part II. Synthesis and Tuberculostatic Action of Some 6 Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Lane et al. (2009) "Histone deacetylase inhibitors in cancer therapy," J. Clin. Oncol. 27:5459-5468.
Neidle, Stephen: Ed. (2008) Cancer Drug Design and Discovery. Elsevier/Academic Press. pp. 427-431.
Pellicciari et al. (1996) "Synthesis and Pharmacological Characterization of All Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist," Journal of Medicinal Chemistry. 39(11):2259-2269.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Walbrick et al.(1968) "A general method for synthesizing optically active 1,3-disubstituted allene hydrocarbons," The Journal of the American Chemical Society. 90(11):2895-2901.
Warner et al. (1992) "Electron demand in the transition state of the cyclopropylidene to allene ring opening," The Journal of Organic Chemistry. 57(23):6294-6300.
International Preliminary Report on Patentability corresponding to International Patent Application No. PCT/US2011/060791, dated Jul. 22, 2014.
International Search Report corresponding to International Patent Application No. PCT/US2011/021982, Oct. 12, 2011.
International Search Report with Written Opinion corresponding to International Patent Application No. PCT/US2011/060791, mailed Mar. 5, 2014.
Supplementary European Search Report corresponding to European Application No. 11840803.8, dated Mar. 5, 2014.
Alfonso R. Gennaro: Ed. (1970) Remington's Pharmaceutical Science. 17th Ed. Mack Publishing Co. Easton, Pennsylvania. p. 1418.
Berge et al. (1977) "Pharmaceutical salts," Journal of Pharmaceutical Sciences. 66:1-19.
Bradner (Jan. 28, 2010) "Chemical genetic strategy identifies histone deacetylase 1 (HDAC1) and HDAC2 as therapeutic targets in sickle cell disease," Proc. Natl. Acad. Sci. USA. 107(28):12617-22.
Graff (Feb. 29, 2012) "An epigenetic blockade of cognitive functions in the neurodegenerating brain," Nature. 483 (7388):222-226.
Grozinger et al. (1999) "Three proteins define a class of human histone deacetylases related to yeast Hda1p," Proc. Natl. Acad. Sci. USA. 96:4868-4873.
Guan (2009) "HDAC2 negatively regulates memory formation and synaptic plasticity," Nature. 459(7243):55-60.
Hassig et al. (1997) "Nuclear histone acetylases and deacetylases and transcriptional regulation: HATs off to HDACs," Curr. Opin. Chem. Biol. 1:300-308.
Hu et al. (2000) "Cloning and characterization of a novel human class I histone deacetylase that functions as a transcription repressor," J. Biol. Chem. 275:15254-15264.
Johnstone et al. (2002) "Histone-deacetylase inhibitors: novel drugs for the treatment of cancer," Nature Reviews in Drug Discovery. 1:287-299.

(56) References Cited

OTHER PUBLICATIONS

Kao et al. (2000) "Isolation of a novel histone deacetylase reveals that class I and class II deacetylases promote SMRT-mediated repression," Genes Dev. 14:55-66.

Kim et al. (2011) "Histone deacetylase inhibitors: molecular mechanisms of action and clinical trials as anti-cancer drugs," Am. J. Transl. Res. 3:166-179.

Kim et al. (Aug. 22, 2012) "HDAC6 Inhibitor Blocks Amyloid Beta-Induced Impairment of Mitochondrial Transport in Hippocampal Neurons," PLoS One. 7(8): e42983.

Marks et al. (2001) "Histone deacetylases and cancer: causes and therapies," Nat. Rev. Cancer. 1:194-202.

Morris (Apr. 10, 2013) "Loss of histone deacetylase 2 improves working memory and accelerates extinction learning," J. Neurosci. 33(15):6401-6411.

Simoes-Peres et al. (Jan. 29, 2013) "HDAC6 as a target for neurodegenerative diseases: what makes it different from the other HDACs," Mol. Neurodegener. 8:7.

Taunton et al. (1996) "A mammalian histone deacetylase related to the yeast transcriptional regulator Rpd3p," Science. 272:408-411.

Venter et al. (2001) "The sequence of the human genome," Science. 291:1304-1351.

Warrell et al. (1998) "Therapeutic targeting of transcription in acute promyelocytic leukemia by use of an inhibitor of histone deacetylase," J. Natl. Cancer Inst. 90:1621-1625.

Witt et al. (2009) "HDAC family: What are the cancer relevant targets?" Cancer Lett. 277:8-21.

Xiong et al. (Mar. 4, 2013) "HDAC6 mutations rescue human tau-induced microtubule defects in *Drosophila*," Proc. Natl. Acad. Sci. U S A. 110(12):4604-4609.

Yang et al. (1997) "Isolation and characterization of cDNAs corresponding to an additional member of the human histone deacetylase gene family," J. Biol. Chem. 272:28001-28007.

Zhou et al. (2001) "Cloning and characterization of a histone deacetylase, HDAC9," Proc. Natl. Acad. Sci. USA. 98:10572-10577.

International Search Report with Written Opinion corresponding to International Patent Application No. PCT/US2014/059863, mailed Feb. 19, 2015.

\* cited by examiner

PYRIMIDINE HYDROXY AMIDE COMPOUNDS AS HISTONE DEACETYLASE INHIBITORS

RELATED APPLICATIONS

This application claims priority to U.S. Provisional Application Ser. Nos. 61/889,295, filed Oct. 10, 2013; 61/944,754, filed Feb. 26, 2014; and 61/979,694, filed Apr. 15, 2014; each of which is incorporated herein by reference in its entirety.

BACKGROUND

A biological target of recent interest is histone deacetylase (HDAC) (see, for example, a discussion of the use of inhibitors of histone deacetylases for the treatment of cancer: Marks et al. *Nature Reviews Cancer* 2001, 7, 194; Johnstone et al. *Nature Reviews Drug Discovery* 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown to be effective in treating an otherwise recalcitrant cancer (Warrell et al. *J. Natl. Cancer Inst.* 1998, 90, 1621-1625).

At this time, eleven human HDACs, which use Zn as a cofactor, have been identified (Taunton et al. *Science* 1996, 272, 408-411; Yang et al. *J. Biol. Chem.* 1997, 272, 28001-28007. Grozinger et al. *Proc. Natl. Acad. Sci.* U.S.A. 1999, 96, 4868-4873; Kao et al. Genes Dev. 2000, 14, 55-66. Hu et al. *J. Biol. Chem.* 2000, 275, 15254-15264; Zhou et al. *Proc. Natl. Acad. Sci* U.S.A. 2001, 98, 10572-10577; Venter et al. *Science* 2001, 291, 1304-1351) and these members fall into three classes (class I, II, and IV) based on sequence homology to their yeast orthologues (O. Witt et al. *Cancer Letters*, 2009, 277, 8-21). Class I HDACs include HDAC1, HDAC2, HDAC3, and HDAC8, and are referred to as "classical" HDACs, which implies a catalytic pocket with a $Zn^{2+}$ ion at its base.

There remains a need for preparing structurally diverse HDAC inhibitors, particularly ones that are potent and/or selective inhibitors of particular classes of HDACs and individual HDACs.

SUMMARY OF THE INVENTION

Provided herein are compounds, pharmaceutical compositions comprising such compounds, and methods of using such compounds to treat or prevent diseases or disorders associated with HDAC activity, particularly diseases or disorders that involve any type of HDAC1, HDAC2, and/or HDAC6 expression. Diseases that involve HDAC1, HDAC2 and/or HDAC6 expression include, but are not limited to, various types of cancer, neurodegenerative diseases, and hemoglobinopathies, such as sickle-cell anemia and beta-thalassemia.

Thus, in one aspect, provided herein is a compound of Formula I:

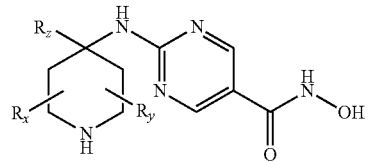

or a pharmaceutically acceptable salt thereof.

In a particular embodiment of the invention, provided herein is a compound of Formula II:

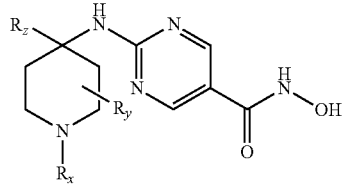

or a pharmaceutically acceptable salt thereof.

In a particular embodiment of the invention, provided herein is a compound of Formula III:

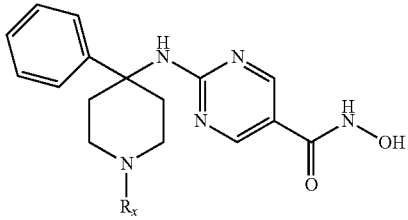

In another aspect, provided herein is a pharmaceutical composition comprising a compound of Formula I, Formula II, Formula III, or any of the compounds presented in Table 1, or pharmaceutically acceptable salts thereof, together with a pharmaceutically acceptable carrier.

In another aspect, provided herein is a method of inhibiting the activity of HDAC1, HDAC2, and/or HDAC6 in a subject comprising administering to the subject a compound of Formula I, Formula II, Formula III, or any of the compounds presented in Table 1, or a pharmaceutically acceptable salt thereof.

In another aspect, provided herein is a method of selectively inhibiting the activity of each of HDAC1, HDAC2, and/or HDAC6 over other HDACs in a subject comprising administering to the subject a compound of Formula I, Formula II, Formula III, or any of the compounds presented in Table 1, or a pharmaceutically acceptable salt thereof. In some embodiments, the compound has a selectivity for each of HDAC1, HDAC2, and/or HDAC6 that is 5 to 1000 fold greater than for other HDACs. In other embodiments, the compound has a selectivity for each of HDAC1, HDAC2, and/or HDAC6 when tested in a HDAC enzyme assay, of about 5 to 1000 fold greater than for other HDACs.

In another aspect, provided herein is a method of treating a disease mediated by one or more HDACs in a subject comprising administering to the subject in need thereof a compound of Formula I, Formula II, Formula III, or any of the compounds presented in Table 1, or pharmaceutically acceptable salts thereof. In some embodiments, the disease is mediated by HDAC1 and/or HDAC2. In other embodiments, the disease is mediated by HDAC6. In other embodiments, the disease is mediated by HDAC1 and/or HDAC2 and/or HDAC6.

In another aspect, provided herein is a method of treating a disease in a subject comprising administering to the subject a compound of Formula I, Formula II, Formula III, or any of the compounds presented in Table 1, or a pharmaceutically acceptable salt thereof. In an embodiment, the disease is a hemoglobinopathy. In another embodiment, the disease is sickle-cell disease. In yet another embodiment, the disease is beta-thalassemia.

In a further embodiment, the disease is a neurodegenerative disease. The neurodegenerative disease can be selected from a group consisting of Alzheimer's disease, frontotemporal lobe dementia, progressive supranuclear palsy, corticobasal dementia, Parkinson's disease, Huntington's disease, amytrophic lateral sclerosis, Charcot-Marie-Tooth disease and peripheral neuropathy.

In a further embodiment, the disease is a cancer or a proliferation disease. The cancer can be selected from a group consisting of lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In another embodiment, the cancer is lung cancer, colon cancer, breast cancer, neuroblastoma, leukemia, or lymphomas. In still another embodiment, the cancer is non-small cell lung cancer (NSCLC) or small cell lung cancer. In another embodiment, the cancer is a hematologic cancer. In a further embodiment, the hematologic cancer is a leukemia or lymphoma. The lymphoma can be Hodgkin's or Non Hodgkin's lymphoma.

Provided in some embodiments are methods for inhibiting migration of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for inducing maturation of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for altering cell cycle progression of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for decreasing viability and survival of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for inducing differentiation of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for enhancing low-concentration ATRA treatment of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for inducing cell cycle arrest of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for treating neuroblastoma in a subject comprising administering to the subject a therapeutically effective amount of Compound 001, Compound X, or Compound Y.

In a further embodiment of the methods of treatment described herein, the subject to be treated is a human.

Other objects, features, and advantages will become apparent from the following detailed description. The detailed description and specific examples are given for illustration only because various changes and modifications within the spirit and scope of the invention will become apparent to those skilled in the art from this detailed description. Further, the examples demonstrate the principle of the invention.

BRIEF DESCRIPTION OF THE FIGURES

FIG. 4A is a graph that shows normalized migration data (OD 570) of SK-N-SH neuroblastoma cells, normalized to CTG data. FIG. 4B is a graph that shows normalized migration data (cell count) for SK-N-SH neuroblastoma cells, normalized to CTG data. FIG. 4C is a graph that shows SK-N-SH neuroblastoma cells (CTG normalized to DMSO). Compound 001 was given at various concentrations. Gefitinib is an EGFR inhibitor. EGF was used to stimulate cancer cell migration.

FIG. 8A is a graph that shows the fold change of genes associated with maturation in BE(2)-C neuroblastoma cells upon treatment for 2 days with 3 μM Compound 001. FIG. 8B is a graph that shows the fold change of genes associated with maturation in SH-SY5Y neuroblastoma cells upon treatment for 2 days with 3 μM Compound 001. FIG. 8C is a graph that shows the fold change of genes associated with maturation in BE(2)-C neuroblastoma cells upon treatment for 2 days with 3 μM Compound X.

FIG. 12A is a graph that shows the treatment of SH-SY5Y neuroblastoma cells for 72 hours with 0, 0.5, 2, and 5 μM of a HDAC6 selective inhibitor. FIG. 12B is a graph that shows the treatment of SH-SY5Y neuroblastoma cells for 72 hours with 0, 0.5, 2, and 5 μM Compound X. FIG. 12C is a graph that shows the treatment of SH-SY5Y neuroblastoma cells for 72 hours with 0, 0.5, 2, and 5 μM Compound 001. FIG. 12D is a graph that shows the treatment of SH-SY5Y neuroblastoma cells for 72 hours with 0 and 1 μM ATRA (all trans retinoic acid).

FIG. 13A is a graph that shows the treatment of SK-N-BE(2) neuroblastoma cells with varying concentrations of Compound Y. Viability and the Caspase 3/7 Signal were measured at 48 hours. FIG. 13B is a graph that shows the treatment of SK-N-BE(2) neuroblastoma cells with varying concentrations of Compound X. Viability and the Caspase 3/7 Signal were measured at 48 hours. FIG. 13C is a graph that shows the treatment of SH-SY5Y neuroblastoma cells with varying concentrations of Compound Y. Viability and the Caspase 3/7 Signal were measured at 48 hours. FIG. 13D is a graph that shows the treatment of SH-SY5Y neuroblastoma cells with varying concentrations of Compound X. Viability and the Caspase 3/7 Signal were measured at 48 hours.

FIG. 14A is a graph that shows the percentage of the population of SK-N-BE2 neuroblastoma cells at various stages of the cell cycle 96 hours after treatment with varying concentrations of Compound Y. FIG. 14B is a graph that shows the percentage of the population of SK-N-BE2 neuroblastoma cells at various stages of the cell cycle 96 hours after treatment with varying concentrations of Compound X. FIG. 14C is a graph that shows the percentage of the population of SH-SY5Y neuroblastoma cells at various stages of the cell cycle 96 hours after treatment with varying concentrations of Compound Y. FIG. 14D is a graph that shows the percentage of the population of SH-SY5Y neuroblastoma cells at various stages of the cell cycle 96 hours after treatment with varying concentrations of Compound X.

FIG. 15A is a graph that shows the differentiation index for SK-N-BE2 cells that were treated with varying concentrations of Compound X and/or ATRA. FIG. 15B is a graph that shows the differentiation index for SH-SY5Y cells that were treated with varying concentrations of Compound X and/or ATRA. FIG. 15C is a graph that shows the differentiation index for SK-N-BE2 cells that were treated with varying concentrations of Compound Y and/or ATRA. FIG. 15D is a graph that shows the differentiation index for SH-SY5Y cells that were treated with varying concentrations of Compound Y and/or ATRA.

FIG. 16A is a graph that shows the differentiation index for SK-N-BE(2) and SH-SY5Y neuroblastoma cells that were treated with varying concentrations of ATRA. FIG. 16B is a graph that shows the differentiation index for SK-N-BE(2) neuroblastoma cells that were treated with varying concentrations of Compound Y and/or ATRA. FIG. 16C is a graph that shows the differentiation index for SK-N-BE(2) neuroblastoma cells that were treated with varying concentrations of Compound X and/or ATRA.

FIG. 17A is a graph that shows the percentage of the population of SK-N-BE(2) neuroblastoma cells at various stages of the cell cycle 4 days after treatment with varying concentrations of Compound Y and/or ATRA. FIG. 17B is a graph that shows the percentage of the population of SK-N-BE(2) neuroblastoma cells at various stages of the cell cycle 4 days after treatment with varying concentrations of Compound X and/or ATRA. FIG. 17C is a graph that shows the fold change of p21 in SK-N-BE(2) cells 4 days after treatment with varying concentrations of Compound Y and/or ATRA. FIG. 17D is a graph that shows the fold change of p21 in SK-N-BE(2) cells 4 days after treatment with varying concentrations of Compound X and/or ATRA.

FIG. 18A is a graph that shows the percentage of the population of SH-SY5Y neuroblastoma cells at various stages of the cell cycle 4 days after treatment with varying concentrations of Compound Y and/or ATRA. FIG. 18B is a graph that shows the percentage of the population of SH-SY5Y neuroblastoma cells at various stages of the cell cycle 4 days after treatment with varying concentrations of Compound X and/or ATRA. FIG. 18C is a graph that shows the fold change of p21 in SH-SY5Y cells 4 days after treatment with varying concentrations of Compound Y and/or ATRA. FIG. 18D is a graph that shows the fold change of p21 in SH-SY5Y cells 4 days after treatment with varying concentrations of Compound X and/or ATRA.

DETAILED DESCRIPTION

Figure 1:
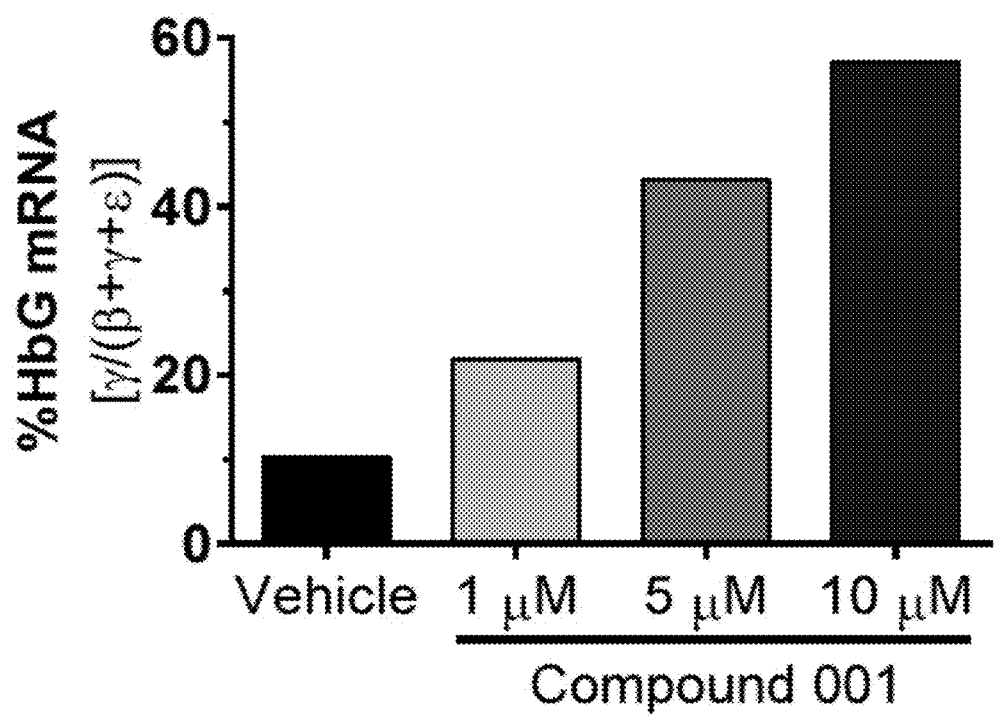
FIG. 1 is a graph showing fetal globin induction (% HbG mRNA) upon administering Compound 001 at 1, 5, and 10 µM.
Figure 2A:
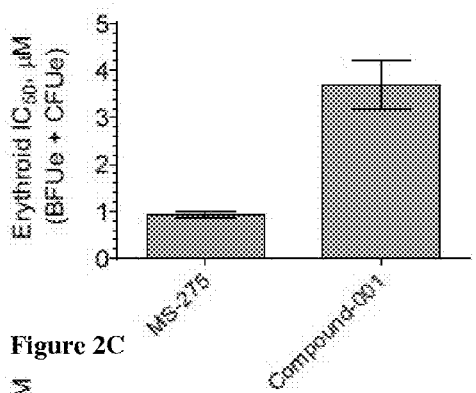
FIGS. 2A-F: Compound 001 and MS-275 (Entinostat) were tested for their effects on human erythroid, myeloid and megakaryocyte hematopoietic progenitor proliferation in media formulations containing various cytokines. Left panels show the concentration of 50% inhibition of colony growth ($IC_{50}$) for each compound. Right panels show the number absolute number of colonies per plate in each assay were plotted for solvent control (DMSO) or indicated compounds at 1 µM.
Figure 2B:
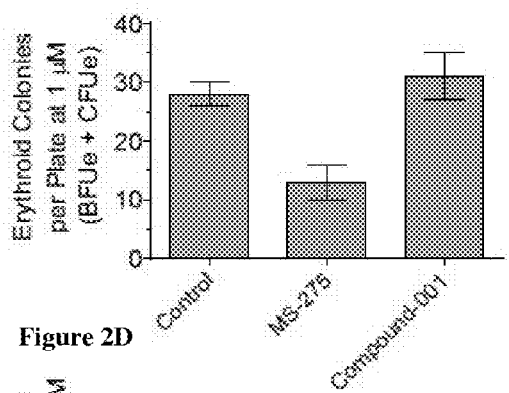
Figure 2C:
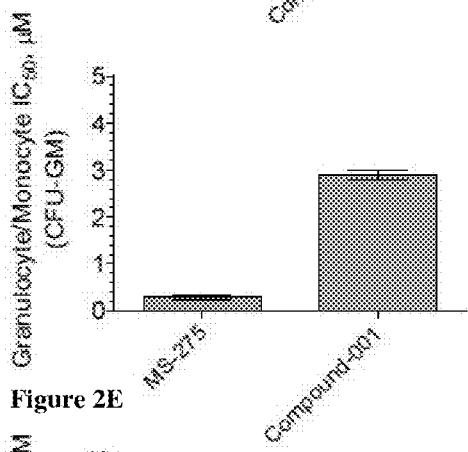
Figure 2D:
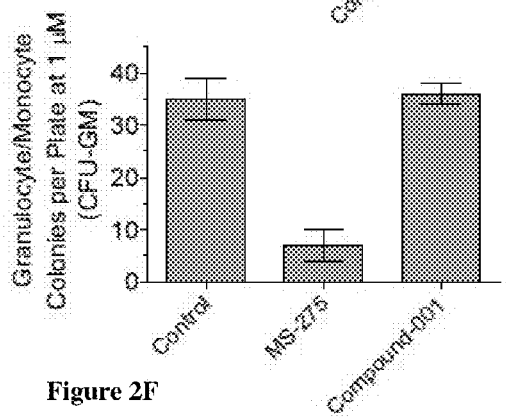
Figure 2E:
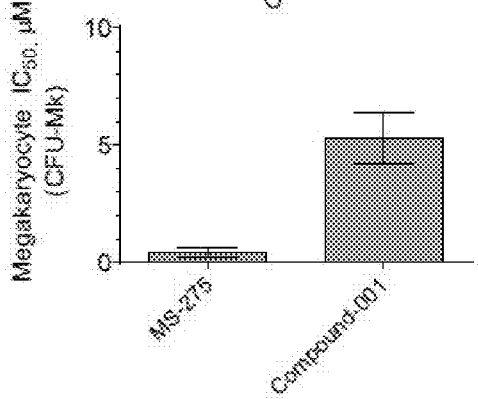
Figure 2F:
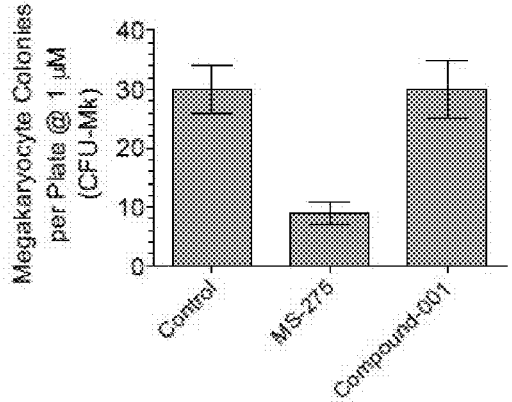

The instant application is directed, generally, to compounds, pharmaceutical compositions comprising such compounds, and methods of using such compounds to treat or prevent diseases or disorders associated with HDAC activity, particularly diseases or disorders that involve any type of HDAC1, HDAC2, or HDAC6 expression. Such diseases include, but are not limited to, cancer, neurodegenerative disease, sickle-cell anemia, and beta-thalassemia.

Inhibition of HDAC1 and HDAC2 has been shown to derepress fetal globin. Fetal hemoglobin (HbF) derepression, or induction, is an established therapeutic strategy in sickle cell disease, and could also be effective in treating beta-thalassemia. Hydroxyurea is currently the only drug with proven efficacy in sickle cell disease (SCD). This therapy is cytotoxic, poorly tolerated, and only reduces the frequency and severity of sickle cell crises in a subset of patients. There are no approved drugs for the treatment of beta-thalassemia. Fetal (γ) globin expression is silenced in adults partly through the action of a complex containing BCL11A and HDACs 1 and 2. Genetic ablation and chemical inhibition of HDAC1 or HDAC2 results in the derepression of γ globin in adult bone marrow derived erythroid cells (Bradner, *Proc Natl Acad Sci* 2010). While a variety of non-specific HDAC inhibitors have been used successfully to induce HbF, further clinical development has been limited by their variable efficacy and concerns over off target side-effects observed in small clinical trials. Therefore, development of selective and potent HDAC1 and HDAC2 inhibitors leading to HbF reactivation represents a refined and more targeted therapeutic approach for the treatment of SCD and beta-thalassemia.

It has also been shown that HDAC2 expression and activity are elevated in neurodegenerative diseases (Guan, 2009; Morris, 2013). Increasing the expression of HDAC2 impairs cognitive function in mice. Inhibition of HDAC2 by gene disruption restores cognitive function in mouse models of Alzheimer's disease (Guan, 2009; Morris, 2013; Graff, 2014). In addition, the activity of HDAC6 is implicated in neurodegenerative diseases (Xiong, 2013; Simoes-Peres, 2013; Kim, 2012). Combined inhibition of HDAC2 and HDAC6 could have a more profound effect on the development of neurodegenerative diseases than inhibition of either enzyme alone.

It has also been shown that deregulated HDAC1 expression is particularly common in advanced cancers of the gastrointestinal system, such as, for example, pancreatic, colorectal, and liver (hepatocellular) carcinomas, as well as in prostate and breast cancer. HDAC2 and HDAC3 expression are also associated with advanced stage disease and poor prognosis in gastric, prostate and colorectal cancers. HDAC2 is also over expressed in cervical cancer. Clinical trials for the treatment of patients with advanced solid tumors, lymphomas, and leukemias utilizing class I selective HDAC inhibitors such as MS275, depsipeptide, and MGCD0103 have been published (O. Witt et al., *Cancer Letters*, 2009, 277, 8-21 and H-J. Kim and S.-C. Bae, *Am. J. Transl. Res.* 2011; 3(2): 166-179). HDACs have also been found to repress HIV-1 (Human Immunodeficiency Virus) transcription through deacetylation events, particularly in latently infected resting CD4+ T cells.

As such, it is known that HDAC inhibitors can induce the transcriptional activation of the HIV-1 promoter, or re-activate latent HIV-1 from the patient viral reservoir. It is generally accepted that the use of HDAC inhibitors in the treatment of HIV infection can be valuable in purging the latently infected reservoirs in patients, particularly patients undergoing Highly Active Antiretroviral Therapy (HAAT).

The compounds described herein have HDAC1 $IC_{50}$ values ranging from 1 to 2000 nM and HDAC2 $IC_{50}$ values ranging from 10 to 3000 nM, demonstrating approximately 2- to 100-fold selectivity over HDAC3, respectively.

The compounds described herein have HDAC6 $IC_{50}$ values ranging from 1 to 20 nM, demonstrating approximately 5- to 1000-fold selectivity than for other HDACs.

DEFINITIONS

Listed below are definitions of various terms used to describe this invention. These definitions apply to the terms as they are used throughout this specification and claims, unless otherwise limited in specific instances, either individually or as part of a larger group.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The term "alkenyl" denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl" denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl moiety.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like. In some embodiments, aryl groups have 6 carbon atoms. In some embodiments, aryl groups have from six to ten carbon atoms. In some embodiments, aryl groups have from six to sixteen carbon atoms.

The term "cycloalkyl" denotes a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cyclopentyl and cyclooctyl; and examples of $C_{3-12}$-cycloalkyl include, but are not limited to, cyclopropyl, cyclobutyl, cyclopentyl, cyclohexyl, bicyclo[2.2.1]heptyl, and bicyclo[2.2.2]octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "heterocycloalkyl" refers to a non-aromatic 3-, 4-, 5-, 6- or 7-membered ring or a bi- or tri-cyclic group fused of non-fused system, where (i) each ring contains between one and three heteroatoms independently selected from oxygen, sulfur, and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

In accordance with the invention, any of the aryls, substituted aryls, heteroaryls and substituted heteroaryls described herein, can be any aromatic group.

The terms "halo" and "halogen" refer to an atom selected from fluorine, chlorine, bromine, and iodine.

The term "haloalkyl" refers to alkyl radicals wherein any one or more of the alkyl carbon atoms is substituted with halo as defined above. Haloalkyl also embraces monohaloalkyl, dihaloalkyl, and polyhaloalkyl radicals. Examples of haloalkyl include, but are not limited to, fluoromethyl, difluoromethyl, trifluoromethyl, chloromethyl, dichloromethyl, trichloromethyl, and pentafluoroethyl.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "inhibitor" is synonymous with the term antagonist.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

Combinations of substituents and variables envisioned by this invention are only those that result in the formation of stable compounds. The term "stable" refers to compounds which possess stability sufficient to allow manufacture and which maintains the integrity of the compound for a sufficient period of time to be useful for the purposes detailed herein (e.g., therapeutic or prophylactic administration to a subject).

The term "subject" refers to a mammal. A subject therefore refers to, for example, dogs, cats, horses, cows, pigs, guinea pigs, and the like. Preferably the subject is a human. When the subject is a human, the subject may be referred to herein as a patient.

The terms "treat", "treating" and "treatment" refer to a method of alleviating or abating a disease and/or its attendant symptoms.

Compounds of the Invention

In one aspect, the invention provides a compound of Formula I:

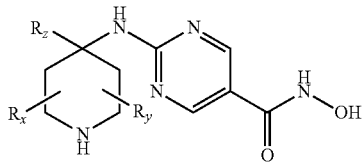

I or a pharmaceutically acceptable salt thereof,
wherein, $R_x$ is selected from the group consisting of $C_{1-6}$-alkyl, $C_{1-6}$-alkoxy, halo, —OH, —C(O)$R^1$, —CO$_2$$R^1$, —C(O)N($R^1$)$_2$, aryl, —C(S)N($R^1$)$_2$, and S(O)$_2$$R^1$, wherein aryl may be optionally substituted by one or more groups selected from $C_{1-6}$-alkyl, $C_{1-6}$-alkoxy, —OH, halo, and haloalkyl;

$R_y$ is selected from the group consisting of H, $C_{1-6}$-alkyl, $C_{1-6}$-alkoxy, halo, —OH, —C(O)$R^1$, —CO$_2$$R^1$, and —C(O)N($R^1$)$_2$;

$R_z$ is selected from the group consisting of $C_{1-6}$-alkyl, $C_{1-6}$-alkenyl, $C_{1-6}$-alkynyl, $C_{3-8}$-cycloalkyl, $C_{3-7}$-heterocycloalkyl, aryl, and heteroaryl, each of which may be optionally substituted by $C_{1-6}$-alkyl, $C_{1-6}$-alkoxy, halo, or —OH; and each $R^1$ is, independently for each occurrence, selected from the group consisting of H, $C_{1-6}$-alkyl, $C_{3-8}$-cycloalkyl, $C_{3-7}$-heterocycloalkyl, aryl, heteroaryl, $C_{1-6}$-alkyl-cyclo alkyl, $C_{1-6}$-alkyl-heterocycloalkyl, $C_{1-6}$-alkyl-aryl, and $C_{1-6}$-alkyl-heteroaryl, wherein $C_{3-8}$-cyclo alkyl, $C_{3-7}$-heterocycloalkyl, aryl, heteroaryl, $C_{1-6}$-alkyl-cyclo alkyl, $C_{1-6}$-alkyl-heterocycloalkyl, $C_{1-6}$-alkyl-aryl, and $C_{1-6}$-alkyl-heteroaryl may be optionally substituted by one or more groups selected from $C_{1-6}$-alkyl, $C_{1-6}$-alkoxy, —OH, halo, and haloalkyl.

In an embodiment of the compound of Formula I or a pharmaceutically acceptable salt thereof, $R_x$ is selected from the group consisting of $C_{1-6}$-alkyl, $C_{1-6}$-alkoxy, halo, —OH, —C(O)$R^1$, —CO$_2$$R^1$, and —C(O)N($R^1$)$_2$;

$R_y$ is selected from the group consisting of H, $C_{1-6}$-alkyl, $C_{1-6}$-alkoxy, halo, —OH, —C(O)$R^1$, —CO$_2$$R^1$, and —C(O)N($R^1$)$_2$;

$R_z$ is selected from the group consisting of $C_{1-6}$-alkyl, $C_{1-6}$-alkenyl, $C_{1-6}$-alkynyl, $C_{3-8}$-cycloalkyl, $C_{3-7}$-heterocycloalkyl, aryl, and heteroaryl, each of which may be optionally substituted by $C_{1-6}$-alkyl, $C_{1-6}$-alkoxy, halo, or —OH; and each $R^1$ is, independently for each occurrence, selected from the group consisting of H, $C_{1-6}$-alkyl, $C_{3-8}$-cycloalkyl, $C_{3-7}$-heterocycloalkyl, aryl, heteroaryl, $C_{1-6}$-alkyl-cyclo alkyl, $C_{1-6}$-alkyl-heterocycloalkyl, $C_{1-6}$-alkyl-aryl, and $C_{1-6}$-alkyl-heteroaryl.

In one embodiment of the compound of Formula I, provided herein is a compound of Formula II:

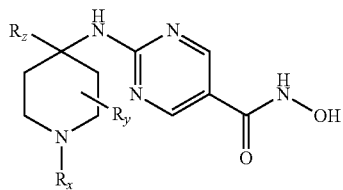

II or a pharmaceutically acceptable salt thereof,
wherein, $R_x$ is independently selected from the group consisting of aryl, —C(O)$R^1$, —CO$_2$$R^1$, —C(O)N($R^1$)$_2$, —C(S)N($R^1$)$_2$, and S(O)$_2$$R^1$;

$R_y$ is selected from the group consisting of H, $C_{1-6}$-alkyl, and halo; and $R_z$ is selected from the group consisting of $C_{1-6}$-alkyl, $C_{3-8}$-cycloalkyl, $C_{3-7}$-heterocycloalkyl, aryl, and heteroaryl.

In one embodiment of the compound of Formula II, or a pharmaceutically acceptable salt thereof, $R_x$ is independently selected from the group consisting of —C(O)$R^1$, —CO$_2$$R^1$, and —C(O)N($R^1$)$_2$; and $R_z$ is selected from the group consisting of $C_{1-6}$-alkyl, $C_{3-8}$-cycloalkyl, $C_{3-7}$-heterocycloalkyl, aryl, and heteroaryl.

In an embodiment of the compounds of Formula I or II, $R_z$ is $C_{1-6}$-alkyl or aryl. In preferred embodiments of the compounds of Formula I or II, $R_z$ is isopropyl or phenyl. In another embodiment of the compounds of Formula I or II, $R_z$ is methyl.

In another embodiment of the compounds of Formula I or II, $R_x$ is —C(O)N($R^1$)$_2$ or —C(O)NH$R^1$. In yet another embodiment of the compounds of Formula I or II, $R_x$ is —C(O)$R^1$ or —CO$_2$$R^1$. In yet another embodiment of the compounds of Formula I or II, $R_x$ is —C(S)N($R^1$)$_2$, —C(S)NH$R^1$, or S(O)$_2$$R^1$.

In an embodiment of the compounds of Formula I or II, at least one of $R^1$ is selected from the group consisting of $C_{1-6}$-alkyl, aryl, $C_{1-6}$-alkyl-aryl and $C_{1-6}$-alkyl-heteroaryl, wherein aryl, $C_{1-6}$-alkyl-aryl and $C_{1-6}$-alkyl-heteroaryl may be optionally substituted by one or more groups selected from $C_{1-6}$-alkyl, $C_{1-6}$-alkoxy, —OH, halo, and haloalkyl. In a further embodiment, $R^1$ is —CH$_3$, —CH$_2$CH$_3$, phenyl, —CH$_2$- phenyl, or —CH$_2$-indolyl, wherein phenyl, —CH$_2$-phenyl, or —CH$_2$-indolyl may be optionally substituted by one or more groups selected from C$_{1-6}$-alkyl and halo.

In another embodiment of the compounds of Formula I or II, at least one of R$^1$ is, independently for each occurrence, selected from the group consisting of C$_{1-6}$-alkyl, aryl, and C$_{1-6}$-alkyl-aryl. In a further embodiment, at least one of R$^1$ may be —CH$_3$, —CH$_2$CH$_3$, —CH$_2$-phenyl, or phenyl.

In another embodiment of the compounds of Formulas I or II, at least one of R$^1$ is phenyl, wherein phenyl is optionally substituted by one or more groups selected from C$_{1-6}$-alkyl, C$_{1-6}$-alkoxy, halo, and haloalkyl. In preferred embodiments, at least one of R$^1$ is phenyl, wherein phenyl is optionally substituted by one or more groups selected from CH$_3$, —OCH$_3$, fluoro, chloro, and CF$_3$.

In yet another preferred embodiment of the compounds of Formula I or II, R$_y$ is H.

In another embodiment of the compounds of Formula I or II, R$_x$ is —C(O)R$^1$; and R$^1$ is C$_{1-6}$-alkyl, C$_{1-6}$-alkyl-aryl or C$_{1-6}$-alkyl-heteroaryl, wherein C$_{1-6}$-alkyl-aryl or C$_{1-6}$-alkyl-heteroaryl may be optionally substituted by one or more groups selected from C$_{1-6}$-alkyl, C$_{1-6}$-alkoxy, —OH, halo, and haloalkyl. In a preferred embodiment, R$^1$ is CH$_2$-phenyl or CH$_2$-indolyl, wherein CH$_2$-phenyl or CH$_2$-indolyl may be optionally substituted by one or more groups selected from C$_{1-6}$-alkyl and halo.

In another embodiment of the compound of Formula I, provided herein is a compound of Formula III:

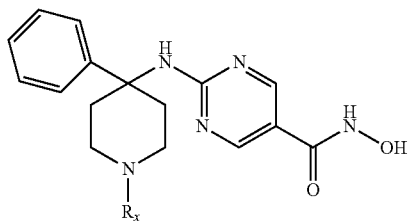

III or a pharmaceutically acceptable salt thereof,
wherein,
R$_x$ is selected from the group consisting of aryl, —C(O)R$^1$, —CO$_2$R$^1$, —C(O)N(R$^1$)$_2$, —C(S)N(R$^1$)$_2$, and S(O)$_2$R$^1$, wherein aryl may be optionally substituted by one or more groups selected from C$_{1-6}$-alkyl, C$_{1-6}$-alkoxy, —OH, halo, and haloalkyl; and each R$^1$ is, independently for each occurrence, selected from the group consisting of H, C$_{1-6}$-alkyl, C$_{3-8}$-cycloalkyl, C$_{3-7}$-heterocycloalkyl, aryl, heteroaryl, C$_{1-6}$-alkyl-cycloalkyl, C$_{1-6}$-alkyl-heterocycloalkyl, C$_{1-6}$-alkyl-aryl, and C$_{1-6}$-alkyl-heteroaryl, wherein C$_{1-6}$-alkyl, C$_{3-8}$-cycloalkyl, C$_{3-7}$-heterocycloalkyl, aryl, heteroaryl, C$_{1-6}$-alkyl-cycloalkyl, C$_{1-6}$-alkyl-heterocycloalkyl, C$_{1-6}$-alkyl-aryl, and C$_{1-6}$-alkyl-heteroaryl may be optionally substituted by one or more groups selected from C$_{1-6}$-alkyl, C$_{1-6}$-alkoxy, halo, and haloalkyl.

In an embodiment of the compounds of Formula III, R$_x$ is —C(O)NHR$^1$, —C(S)NHR$^1$, or S(O)$_2$R$^1$; and R$^1$ is, independently for each occurrence, selected from the group consisting of C$_{1-6}$-alkyl, C$_{3-8}$-cycloalkyl, C$_{3-7}$-heterocycloalkyl, aryl, heteroaryl, C$_{1-6}$-alkyl-cycloalkyl, C$_{1-6}$-alkyl-heterocycloalkyl, C$_{1-6}$-alkyl-aryl, and C$_{1-6}$-alkyl-heteroaryl, wherein C$_{3-8}$-cycloalkyl, C$_{3-7}$-heterocycloalkyl, aryl, and heteroaryl may be optionally substituted by one or more groups selected from C$_{1-6}$-alkyl, C$_{1-6}$-alkoxy, —OH, halo, and haloalkyl.

In another embodiment of the compounds of Formula III, at least one of R$^1$ is selected from the group consisting of C$_{1-6}$-alkyl, aryl, heteroaryl, C$_{1-6}$-alkyl-aryl, and C$_{1-6}$-alkyl-heteroaryl, wherein aryl may be optionally substituted by one or more groups selected from C$_{1-6}$-alkyl, C$_{1-6}$-alkoxy, —OH, halo, and haloalkyl.

In another embodiment of the compounds of Formula III, at least one of R$^1$ is aryl, wherein aryl is optionally substituted by one or more groups selected from C$_{1-6}$-alkyl, C$_{1-6}$-alkoxy, halo, and haloalkyl.

In a preferred embodiment of the compounds of Formula III, at least one of R$^1$ is phenyl, wherein phenyl is optionally substituted by one or more groups selected from CH$_3$, —OCH$_3$, fluoro, chloro, and CF$_3$.

In another embodiment of the compounds of Formula III, R$_x$ is —C(O)R$^1$; and

R$^1$ is C$_{1-6}$-alkyl, C$_{1-6}$-alkyl-aryl or C$_{1-6}$-alkyl-heteroaryl, wherein C$_{1-6}$-alkyl-aryl or C$_{1-6}$-alkyl-heteroaryl may be optionally substituted by one or more groups selected from C$_{1-6}$-alkyl, C$_{1-6}$-alkoxy, —OH, halo, and haloalkyl. In a preferred embodiment, R$^1$ is CH$_2$-phenyl or CH$_2$-indole, wherein CH$_2$-phenyl or CH$_2$-indole may be optionally substituted by one or more groups selected from C$_{1-6}$-alkyl or halo.

Representative compounds of Formulas I, II, and III include, but are not limited to the following compounds of Table 1:

TABLE 1

| ID | Structure | IC$_{50}$, nM | | | |
| --- | --- | --- | --- | --- | --- |
| | | HDAC1 | HDAC2 | HDAC3 | HDAC6 |
| 001 | 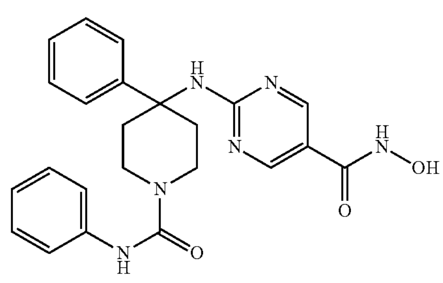 [SMILES: O=C(NO)c1cnc(NC2(c3ccccc3)CCN(C(=O)Nc3ccccc3)CC2)nc1] | 38 | 34 | 1010 | 1.9 |

TABLE 1-continued

| ID | Structure | IC₅₀, nM | | | |
|---|---|---|---|---|---|
| | | HDAC1 | HDAC2 | HDAC3 | HDAC6 |
| 002 | 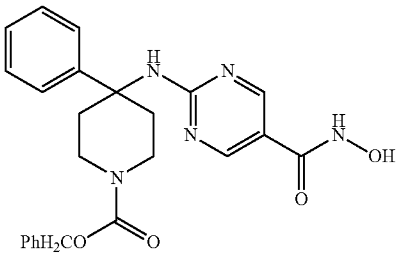 | 1010 | 983 | 1642 | 2.6 |
| 003 | 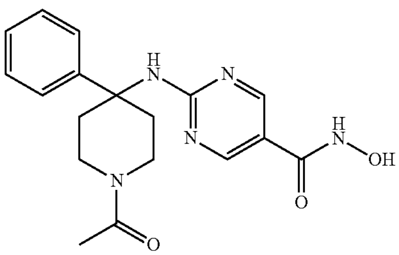 [SMILES: CC(=O)N1CCC(Nc2ncc(C(=O)NO)cn2)(c2ccccc2)CC1] | 346 | 254 | 840 | 1.6 |
| 004 | 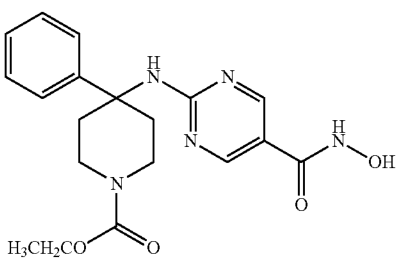 | 275 | 321 | 1003 | 2.9 |
| 005 | 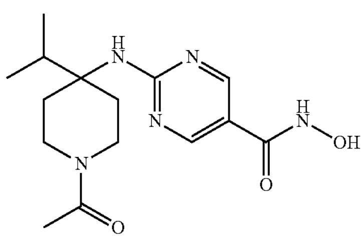 [SMILES: CC(=O)N1CCC(Nc2ncc(C(=O)NO)cn2)(C(C)C)CC1] | 1828 | 2387 | 8180 | 5.9 |
| 006 | 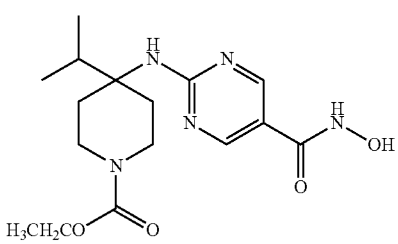 | 697 | 809 | 3781 | 4 |
| 007 | 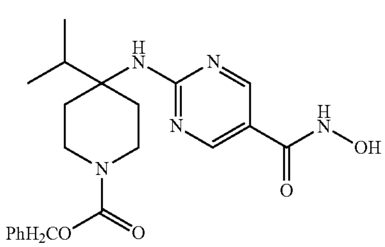 | 119 | 121 | 879 | 5.1 |

TABLE 1-continued
| ID | Structure | IC₅₀, nM | | | |
|---|---|---|---|---|---|
| | | HDAC1 | HDAC2 | HDAC3 | HDAC6 |
| 008 | 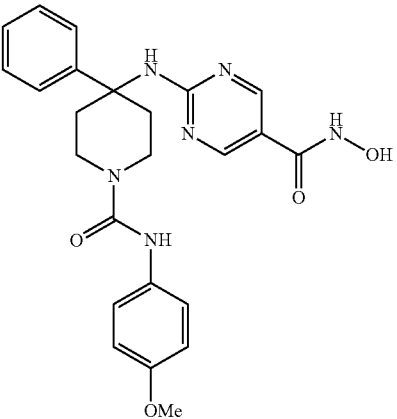 [SMILES: COc1ccc(NC(=O)N2CCC(Nc3ncc(C(=O)NO)cn3)(c3ccccc3)CC2)cc1] | 21 | 24 | 546 | 1.5 |
| 009 | 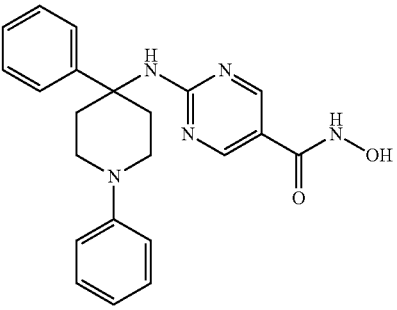 [SMILES: O=C(NO)c1cnc(NC2(c3ccccc3)CCN(c3ccccc3)CC2)nc1] | 356 | 380 | 1785 | 2.1 |
| 010 | 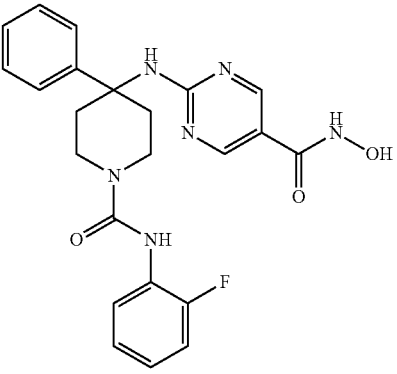 [SMILES: O=C(NO)c1cnc(NC2(c3ccccc3)CCN(C(=O)Nc3ccccc3F)CC2)nc1] | 18 | 27 | 824 | 1.7 |
| 011 | 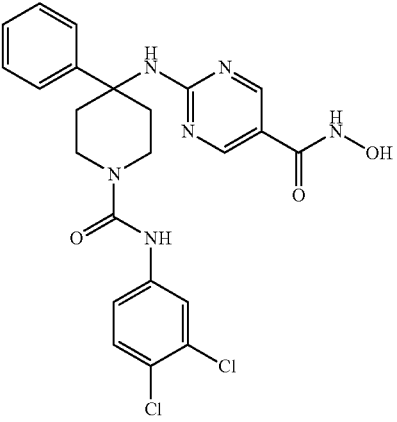 [SMILES: O=C(NO)c1cnc(NC2(c3ccccc3)CCN(C(=O)Nc3ccc(Cl)c(Cl)c3)CC2)nc1] | 110 | 177 | 2164 | 14 |

TABLE 1-continued

| ID | Structure | IC$_{50}$, nM | | | |
|---|---|---|---|---|---|
| | | HDAC1 | HDAC2 | HDAC3 | HDAC6 |
| 012 | 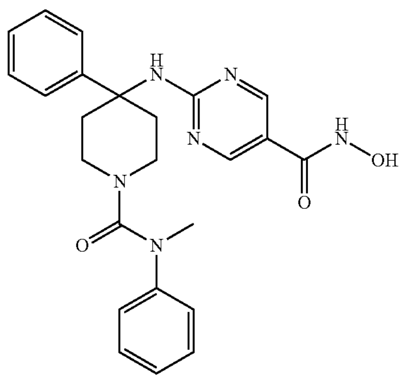 [SMILES: CN(C(=O)N1CCC(Nc2ncc(C(=O)NO)cn2)(c2ccccc2)CC1)c1ccccc1] | 266 | 377 | 1624 | 2.2 |
| 013 | 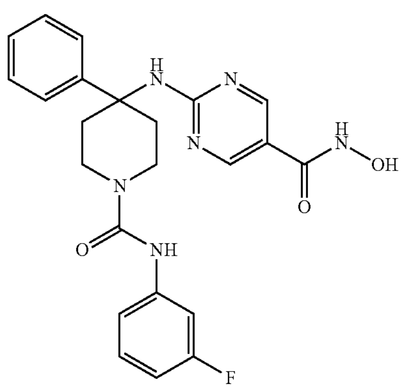 [SMILES: O=C(NO)c1cnc(NC2(c3ccccc3)CCN(C(=O)Nc3cccc(F)c3)CC2)nc1] | 50 | 74 | 1081 | 2.5 |
| 014 | 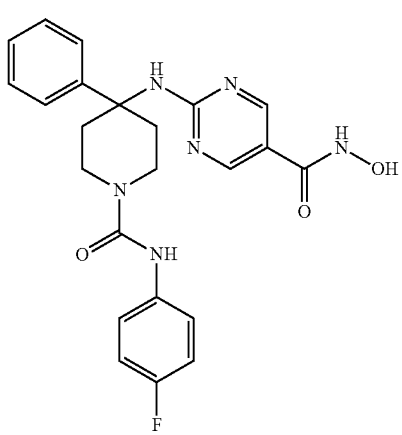 [SMILES: O=C(NO)c1cnc(NC2(c3ccccc3)CCN(C(=O)Nc3ccc(F)cc3)CC2)nc1] | 33 | 43 | 1072 | 2.0 |

TABLE 1-continued
| ID | Structure | IC₅₀, nM | | | |
|---|---|---|---|---|---|
| | | HDAC1 | HDAC2 | HDAC3 | HDAC6 |
| 015 | 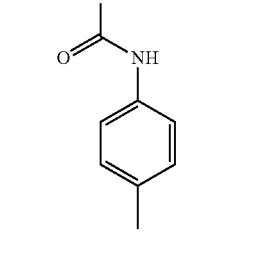 | 34 | 46 | 693 | 2.0 |
| 016 | 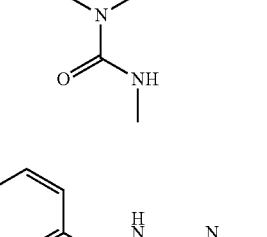 | 170 | 207 | 987 | 1.7 |
| 017 | 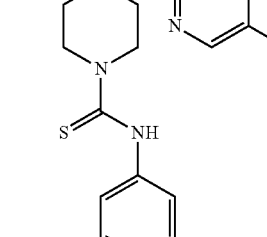 | 5.9 | 5.2 | 111 | 2.4 |
| 018 | 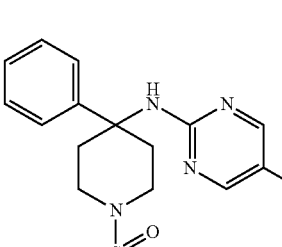 | 551 | 644 | 2485 | 5.1 |

TABLE 1-continued
| ID | Structure | IC$_{50}$, nM | | | |
| | | HDAC1 | HDAC2 | HDAC3 | HDAC6 |
|---|---|---|---|---|---|
| 019 | 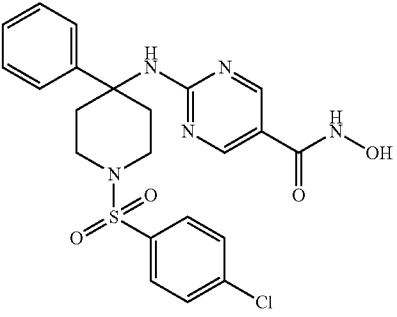 [SMILES: O=C(NO)c1cnc(NC2(c3ccccc3)CCN(S(=O)(=O)c3ccc(Cl)cc3)CC2)nc1] | 854 | 987 | 3190 | 5.0 |
| 020 | 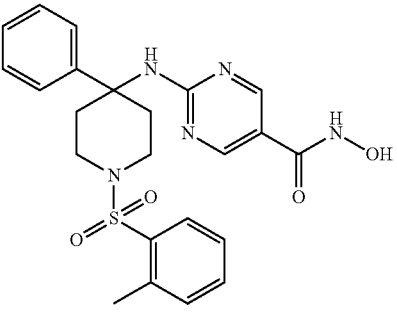 [SMILES: Cc1ccccc1S(=O)(=O)N1CCC(Nc2ncc(C(=O)NO)cn2)(c2ccccc2)CC1] | 372 | 423 | 1983 | 4.5 |
| 021 | 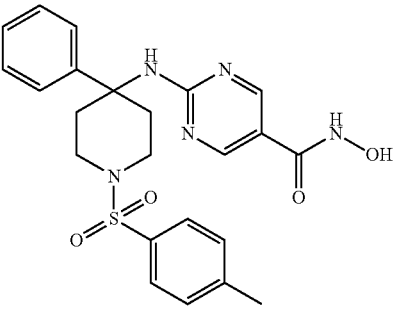 [SMILES: Cc1ccc(S(=O)(=O)N2CCC(Nc3ncc(C(=O)NO)cn3)(c3ccccc3)CC2)cc1] | 570 | 642 | 2513 | 4.5 |
| 022 | 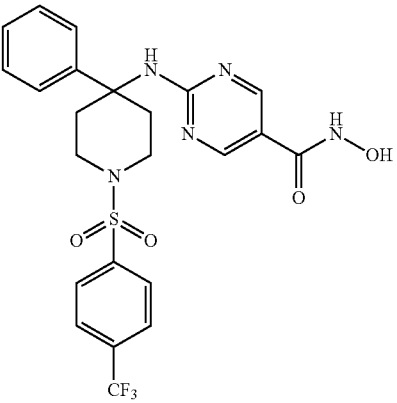 [SMILES: O=C(NO)c1cnc(NC2(c3ccccc3)CCN(S(=O)(=O)c3ccc(C(F)(F)F)cc3)CC2)nc1] | 704 | 782 | 2703 | 7.3 |

TABLE 1-continued

| ID | Structure | IC$_{50}$, nM | | | |
|---|---|---|---|---|---|
| | | HDAC1 | HDAC2 | HDAC3 | HDAC6 |
| 023 | 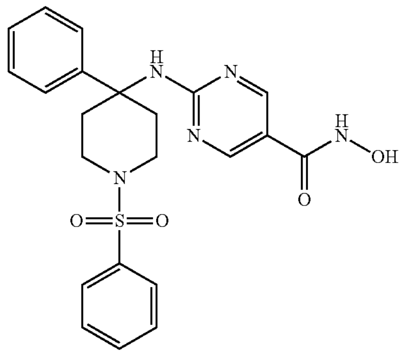 [SMILES: O=C(NO)c1cnc(NC2(c3ccccc3)CCN(S(=O)(=O)c3ccccc3)CC2)nc1] | 844 | 829 | 3545 | 4.6 |
| 024 | 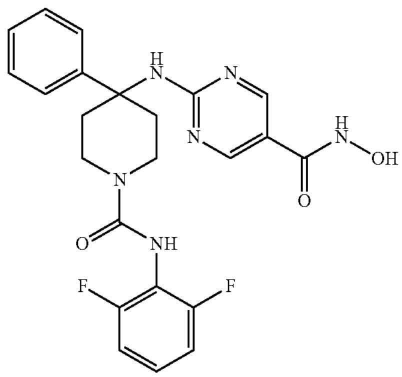 [SMILES: O=C(NO)c1cnc(NC2(c3ccccc3)CCN(C(=O)Nc3c(F)cccc3F)CC2)nc1] | 22 | 22 | 761 | 3.7 |
| 025 | 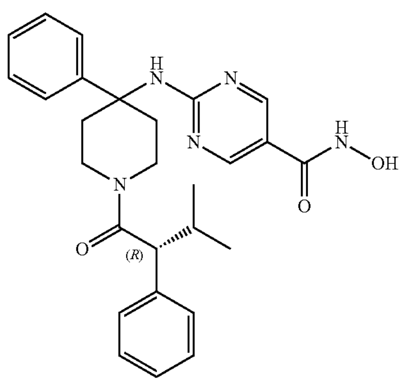 | 20 | 18 | 84 | 13 |
| 026 | 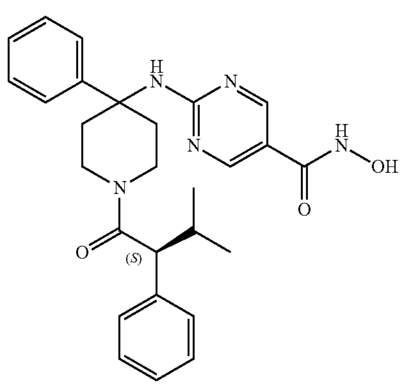 | 206 | 173 | 1100 | 5.0 |

TABLE 1-continued

| ID | Structure | IC$_{50}$, nM | | | |
|---|---|---|---|---|---|
| | | HDAC1 | HDAC2 | HDAC3 | HDAC6 |
| 027 | 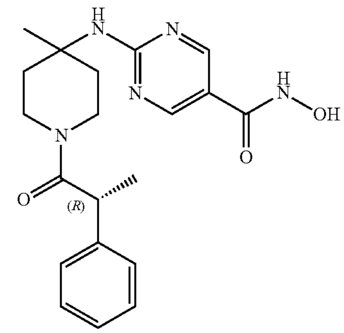 | 130 | 103 | 422 | 12 |
| 028 | 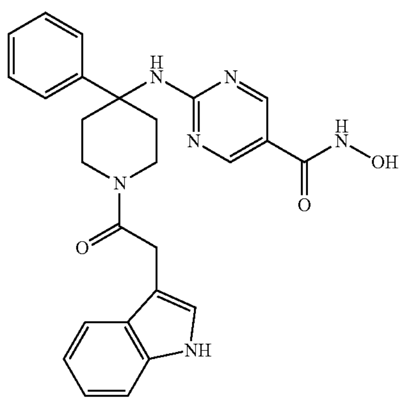 [SMILES: O=C(NO)c1cnc(NC2(c3ccccc3)CCN(C(=O)Cc3c[nH]c4ccccc34)CC2)nc1] | 3 | 2 | 24 | 2.8 |
| 029 | 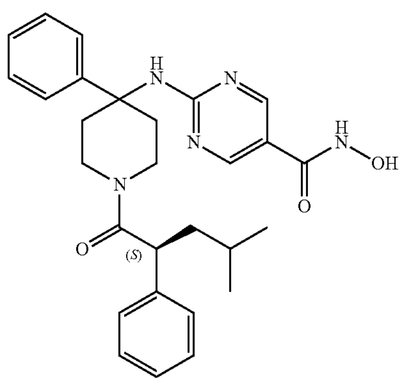 | 102 | 93 | 914 | 11 |
| 030 | 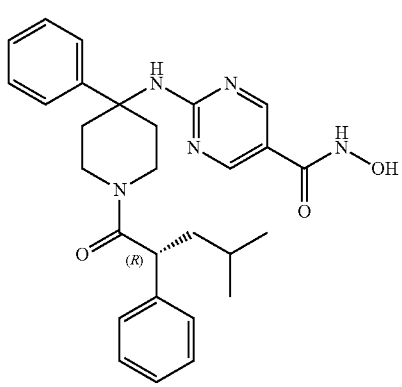 | 23 | 22 | 114 | 12 |

TABLE 1-continued

| ID | Structure | IC$_{50}$, nM | | | |
|---|---|---|---|---|---|
| | | HDAC1 | HDAC2 | HDAC3 | HDAC6 |
| 031 | 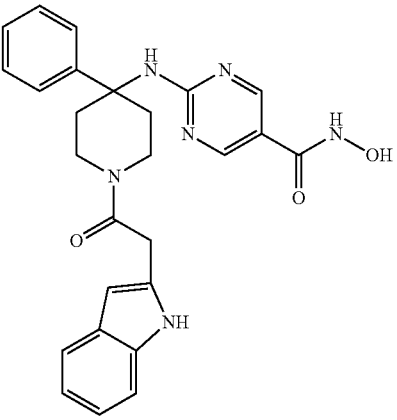 [SMILES: O=C(NO)c1cnc(NC2(c3ccccc3)CCN(C(=O)Cc3cc4ccccc4[nH]3)CC2)nc1] | 10 | 9 | 42 | 5 | or pharmaceutically acceptable salts thereof.

In preferred embodiments, the compounds of the instant invention have one or more of the following properties: the compound is capable of inhibiting at least one histone deacetylase (HDAC); the compound is capable of inhibiting HDAC1, HDAC2, and/or HDAC6; the compound selectively inhibits HDAC1, HDAC2 and/or HDAC6 over other HDACs.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

In another aspect, the invention provides a method of synthesizing a compound of Formula I, Formula II, or any of the compounds presented in Table 1. The synthesis of the compounds of the invention can be found in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, and subsequent editions thereof.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxan, tetrahydrofuran or methanol.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., "Enantiomers, Racemates, and Resolutions" (John Wiley & Sons, 1981). The compounds of this invention may also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Pharmaceutical Compositions

The invention also provides for a pharmaceutical composition comprising a compound of instant invention, or a pharmaceutically acceptable salt thereof, together with a pharmaceutically acceptable carrier.

In another aspect, the invention provides a pharmaceutical composition comprising any of the compounds of the instant invention (Formula I, Formula II, Formula III, or any of the compounds presented in Table 1) or pharmaceutically acceptable salts thereof, together with a pharmaceutically acceptable carrier.

The pharmaceutical compositions of the present invention comprise a therapeutically effective amount of a compound of the present invention formulated together with one or more pharmaceutically acceptable carriers. The term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Compounds of the invention can be administered as pharmaceutical compositions by any conventional route, in particular enterally, for example, orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Methods of the Invention

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention means a sufficient amount of the compound so as to decrease the symptoms of a disorder in a subject. As is well understood in the medical arts, a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In one aspect, the invention provides a method of selectively inhibiting the activity of each of HDAC1, HDAC2, and/or HDAC6 over other HDACs in a subject, comprising administering a compound of Formula I, Formula II, Formula III, or any of the compounds presented in Table 1, or pharmaceutically acceptable salts thereof.

In one embodiment, the compound has a selectivity for each of HDAC1, HDAC2 and HDAC6 of about 2 to 1000 fold greater than for other HDACs. In another embodiment, the compound has a selectivity for each of HDAC1, HDAC2, and or HDAC6 when tested in a HDAC enzyme assay of about 2 to 1000 fold greater than for other HDACs.

In another aspect, the invention provides a method of treating a disease mediated by an HDAC, specifically HDAC1, HDAC2, or HDAC6 in a subject comprising administering to the subject a compound of Formula I, Formula II, Formula III, or any of the compounds presented in Table 1, and pharmaceutically acceptable salts thereof.

In another aspect, the invention provides a method of treating a disease mediated by one or more HDACs in a subject comprising administering to the subject in need thereof a compound of Formula I, Formula II, Formula III, or any of the compounds presented in Table 1, or pharmaceutically acceptable salts thereof.

Inhibition of HDAC1 and HDAC2 is sufficient to derepress fetal globin. In cultured human CD34+ bone marrow cells undergoing erythroid differentiation, these compounds induced a dose dependent increase in fetal hemoglobin expression, with a 2-fold induction observed at 1 μM and 5-fold induction observed at 10 μM. Cytotoxicity of these compounds was minimal, showing IC$_{50}$ values ranging from 1 to 5 μM. The selective HDAC1 and HDAC2 inhibitors of the present invention have favorable pharmacokinetic profiles. Thus, the compounds are capable of derepressing fetal globin through HDAC inhibition. In a preferred embodiment, the compounds are able to treat sickle-cell disease or beta-thalessemia. Further, the compounds are able to treat a subject suffering from or susceptible to a hemoglobinopathy.

Inhibition of HDAC, including inhibition of HDAC1 and HDAC2 by selective compounds, can induce the expression of genes associated with synapse formation and memory in cultured neurons. In addition, inhibition of HDAC2 by gene disruption can lead to the formation of new synapses and increase cognitive performance in mice. Inhibition of HDAC6 by selective molecules can reverse the effects of neurodegenerative transgenes in mice, including amyloid precursor protein and presenelin 1. The selective inhibitors of HDAC1, HDAC2 and HDAC6 of the present invention would be capable of enhancing synapse formation and reversing the effects of amyloid protein, thus lessening the symptoms of neurodegenerative diseases such as Alzheimer's disease by two complimentary mechanisms.

In another aspect, the invention provides a method of activating latent HIV in a subject comprising administering to the subject a compound of Formula I, Formula II, Formula III, or any of the compounds presented in Table 1. The same compounds can be used treat HIV infections. In another embodiment, the compounds can be used in combination with one or more anti-retroviral agents for the treatment of HIV infections. In an embodiment, the HIV infection is HIV-1.

Anti-retroviral agents that can be used in combination with the HDAC inhibitors of the instant invention include nucleoside reverse transcriptase inhibitors, non-nucleoside reverse transcriptase inhibitors, protease inhibitors, virus uptake/adsorption inhibitors, virus receptor antagonists, viral fusion inhibitors, viral integrase inhibitors, entry inhibitor, co-receptor antagonist, cyclin dependent kinase inhibitor, and transcription inhibitors or other anti-retroviral agents used in treatment of HIV infection. Preferred anti-retroviral agents include efavirenz, indinavir sulfate, and raltegravir potassium As discussed above, the present invention provides compounds useful for the treatment of various diseases. In certain embodiments, the compounds of the present invention are useful as inhibitors of histone deacetylases (HDACs) and thus are useful as anti-cancer agents, and thus may be useful in the treatment of cancer, by effecting tumor cell death or inhibiting the growth of tumor cells. The compounds of the invention are capable of inducing apoptosis in cancer cells thereby able to treat a disease such as a cancer or proliferation disease.

In certain embodiments, the cancer is lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In some embodiments, the cancer is lung cancer, colon cancer, breast cancer, neuroblastoma, leukemia, or lymphomas. In a further embodiment, the cancer is non-small cell lung cancer (NSCLC) or small cell lung cancer.

In further embodiments, the cancer is a hematologic cancer, such as a leukemia or a lymphoma. In a certain embodiment, the lymphoma is Hodgkins lymphoma or Non Hodgkin's lymphoma. In certain embodiments, the inventive compounds are effective anticancer agents, which are active against leukemia cells and thus are useful for the treatment of leukemias, e.g., myeloid, lymphocytic, myelocytic and lymphoblastic leukemias.

In another aspect, the present invention provides for a method of treating a subject suffering from or susceptible to Hodgkins lymphoma or Non Hodgkin's lymphoma comprising administering to a subject in need thereof a therapeutically effective amount of a compound of the instant invention to thereby treat the subject suffering from or susceptible to Hodgkins lymphoma or Non Hodgkin's lymphoma.

In various embodiments, the invention provides a method of treating cancer in a subject further comprising co-administering one or more of a chemotherapeutic agent, radiation agent, hormonal agent, biological agent or an anti-inflammatory agent to the subject. In some embodiments the chemotherapeutic agent is azacitidine, decitabine, clofarabine, erlotinib, bortezomib, carfilzomib, ixazomib, tamoxifen, trastuzumab, raloxifene, doxorubicin, lenalidomide, pomalidomide, fluorouracil/5-fu, pamidronate disodium, anastrozole, exemestane, cyclophosphamide, epirubicin, letrozole, toremifene, fulvestrant, fluoxymesterone, methotrexate, megastrol acetate, docetaxel, paclitaxel, testolactone, aziridine, vinblastine, capecitabine, goselerin acetate, zoledronic acid, taxol, vinblastine, or vincristine.

In another embodiment, the chemotherapeutic agent is an aromatase inhibitor.

In an embodiment, the biological agent is rituximab, ipilimumab, bevacizumab, cetuximab, panitumumab, trastuzumab, or other monoclonal antibodies used for the treatment of cancer.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Also, as discussed above, the compounds of the invention are selective inhibitors of HDAC1, HDAC2, and/or HDAC6 and, as such, are useful in the treatment of disorders modulated by these histone deacetylases (HDACs). For example, compounds of the invention may be useful in the treatment of cancer (e.g., lung cancer, colon cancer, breast cancer, neuroblastoma, leukemia, or lymphomas, etc.). Accordingly, in yet another aspect, according to the methods of treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of an inventive compound (i.e., of any of the formulae herein), as described herein, to a subject in need thereof. In certain embodiments, the subject is identified as in need of such treatment. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer and other proliferative disorders including, but not limited to lung cancer (e.g. non-small cell lung cancer), colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, leukemia (e.g., CML, AML, CLL, ALL), lymphomas (non-Hodgkin's and Hodgkin's), myelomas, retinoblastoma, cervical cancer, melanoma and/or skin cancer, bladder cancer, uterine cancer, testicular cancer, esophageal cancer, and solid tumors.

Provided in some embodiments are methods for inhibiting migration of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for inducing maturation of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for altering cell cycle progression of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for decreasing viability and survival of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for inducing differentiation of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for enhancing low-concentration ATRA treatment of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for inducing cell cycle arrest of a neuroblastoma cell comprising administering to the cell a therapeutically effective amount of a HDAC1, HDAC2, and/or HDAC6 selective inhibitor or a pharmaceutically acceptable salt thereof. The HDAC1, HDAC2, and/or HDAC6 selective inhibitor can be any compound selected from the group consisting of a compound of Formula I, Formula II, Formula III, any of the compounds presented in Table 1, Compound X, and Compound Y.

Provided in some embodiments are methods for treating neuroblastoma in a subject comprising administering to the subject a therapeutically effective amount of Compound 001, Compound X, or Compound Y.

In certain embodiments, the invention provides a method of treatment of any of the disorders described herein, wherein the subject is a human.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substitutents, derivatives, formulations and/or methods of the invention may be made without departing from the spirit of the invention and the scope of the appended claims. Definitions of the variables in the structures in the schemes herein are commensurate with those of corresponding positions in the formulae presented herein.

Example 1

Synthesis of 2-((1-acetyl-4-phenylpiperidin-4-yl)amino)-N-hydroxypyrimidine-5-carboxamide (Compound 003)

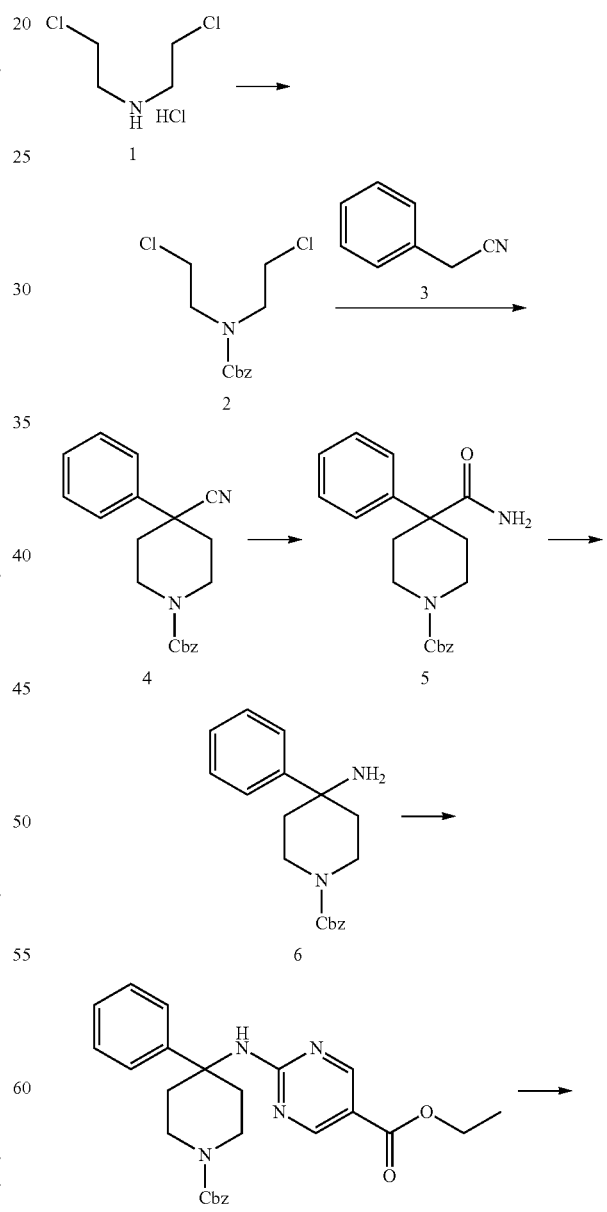

-continued

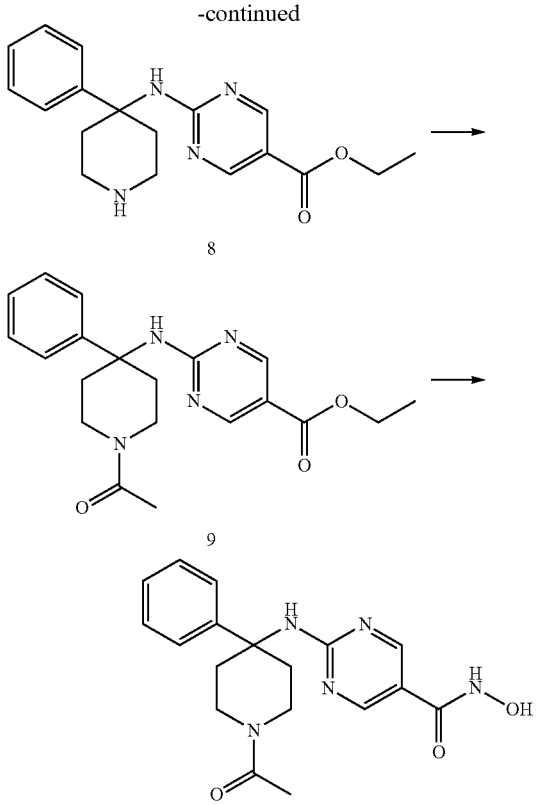

Step 1:
To a solution of 1 (10.4 g, 56.5 mmol) and TEA (11.4 g, 113 mmol) in DCM (60 mL) was added dropwise CbzCl (10 g, 56.5 mmol) over 30 mins at 0° C. Then the mixture was stirred at room temperature (r.t.) for 6 hrs. $H_2O$ (50 ml) was added, the organic layer was washed with aqueous NaCl, dried by anhydrous $Na_2SO_4$, concentrated in vacuo and the residue was purified by silica gel chromatography (PE/EA=20:1) to afford compound 2 as a white solid (11.6 g, yield: 70%).

Step 2:
To a flask containing compound 3 (1.52 g, 13.1 mmol) and compound 2 (3 g, 10.9 mol) in DMF (25 ml) was added NaH (1.09 g, 27.2 mmol) at 0° C. It was stirred at 60° C. for 3 hrs. $H_2O$ was added, the resulting mixture was extracted with ethyl acetate (EA). The combined EA layers were concentrated in vacuo and the residue was purified by silica gel chromatography (PE/EA=2:1) to afford compound 4 as a yellow solid (1.9 g, yield: 54%).

Step 3:
To a mixture of compound 4 (1.89 g, 5.91 mmol) in DMSO (15 mL) was added $K_2CO_3$ (2.4 g, 17.7 mmol), the mixture was stirred at 60° C. Then to the reaction 30% $H_2O_2$ (17 ml, 177 mmol) was added dropwise. After the reaction was complete, $H_2O$ was added, and the reaction mixture was filtered. The resulting white solid was dried to afford compound 5 1.99 g, yield: 70%).

Step 4:
A mixture of compound 5 (6.2 g, 18.3 mmol), NaClO (11 ml, 25.6 mol), and 3N NaOH (17 mL, 51.3 mmol) in t-BuOH (40 mL) was stirred at 0° C. to r.t. overnight. The mixture was concentrated, extracted with EA (30 mL×2), washed with aqueous NaCl, dried by $Na_2SO_4$, and concentrated to afford compound 6 (4.5 g, yield: 80%).

Step 5:
To a solution of compound 6 (2.0 g, 6.45 mmol) in Dioxane (18 mL) was added ethyl 2-chloropyrimidine-5-carboxylate (1.08 g, 5.80 mmol), N,N-Diisopropylethylamine (DIPEA) (1.7 g, 12.9 mmol) at 105° C. The reaction was stirred overnight. The reaction mixture was concentrated in vacuo, and the residue was purified by silica gel chromatography (PE/EA=6:1) to give compound 7 (1.5 g, yield: 51%).

Step 6:
HBr/AcOH (6.0 mL) was added to a flask containing compound 7 (3.0 g, 6.52 mmol) at r.t. for 3 hrs. Then 12 ml $Et_2O$ was added, the reaction mixture filtered, the solid was dried to give compound 8 (1.85 g, yield: 70%) as a yellow solid.

Step 7:
To a solution of compound 8 (100 mg, 0.31 mmol) in DCM (4 mL) was added $Ac_2O$ (47 mg, 0.46 mmol), and $Et_3N$ (0.5 ml) at r.t. The reaction was stirred for 2 hrs and the reaction mixture was concentrated in vacuo to give compound 9 (120 g, yield: 100%).

Step 8:
To a solution of compound 9 (20 mg, 0.33 mmol) in MeOH (2 mL) and DCM (1 ml) at 0° C. was added $NH_2OH$ (0.4 ml) and stirred for 10 mins. Then NaOH/MeOH (0.8 ml) was added and the reaction was stirred for 2 hrs. The mixture was concentrated, adjusted to a pH=5 using 2N HCl, extracted with EA (10 ml) and purified by Pre-HPLC to afford 2-((1-acetyl-4-phenylpiperidin-4-yl)amino)-N-hydroxypyrimidine-5-carboxamide (18 mg, 16%). $^1$H NMR (500 MHz, DMSO): δ 10.95 (s, 1H), 8.98 (s, 1H), 8.62 (s, 1H), 8.33 (s, 1H), 8.23 (s, 1H), 7.38 (d, J=7.6 Hz, 2H), 7.27 (t, J=7.7 Hz, 2H), 7.16 (t, J=7.3 Hz, 1H), 4.28 (d, J=13.2 Hz, 1H), 3.72 (d, J=13.6 Hz, 1H), 3.39-3.28 (m, 1H), 2.85 (t, J=12.3 Hz, 1H), 2.61 (t, J=12.5 Hz, 2H), 2.01 (s, 3H), 1.97-1.86 (m, 1H), 1.77 (t, J=11.0 Hz, 1H). LCMS: m/z=356 (M+H)$^+$ Example 2

Synthesis of benzyl 4-((5-(hydroxycarbamoyl)pyrimidin-2-yl)amino)-4-phenylpiperidine-1-carboxylate (Compound 002)

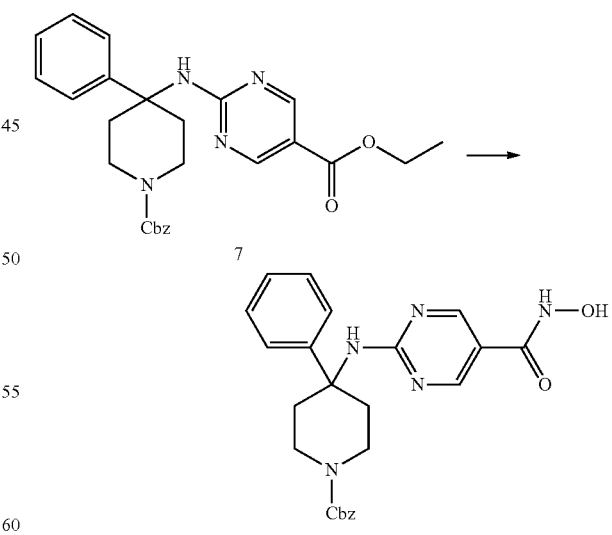

To a solution of compound 7 (460 mg, 1.0 mmol) in MeOH (10 mL) and DCM (3 ml) at 0° C. was added $NH_2OH$ (1.0 ml) and stirred for 10 mins. NaOH/MeOH (2.0 ml) was added and the reaction was stirred for 2 hrs. The mixture was concentrated, adjusted to pH=5 using 2N HCl, extracted with EA (10 ml), washed with aqueous NaCl, dried by $Na_2SO_4$, and concentrated to afford benzyl 4-((5-(hydroxycarbamoyl)pyrimidin-2-yl)amino)-4-phenylpiperidine-1-carboxylate (400 mg, 89%). ¹H NMR (500 MHz, DMSO) δ 10.94 (s, 1H), 8.97 (s, 1H), 8.61 (s, 1H), 8.34 (s, 1H), 8.21 (s, 1H), 7.40-7.35 (m, 6H), 7.32 (dt, J=9.1, 4.5 Hz, 1H), 7.26 (t, J=7.7 Hz, 2H), 7.15 (t, J=7.3 Hz, 1H), 5.08 (s, 2H), 3.92 (d, J=13.1 Hz, 2H), 3.15 (m, 2H), 2.60 (s, 2H), 1.87 (dd, J=12.8, 9.1 Hz, 2H). LCMS: m/z=448 (M+H)⁺

Example 3

Synthesis of N-hydroxy-2-((4-phenyl-1-(phenylcarbamoyl)piperidin-4-yl)amino)pyrimidine-5-carboxamide (Compound 001)

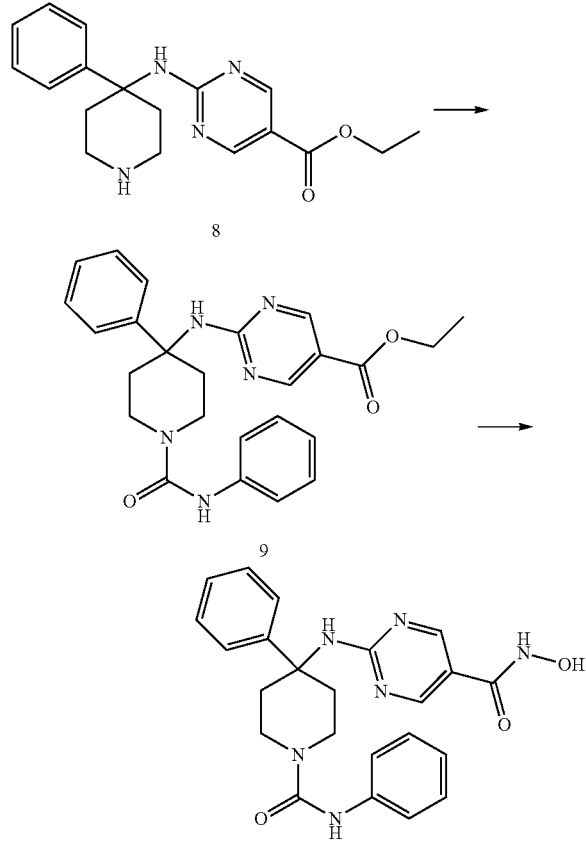

Step 1:
To a solution of compound 8 (85 mg, 0.26 mmol) in THF (4 mL) was added isocyanatobenzene (46 mg, 0.39 mmol), DIPEA (0.2 ml) at r.t. The reaction was stirred for 2 hrs. and subsequently concentrated in vacuo to give compound 9 (80 g, yield: 69%).

Step 2:
To a solution of compound 9 (80 mg, 0.18 mmol) in MeOH (3 mL) and DCM (1 ml) at 0° C. was added NH₂OH (0.2 ml). The reaction was stirred for 10 mins, at which time NaOH/MeOH (0.4 ml) was added. The reaction was stirred for 2 hrs. The resulting reaction mixture was concentrated, adjusted to PH=5 using 2N HCl, extracted with EA (10 ml), and purified by Pre-HPLC to afford N-hydroxy-2-((4-phenyl-1-(phenylcarbamoyl)piperidin-4-yl)amino)pyrimidine-5-carboxamide (14 mg, 17%). ¹H NMR (500 MHz, DMSO) δ 10.83 (s, 1H), 8.96 (s, 1H), 8.60 (s, 1H), 8.49 (s, 2H), 8.37 (s, 1H), 8.20 (s, 1H), 7.47-7.46 (d, J=7.6 Hz, 2H), 7.41-7.39 (d, J=7.4 Hz, 2H), 7.29-7.26 (t, J=7.7 Hz, 2H), 7.23-7.20 (m, J=7.7 Hz, 2H), 7.18-7.15 (t, J=7.3 Hz, 1H), 6.92 (t, J=7.3 Hz, 1H), 4.03 (d, J=13.2 Hz, 2H), 3.13 (t, J=12.1 Hz, 2H), 2.64 (d, J=13.0 Hz, 2H), 1.90 (t, J=11.0 Hz, 2H). LCMS: m/z=433 (M+H)⁺

Example 4

Synthesis of ethyl 4-((5-(hydroxycarbamoyl)pyrimidin-2-yl)amino)-4-phenylpiperidine-1-carboxylate (Compound 004)

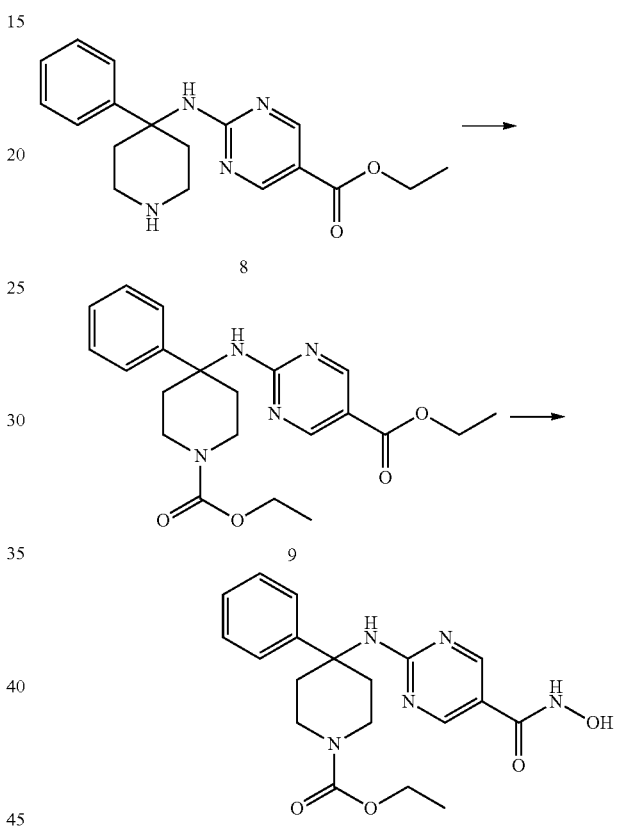

Step 1:
To a solution of compound 8 (106 mg, 1.0 mmol), ethyl chloroformate (400 mg, 1.0 mmol) in 5 ml THF was added DIPEA (252 mg, 2.0 mmol). The mixture was stirred at r.t. for 4 hrs. LCMS monitored the reaction to completion. Upon completion, the reaction mixture was concentrated and the residue was purified by flash chromatography with PE/EA from 6:1 to 5:1 to give the target compound, compound 9 (320 mg, 82%).

Step 2:
To a solution of compound 9 (300 mg, 0.8 mmol) in 5 ml CH₃OH/CH₂Cl₂ was added NH₂OH (0.8 ml) dropwise at 0° C. The reaction was then stirred for 10 min. at 0° C. NaOH/CH₃OH was added into the solution slowly and the reaction continued stirring at 0° C. for 2 hrs. After the pH of the solution was adjusted to 6 by using conc. HCl, the target compound was precipitated from the solution as a white solid, washed by the mixing solvent of EA and PE to give ethyl 4-((5-(hydroxycarbamoyl)pyrimidin-2-yl)amino)-4-phenylpiperidine-1-carboxylate as a white solid (200 mg, 65%). ¹H NMR (500 MHz, DMSO) δ 10.93 (s, 1H), 8.95 (s, 1H), 8.60 (s, 1H), 8.34 (s, 1H), 8.17 (s, 1H), 7.38 (d, J=7.7 Hz, 2H), 7.26 (t, J=7.7 Hz, 2H), 7.15 (t, J=7.2 Hz, 1H), 4.07-4.00 (m, 2H), 3.88 (d, J=11.1 Hz, 2H), 3.11 (s, 2H), 2.60 (d, J=12.6 Hz, 2H), 1.86 (td, J=13.1, 4.3 Hz, 2H), 1.20-1.17 (m, 3 nH). LCMS: m/z=386 (M+H)+

Example 5

Synthesis of 2-((1-acetyl-4-isopropylpiperidin-4-yl) amino)-N-hydroxypyrimidine-5-carboxamide (Compound 005)

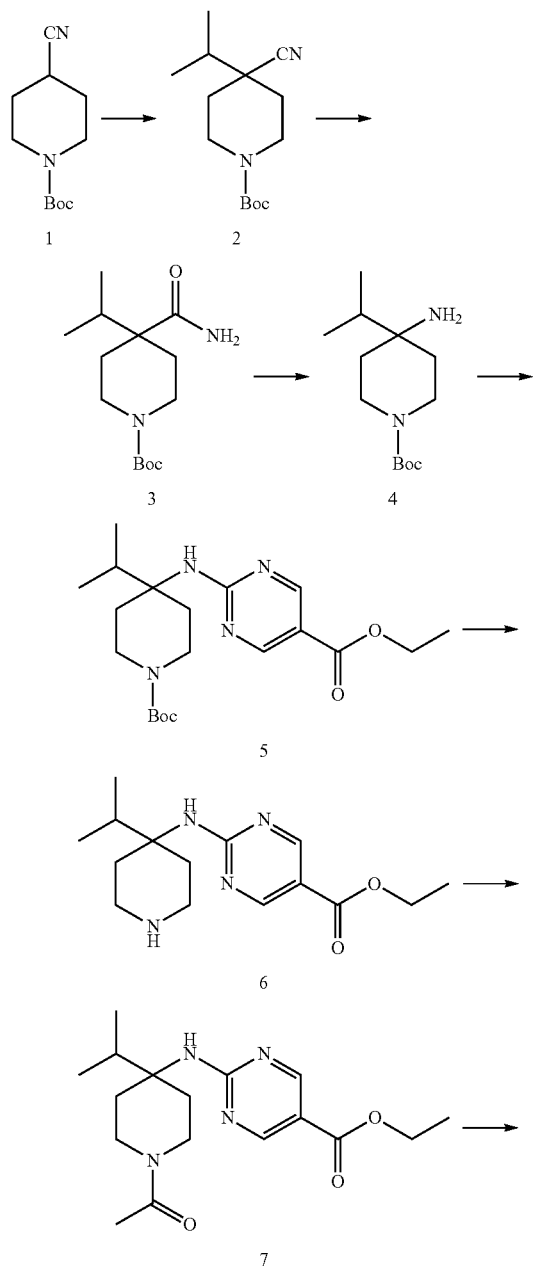

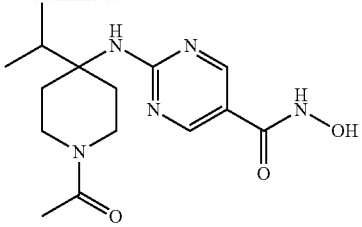

Step 1:
To a solution of compound 1 (3 g, 14.28 mmol) in a 3-neck-flask flushed with $N_2$ was added lithium bis(trimethylsilyl) amide (LiHDMS) (1M, 21.4 ml) at −78° C. The reaction was stirred for 3 h at which time 2-iodopropane (3.6 g, 21.43 mmol) was added slowly. The reaction solution was stirred at −78° C., and then warmed to r.t. overnight. The mixture was quenched with $H_2O$ (2 ml), concentrated, dissolved in EA (200 ml), and washed with water (100 ml×2) and saturated NaCl (aq, 100 ml). The organic layer was concentrated to afford compound 2 as a brown solid (4 g, 100%).

Step 2:
To a solution of compound 2 (1 g, 3.97 mmol) in DMSO (30 ml) was added $K_2CO_3$ (1.6 g, 11.9 mmol) stirred at 60° C. Over a period of 2 hrs, $H_2O_2$ (30% aq., 5 ml) was added dropwise. TLC was used to monitor completion of the reaction. EA (100 ml) was added to the reaction mixture and subsequently washed with water (50 ml×2) and saturated NaCl (aq, 50 ml). The combined organic solutions were dried with anhydrous $Na_2SO_4$. The solvent was removed in vacuo to obtain compound 3 as a white solid (1 g, 90%).

Step 3:
To a solution of compound 3 (2.7 g, 10 mmol) in acetonitrile (AN) (50 ml) was added KOH (4N, aq., 50 ml) and 1,3-dibromo-5,5-dimethylhydantoin (DBDMH) (2.81 g, 5 mmol) at 0° C. The reaction was stirred at r.t. overnight. The mixture was concentrated and 1N HCl was added to adjust the pH to ~6. The resulting mixture was extracted with EA (50 ml). The aqueous phase was then adjusted to pH~9 by addition of KOH, and was subsequently extracted with EA (50 ml×3). The EA phase was dried with anhydrous $Na_2SO_4$ and the solvent was concentrated to obtain compound 4 as a colorless liquid (1 g, 40%).

Step 4:
A solution of compound 4 (500 mg, 2.06 mmol) and ethyl 2-chloropyrimidine-5-carboxylate (384 mg, 2.06 mmol) in N-methyl-2-pyrrolidone (NMP) (10 ml) flushed with $N_2$ was stirred at 140° C. for 1 hour. EA (100 ml) was added to the reaction and resulting mixture was washed with water (50 ml×2) and saturated NaCl (aq, 50 ml). The resulting organic solution was concentrated and purified by silica gel chromatography column (PE/EA=5/1) to obtain compound 5 as a white solid (120 mg 15%).

Step 5:
To a solution of compound 5 (200 mg, 0.51 mmol) in DCM (5 ml) was added TFA (2 ml). The reaction was stirred at r.t. for 30 min. The mixture was concentrated to obtain compound 6 as a brown liquid (200 mg, 90%).

Step 6:
To a solution of compound 6 (200 mg, 0.709 mmol) in DCM was added $Et_3N$ (214 mg, 2.13 mmol) and acetyl chloride (56 mg, 0.709 mmol) at 0° C. The reaction stirred for 1 hour at which time the reaction mixture was concentrated to obtain the compound 7 as a brown liquid (220 mg, 95%)

Step 7:

To a solution of 7 (220 mg) in MeOH (2 ml) was added NH$_2$OH (50% aq, 2 ml) and NaOH (saturated in MeOH 2 ml) at 0° C. The reaction stirred for 1 hour. The reaction mixture was then adjusted to a pH of ~7 with 4N HCl (aq.), concentrated in vacuo, and purified by Pre-HPLC to obtain compound 8 as a white solid (68 mg, 35%). $^1$H NMR (500 MHz, DMSO): δ 10.97 (s, 1H), 8.57 (s, 2H), 7.44 (s, 1H), 4.28-4.20 (m, 1H), 3.69-3.58 (m, 1H), 3.21-3.06 (m, 1H), 2.66-2.57 (m, 1H), 2.57-2.53 (m, 1H), 2.42-2.24 (m, 2H), 1.97 (s, 3H), 1.57-1.45 (m, 1H), 1.41-1.28 (m, 1H), 0.82 (d, J=6.9 Hz, 6H). LCMS: m/z=322 (M+H)$^+$ Example 6

Synthesis of ethyl 4-((5-(hydroxycarbamoyl)pyrimidin-2-yl)amino)-4-isopropylpiperidine-1-carboxylate (Compound 006)

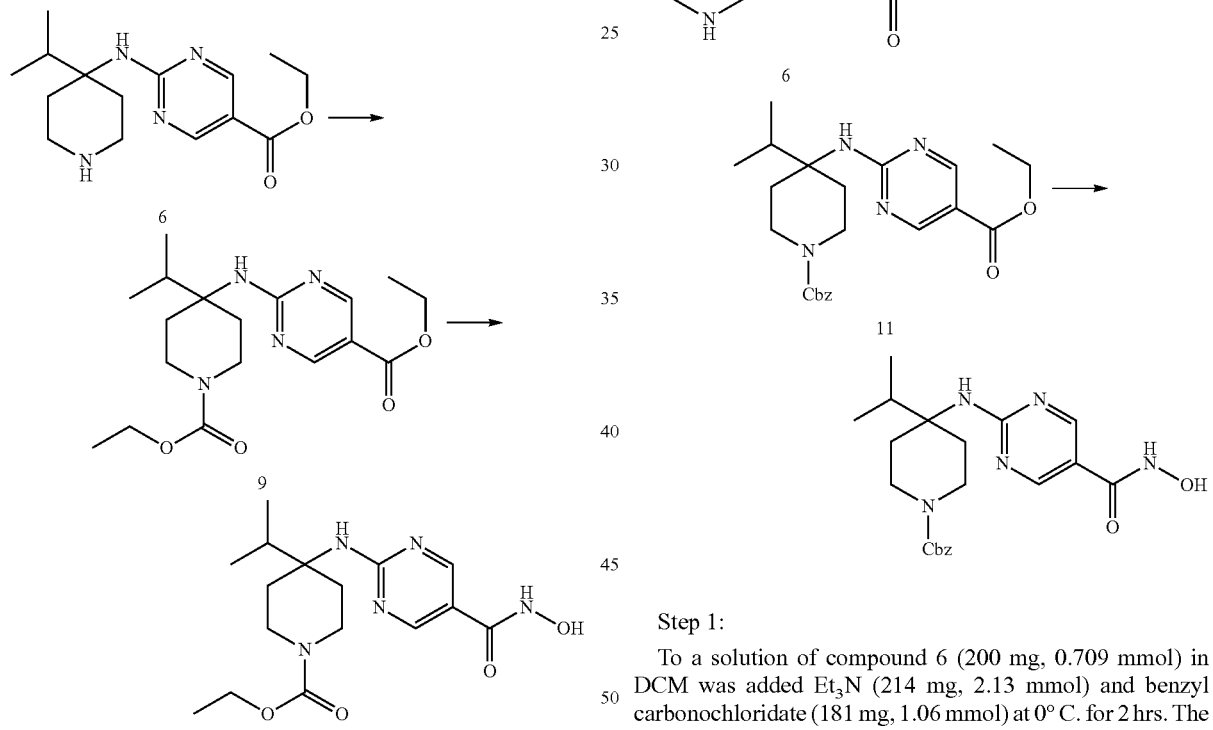

Step 1:

To a solution of compound 6 (200 mg, 0.709 mmol) in DCM was added Et$_3$N (214 mg, 2.13 mmol) and ethyl carbonochloridate (77 mg, 0.709 mmol) at 0° C. for 1 hour. The reaction mixture was concentrated to obtain compound 9 as a brown liquid (250 mg, 95%).

Step 2:

To a solution of compound 9 (250 mg) in MeOH (2 ml) was added NH$_2$OH (50% aq., 2 ml) and NaOH (saturated in MeOH, 2 ml) at 0° C. The mixture was stirred for 1 hour after which the reaction solution was adjusted to a pH of ~7 with 4N HCl (aq.), concentrated, and purified by Pre-HPLC to obtain ethyl 4-((5-(hydroxycarbamoyl)pyrimidin-2-yl)amino)-4-isopropylpiperidine-1-carboxylate as a white solid (67 mg, 30%). $^1$H NMR (500 MHz, DMSO): δ 10.95 (m, 1H), 8.97 (m, 1H), 8.57 (s, 2H), 7.40 (s, 1H), 4.01 (d, J=7.1 Hz, 2H), 3.89-3.73 (m, 2H), 3.53-3.23 (m, 2H), 3.02-2.78 (m, 2H), 2.60-2.52 (m, 1H), 2.40-2.26 (m, 2H), 1.44 (d, J=4.4 Hz, 2H), 1.16 (t, J=7.1 Hz, 3H), 0.82 (d, J=6.9 Hz, 6H). LCMS: m/z=352 (M+H)$^+$ Example 7

Synthesis of benzyl 4-((5-(hydroxycarbamoyl)pyrimidin-2-yl)amino)-4-isopropylpiperidine-1-carboxylate (Compound 007)

Step 1:

To a solution of compound 6 (200 mg, 0.709 mmol) in DCM was added Et$_3$N (214 mg, 2.13 mmol) and benzyl carbonochloridate (181 mg, 1.06 mmol) at 0° C. for 2 hrs. The mixture was concentrated to obtain compound 11 as a brown liquid (300 mg, 95%).

Step 2:

To a solution of compound 11 (300 mg) in MeOH (2 ml) was added NH$_2$OH (50% aq, 2 ml) and NaOH (saturated in MeOH, 2 ml) at 0° C. The mixture stirred for 1 hour after which the reaction solution was adjusted to a pH of ~7 with 4N HCl (aq.), concentrated, and purified by Pre-HPLC to obtain benzyl 4-((5-(hydroxycarbamoyl)pyrimidin-2-yl) amino)-4-isopropylpiperidine-1-carboxylate as a white solid (78.1 mg, 28%). $^1$H NMR (500 MHz, DMSO) 610.99 (m, 1H), 8.57 (m, 2H), 7.53-7.26 (m, 6H), 5.06 (s, 2H), 3.94-3.72 (m, 2H), 3.07-2.77 (m, 2H), 2.61-2.53 (m, 1H), 2.42-2.24 (m, 2H), 1.59-1.29 (m, 2H), 0.81 (d, J=6.8 Hz, 6H). LCMS: m/z=414 (M+H)$^+$.

Example 8

Synthesis of N-hydroxy-2-((1-((4-methoxyphenyl)carbamoyl)-4-phenylpiperidin-4-yl)amino)pyrimidine-5-carboxamide (Compound 008)

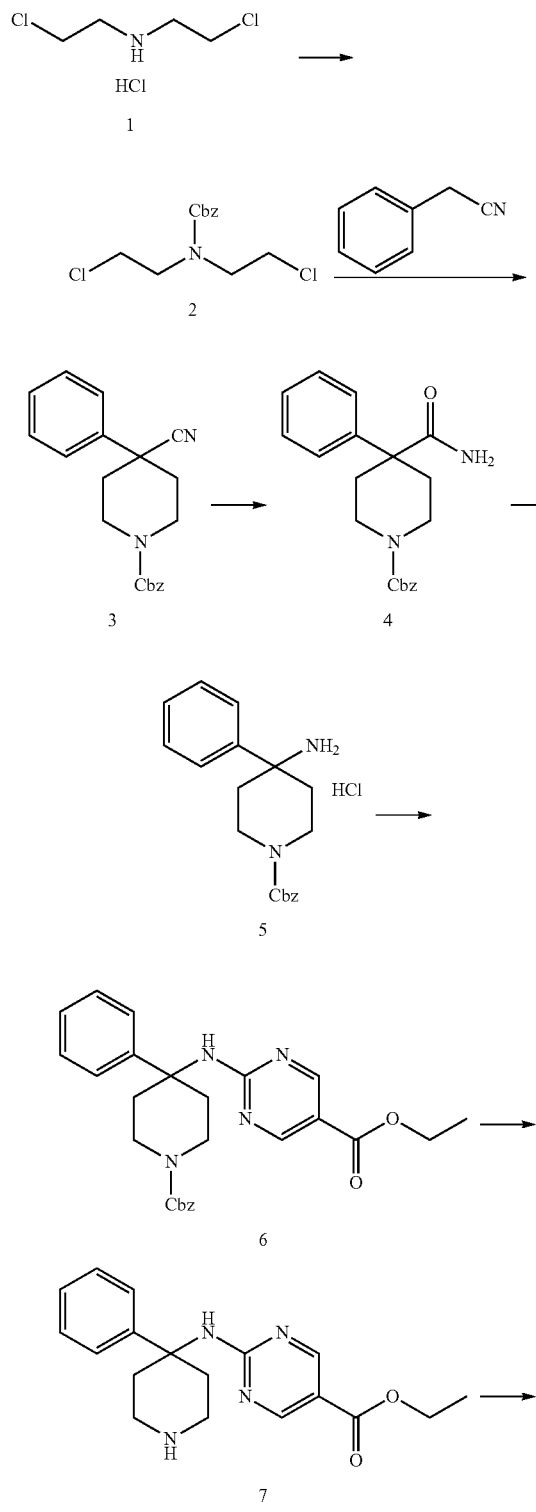

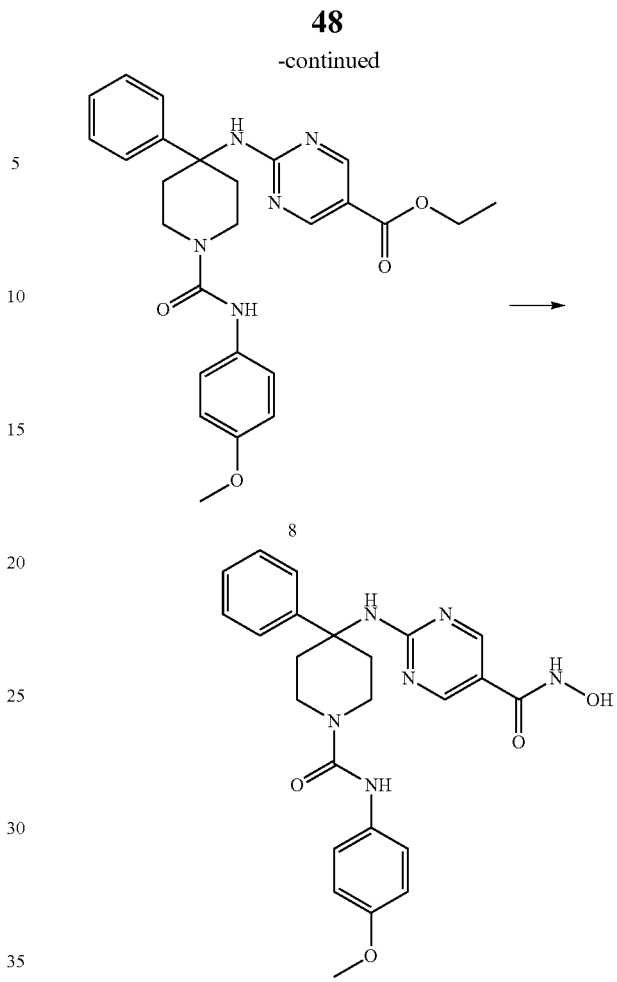

Step 1:

To a solution of compound 1 (10 g, 56.5 mmol) in DCM (50 mL) was added TEA (11.4 g, 113 mmol), followed by CbzCl (10.4 g, 56.5 mmol) while the system was in a water bath. The mixture was stirred for 3 hrs at r.t. Water (50 ml) was added to the reaction mixture and extracted with EA (150 ml×2). The organic phase was washed with saturated salt and dried over $Na_2SO_4$. Concentration and purification by silica gel column with EA/PE=1/20 yielded compound 2 (3 g, 18%) as an oil.

Step 2:

To a solution of compound 2 (100 g, 0.36 mol) and benzyl cyanide (59 g, 0.43 mol) in DMF (400 ml) was added NaH (37 g, 0.94 mol) at 0° C. After increasing the temperature to 60° C., the mixture was stirred at 60° C. overnight. TLC was used to monitor the reaction to completion. After cooling, water was added into the mixture resulting in a green solid. The target compound was purified by flash chromatography with PE/EA from 30:1 to 2:1 to yield compound 3 (38 g, 79%) as a white solid.

Step 3:

To a solution of compound 3 (38 g, 112 mmol) in 300 ml DMSO was added 30% $H_2O_2$ (190 ml, 2248 mmol) slowly at 0° C. followed by stirring for 30 mins. Then the temperature was slowly increased to 40° C. and stirred for an additional 30 mins. After increasing the temperature to 60° C., the mixture was stirred at 60° C. overnight. TLC was used to monitor the reaction to completion. After cooling, water was added into the mixture to give a white solid, which was isolated by filtration (38 g, ~95%).

Step 4:

To a solution of compound 4 (38 g, 106 mmol) in 400 ml BuOH was slowly added NaClO (64.2 ml, 149 mmol) followed by 3N NaOH (99 ml, 298 mmol) at 0° C. Then the mixture was stirred at r.t. overnight. TLC was used to monitor the reaction to completion. The mixture was concentrated and extracted with EtOAc. The organic layer was separated, washed and dried. Then the mixture was dissolved in Et$_2$O, and the pH was adjusted to 2 using HCl/Dioxane. The precipitate was collected, yielding the target compound 5 (38 g 100%).

Step 5:

To a solution of compound 5 (9.6 g, 26 mmol), 2-Cl-pyrimidine (4.9 g, 26 mmol) in 150 ml 1,4-Dioxane was added DIPEA (7.7 g, 60 mmol). The mixture was stirred at 110° C. overnight. LCMS was used to monitor the reaction to completion. Water (50 ml) was added and the mixture was extracted with EtOAc. The combined organic extracts were washed and dried. The target compound 6 (11 g, 90%) was purified by flash chromatography with PE/EA from 30:1 to 2:1.

Step 6:

To a solution of compound 6 (1 g, 2.17 mmol) in MeOH (15 mL) was added Pd/C (0.1 g, 10% wq) under N$_2$. The reaction was stirred under an H$_2$ atmosphere overnight, after which it was filtered through celite and washed with MeOH. Concentration yielded compound 7 (690 mg, 98%) as a light yellow solid.

Step 7:

To a mixture of compound 7 (81 mg, 0.2 mmol) and 1-isocyanato-4-methoxybenzene (21 mg, 0.2 mmol) in THF (4 ml) was added DIPEA (46 mg, 0.36 mmol). The reaction was stirred for 1 h. at r.t., concentrated, and purified by gel chromatography (DCM:MeOH=10:1) to afford 8 (80 mg, 84%) as a white solid.

Step 8:

To a solution of compound 8 (80 mg, 0.16 mmol) in MeOH (3 mL) and DCM (1 ml) at 0° C. was added NH$_2$OH (0.2 ml) followed by stirring for 10 min. Then NaOH/MeOH (0.4 ml) was added and the reaction was stirred for 2 h. The reaction was concentrated and the pH was adjusted to 5, after which it was extracted with EA (10 ml). Purification by Pre-HPLC afforded the desired product, Compound 008 (15 mg, 21%). $^1$H NMR (500 MHz, DMSO) δ 8.60 (s, 1H), 8.32 (s, 2H), 8.19 (s, 1H), 7.40 (d, J=7.5 Hz, 2H), 7.34 (d, J=9.0 Hz, 2H), 7.27 (t, J=7.7 Hz, 2H), 7.16 (t, J=7.3 Hz, 1H), 6.81 (d, J=9.0 Hz, 2H), 4.00 (d, J=13.4 Hz, 2H), 3.70 (s, 3H), 3.11 (t, J=12.2 Hz, 2H), 2.63 (d, J=12.3 Hz, 2H), 1.89 (t, J=11.1 Hz, 2H). LCMS: m/z=463 (M+H)$^+$.

Example 9

Synthesis of 2-((1,4-diphenylpiperidin-4-yl)amino)-N-hydroxypyrimidine-5-carboxamide (Compound 009)

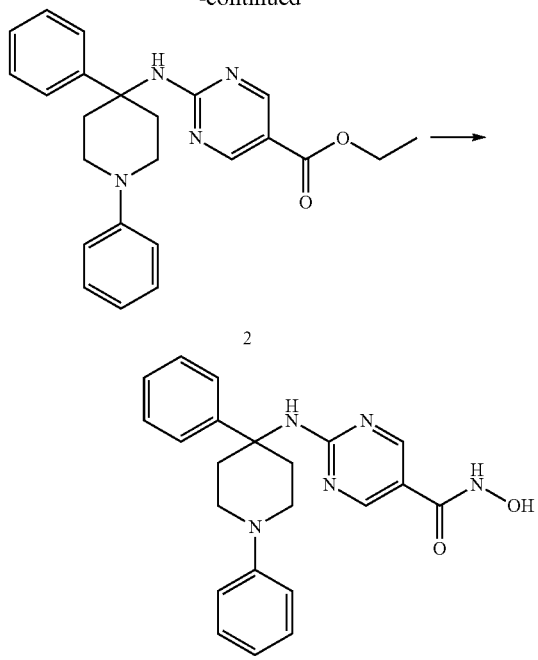

Step 1:

A mixture of compound 1 (200 mg, 0.49 mmol), bromobenzene (77 mg, 0.49 mmol), Pd$_2$(dba)$_3$ (20 mg, 0.02 mmol), Xantphos (12 mg, 0.02 mmol) and Cs$_2$CO$_3$ (480 mg, 1.47 mmol) in toluene (8 ml) was stirred at 95° C. overnight under N$_2$. After completion, the reaction was filtered and concentrated, and purified by gel chromatography (PE: EA=1:1) to afford compound 2 (60 mg, 20%) as a white solid.

Step 2:

To a solution of compound 2 (60 mg, 0.15 mmol) in MeOH (3 ml) and DCM (1 ml) at 0° C. was added NH$_2$OH (0.1 ml) followed by stirring for 10 mins. NaOH/MeOH (0.2 ml) was then added and stirred for 2 hrs. The reaction mixture was concentrated, adjusted to a pH of 5, and extracted with EA (10 ml). Purification by Prep-HPLC afforded the desired product, Compound 009 (18 mg, 32%). $^1$HNMR (500 MHz, DMSO) δ 10.77 (s, 1H), 8.96 (s, 1H), 8.47 (d, J=118.1 Hz, 2H), 8.14 (s, 1H), 7.43 (d, J=7.5 Hz, 2H), 7.28 (t, J=7.7 Hz, 2H), 7.22-7.14 (m, 3H), 6.96 (d, J=8.1 Hz, 2H), 6.74 (t, J=7.2 Hz, 1H), 3.58 (d, J=12.2 Hz, 2H), 2.98 (t, J=11.6 Hz, 2H), 2.72 (d, J=12.4 Hz, 2H), 2.09 (dd, J=12.4, 9.3 Hz, 2H). LCMS: m/z=390 (M+H)$^+$.

Example 10

Synthesis of 2-((1-((2-fluorophenyl)carbamoyl)-4-phenylpiperidin-4-yl)amino)-N-hydroxypyrimidine-5-carboxamide (Compound 010)

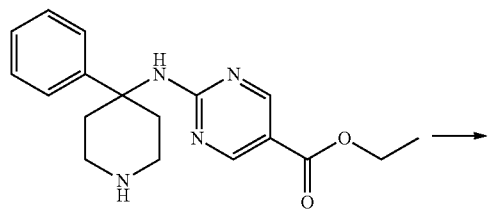

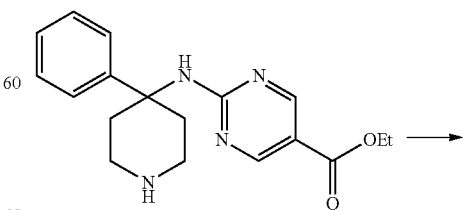

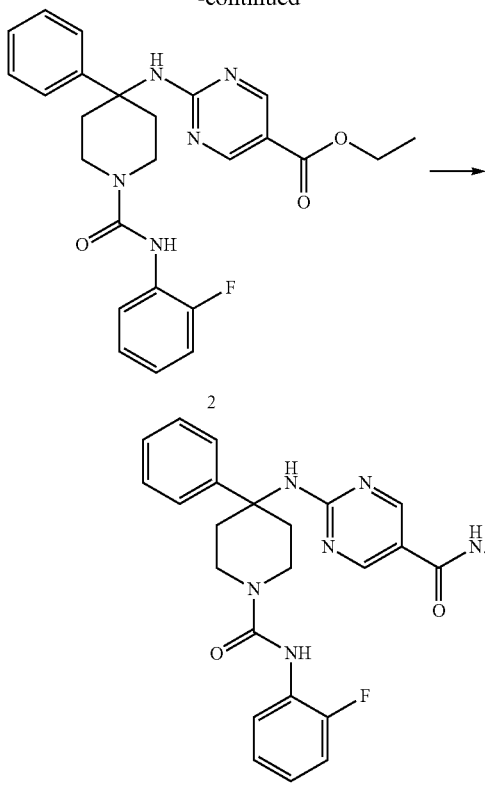

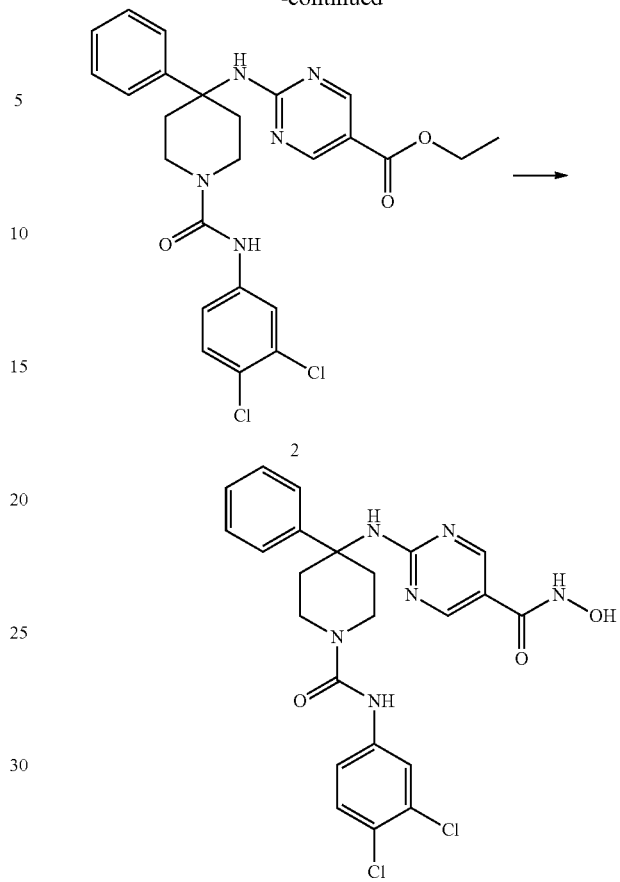

Step 1:

To a mixture of compound 1 (50 mg, 0.15 mmol) and 1-fluoro-2-isocyanatobenzene (21 mg, 0.15 mmol) in THF (4 ml) was added DIPEA (39 mg, 0.30 mmol) at r.t. followed by stirring for 1 hour. The reaction mixture was concentrated and purified by gel chromatography (PE:EA=1:1) to afford compound 2 (60 mg, 86%) as a white solid.

Step 2:

A procedure analogous to step 2 in Example 9 yielded Compound 010 (12 mg, 44%). $^1$H NMR (500 MHz, DMSO) δ 10.84 (s, 1H), 8.94 (s, 1H), 8.32 (d, J=59.2 Hz, 3H), 8.18 (s, 1H), 7.47-7.35 (m, 3H), 7.28 (t, J=7.7 Hz, 2H), 7.17 (dd, J=13.9, 6.5 Hz, 2H), 7.10 (dd, J=6.7, 2.9 Hz, 2H), 3.98 (d, J=13.0 Hz, 2H), 3.15 (t, J=12.3 Hz, 2H), 2.64 (d, J=12.4 Hz, 2H), 1.92 (t, J=10.9 Hz, 2H). LCMS: m/z=451 (M+H)$^+$.

Example 11

Synthesis of 2-((1-((3,4-dichlorophenyl)carbamoyl)-4-phenylpiperidin-4-yl)amino)-N-hydroxypyrimidine-5-carboxamide (Compound 011)

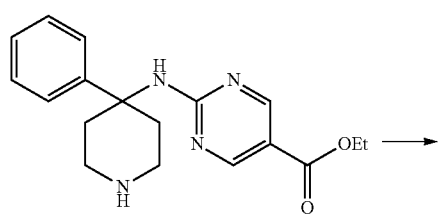

Step 1:

To a mixture of compound 1 (60 mg, 0.18 mmol) and 1,2-dichloro-4-isocyanatobenzene (34 mg, 0.18 mmol) in THF (4 ml) was added DIPEA (46 mg, 0.36 mmol) at r.t. followed by stirring for 1 hour. The reaction mixture was concentrated and purified by gel chromatography (PE:EA=1:1) to afford compound 2 (60 mg, 70%) as a white solid.

Step 2:

A procedure analogous to step 2 in Example 9 yielded Compound 011 (39 mg, 65%). $^1$H NMR (500 MHz, DMSO) δ 10.93 (s, 1H), 8.98 (s, 1H), 8.78 (s, 1H), 8.62 (s, 1H), 8.35 (s, 1H), 8.24 (s, 1H), 7.87 (s, 1H), 7.47 (s, 2H), 7.40 (d, J=7.6 Hz, 2H), 7.27 (t, J=7.7 Hz, 2H), 7.21-7.12 (m, 1H), 4.02 (d, J=12.9 Hz, 2H), 3.15 (t, J=12.4 Hz, 2H), 2.65 (d, J=12.5 Hz, 2H), 1.91 (t, J=10.8 Hz, 2H). LCMS: m/z=502 (M+H)$^+$.

Example 12

Synthesis of N-hydroxy-2-((1-(methyl(phenyl)carbamoyl)-4-phenylpiperidin-4-yl)amino)pyrimidine-5-carboxamide (Compound 012)

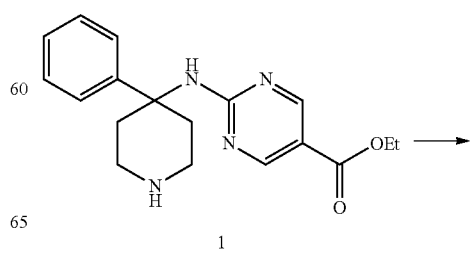

-continued

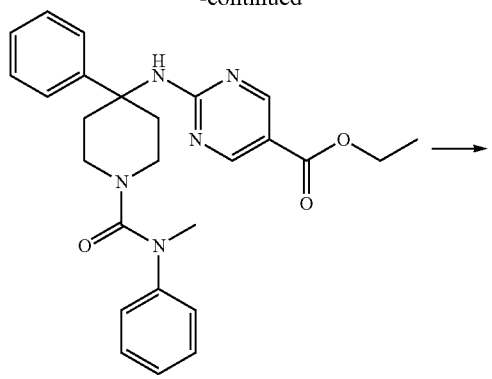

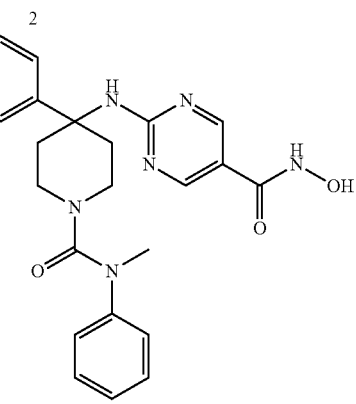

-continued

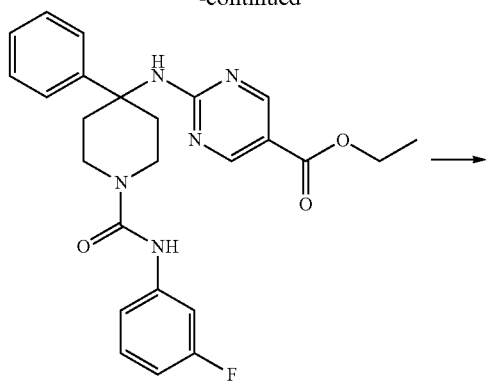

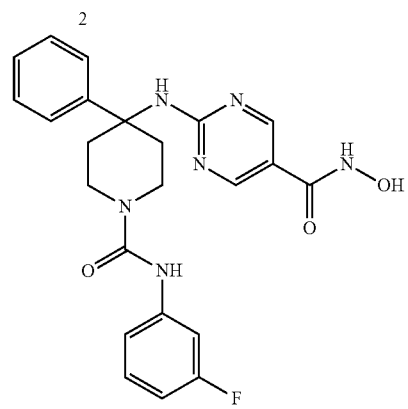

Step 1:

To a mixture of compound 1 (40 mg, 0.12 mmol) and methyl(phenyl)carbamic chloride (21 mg, 0.12 mmol) in THF (4 ml) was added DIPEA (31 mg, 0.24 mmol) at r.t. The reaction was stirred for 1 hr., concentrated, and purified by gel chromatography (PE:EA=1:1) to afford compound 2 (50 mg, 91%) as a white solid.

Step 2:

A procedure analogous to step 2 in Example 9 yielded Compound 012 (21 mg, 47%). $^1$H NMR (500 MHz, DMSO) δ 8.57 (s, 1H), 8.28 (s, 1H), 8.08 (s, 1H), 7.35 (t, J=7.9 Hz, 2H), 7.29 (d, J=7.5 Hz, 2H), 7.24 (t, J=7.7 Hz, 2H), 7.14 (d, J=7.6 Hz, 3H), 7.08 (d, J=7.4 Hz, 1H), 3.61 (d, J=13.4 Hz, 2H), 3.09 (s, 3H), 2.90 (t, J=12.3 Hz, 2H), 2.44 (d, J=12.7 Hz, 2H), 1.69 (t, J=10.9 Hz, 2H). LCMS: m/z=447 (M+H)$^+$.

Example 13

Synthesis of 2-((1-((3-fluorophenyl)carbamoyl)-4-phenylpiperidin-4-yl)amino)-N-hydroxypyrimidine-5-carboxamide (Compound 013)

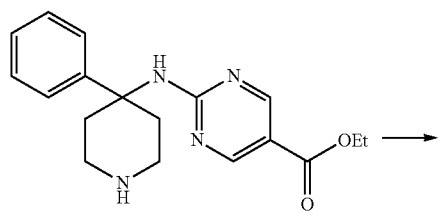

Step 1:

A mixture of compound 1 (60 mg, 0.18 mmol) and 1-fluoro-3-isocyanatobenzene (25 mg, 0.18 mmol) in THF (4 ml) was added DIPEA (46 mg, 0.36 mmol) at r.t. The reaction as stirred for 1 hr, concentrated, and purified by gel chromatography (PE:EA=1:1) to afford compound 2 (60 mg, 71%) as a white solid.

Step 2:

A procedure analogous to step 2 in Example 9 yielded Compound 013 (40 mg, 68%). $^1$H NMR (500 MHz, DMSO) δ 10.91 (s, 1H), 9.01 (s, 1H), 8.70 (s, 1H), 8.63 (s, 1H), 8.36 (s, 1H), 8.24 (s, 1H), 7.46 (d, J=12.3 Hz, 1H), 7.40 (d, J=7.6 Hz, 2H), 7.25 (dt, J=20.3, 7.8 Hz, 4H), 7.16 (t, J=7.3 Hz, 1H), 6.72 (t, J=7.6 Hz, 1H), 4.03 (d, J=13.4 Hz, 2H), 3.14 (t, J=12.2 Hz, 2H), 2.65 (d, J=12.7 Hz, 2H), 1.91 (t, J=10.9 Hz, 2H). LCMS: m/z=451 (M+H)$^+$.

Example 14

Synthesis of 2-((1-((4-fluorophenyl)carbamoyl)-4-phenylpiperidin-4-yl)amino)-N-hydroxypyrimidine-5-carboxamide (Compound 014)

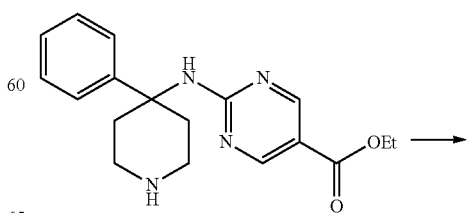

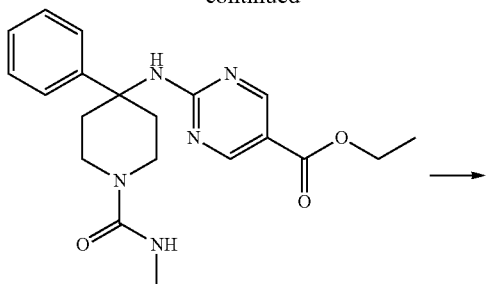

2

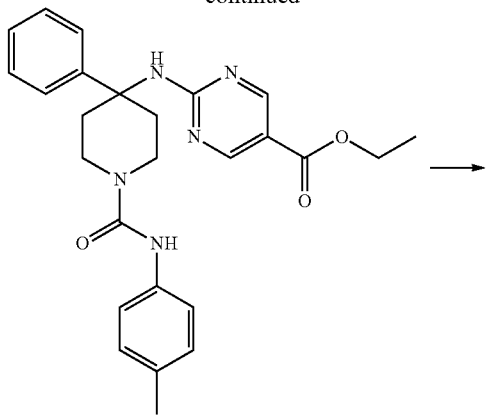

2

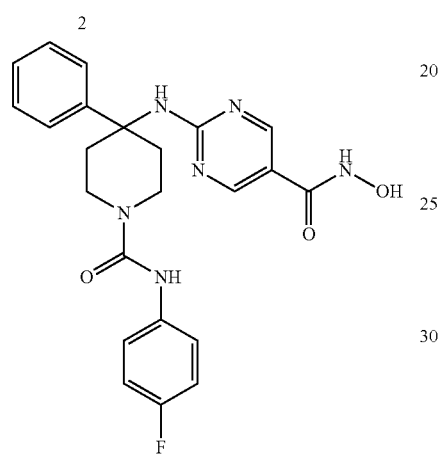

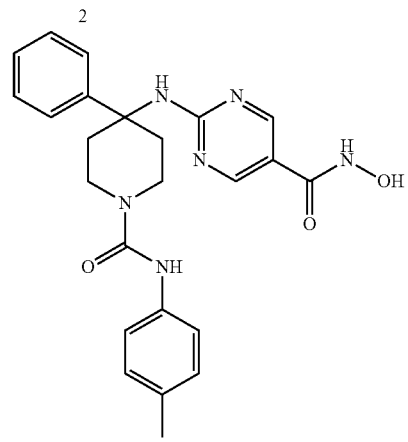

Step 1:

To a mixture of compound 1 (70 mg, 0.18 mmol) and 1-fluoro-4-isocyanatobenzene (25 mg, 0.18 mmol) in THF (4 ml) was added DIPEA (46 mg, 0.36 mmol) at r.t. The reaction was stirred for 1 hr, concentrated, and purified by gel chromatography (DCM:MeOH=10:1) to afford compound 2 (720 mg, 85%) as a white solid.

Step 2:

A procedure analogous to step 2 in Example 9 yielded Compound 014 (25 mg, 37%). $^1$H NMR (500 MHz, DMSO) δ 10.76 (s, 1H), 8.94 (s, 1H), 8.70-8.07 (m, 4H), 7.51-7.43 (m, 2H), 7.40 (d, J=7.5 Hz, 2H), 7.27 (t, J=7.7 Hz, 2H), 7.16 (t, J=7.3 Hz, 1H), 7.06 (t, J=8.9 Hz, 2H), 4.02 (d, J=13.2 Hz, 2H), 3.13 (t, J=12.3 Hz, 2H), 2.64 (d, J=12.8 Hz, 2H), 1.90 (dd, J=12.6, 9.3 Hz, 2H). LCMS: m/z=451 (M+H)$^+$.

Step 1:

A mixture of 1 (60 mg, 0.18 mmol) and 1-isocyanato-4-methylbenzene (25 mg, 0.18 mmol) in THF (4 ml) was added DIPEA (46 mg, 0.36 mmol) at r.t stirred for 1 hour, concentrated, purified by gel chromatography (DCM:MeOH=10:1) to afford 2 (70 mg, 85%) as white solid.

Step 2:

A procedure analogous to step 2 in Example 9 yielded Compound 015 (19 mg, 29%). $^1$H NMR (500 MHz, DMSO) δ 8.38 (dd, J=107.5, 101.2 Hz, 4H), 7.31 (dd, J=48.2, 18.7 Hz, 6H), 7.16 (s, 1H), 7.01 (s, 2H), 4.00 (s, 2H), 3.11 (s, 2H), 2.62 (s, 2H), 2.21 (d, J=7.4 Hz, 3H), 1.89 (s, 2H). LCMS: m/z=447 (M+H)$^+$.

Example 15

Synthesis of N-hydroxy-2-((4-phenyl-1-(p-tolylcarbamoyl)piperidin-4-yl)amino)pyrimidine-5-carboxamide (Compound 015)

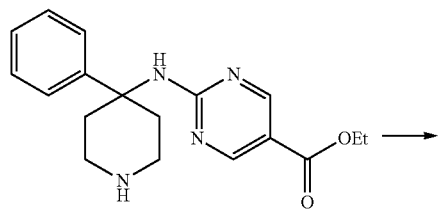

1

Example 16

Synthesis of N-hydroxy-2-((1-(methylcarbamoyl)-4-phenylpiperidin-4-yl)amino)pyrimidine-5-carboxamide (Compound 016)

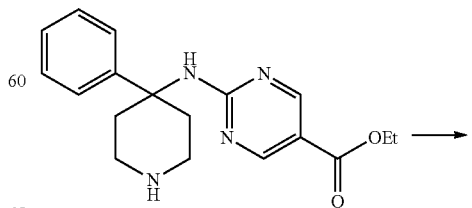

1

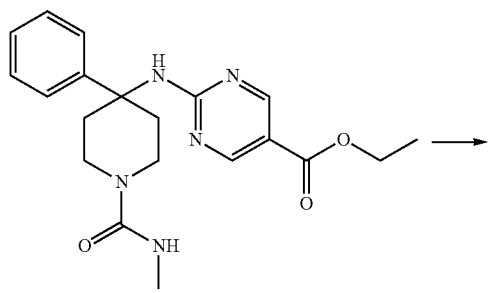
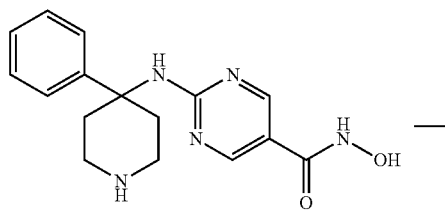
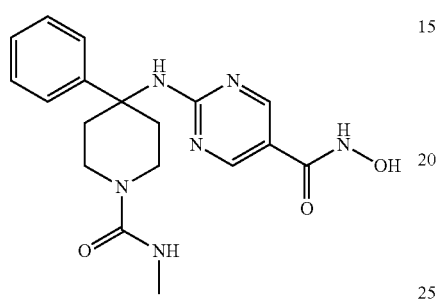
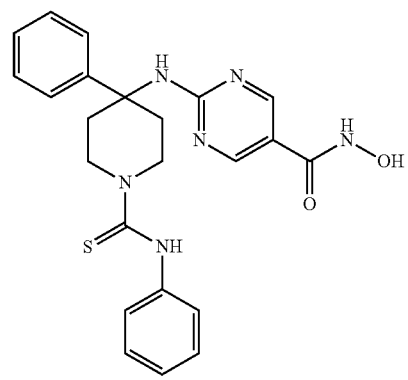

Step 1:

To a mixture of compound 1 (81 mg, 0.2 mmol) and methylcarbamic chloride (19 mg, 0.2 mmol) in THF (4 ml) was added DIPEA (46 mg, 0.36 mmol) at r.t. followed by stirring for 1 hr. The reaction was concentrated and purified by gel chromatography (DCM:MeOH=10:1) to afford compound 2 (50 mg, 61%) as a white solid.

Step 2:

A procedure analogous to step 2 in Example 9 yielded Compound 016 (22 mg, 46%). 1H NMR (500 MHz, DMSO) δ 10.71 (s, 1H), 8.95 (s, 1H), 8.59 (s, 1H), 8.34 (s, 1H), 8.12 (s, 1H), 7.37 (d, J=7.6 Hz, 2H), 7.26 (t, J=7.7 Hz, 2H), 7.15 (t, J=7.3 Hz, 1H), 6.40 (d, J=4.4 Hz, 1H), 3.80 (d, J=13.1 Hz, 2H), 2.98 (t, J=12.2 Hz, 2H), 2.60-2.53 (m, 5H), 1.80 (dd, J=12.6, 9.1 Hz, 2H). LCMS: m/z=371 (M+H)$^+$.

Step 1: A procedure analogous to step 2 in Example 9 afforded compound 2 (40 mg, 58%).

Step 2:

To a mixture of compound 2 (40 mg, 0.13 mmol) and isothiocyanatobenzene (17 mg, 0.13 mmol) in THF (2 ml) was added DIPEA (34 mg, 0.26 mmol) at r.t. followed by stirring for 20 mins. The reaction mixture was concentrated and purified by Pre-HPLC to afford Compound 017 (13 mg, 22%) as a white solid. $^1$H NMR (500 MHz, DMSO) δ 9.29 (s, 1H), 8.68-8.23 (m, 3H), 7.41 (d, J=7.6 Hz, 2H), 7.29 (t, J=5.1 Hz, 6H), 7.18 (t, J=7.2 Hz, 1H), 7.11-7.02 (m, 1H), 4.64 (d, J=11.3 Hz, 2H), 3.39 (d, J=12.0 Hz, 2H), 2.69 (d, J=13.0 Hz, 2H), 2.01 (t, J=11.2 Hz, 2H). LCMS: m/z=449 (M+H)$^+$.

Example 17

Synthesis of N-hydroxy-2-((4-phenyl-1-(phenylcarbamothioyl)piperidin-4-yl)amino)pyrimidine-5-carboxamide (Compound 017)

Example 18

Synthesis of 2-((1-((3-fluorophenyl)sulfonyl)-4-phenylpiperidin-4-yl)amino)-N-hydroxypyrimidine-5-carboxamide (Compound 018)

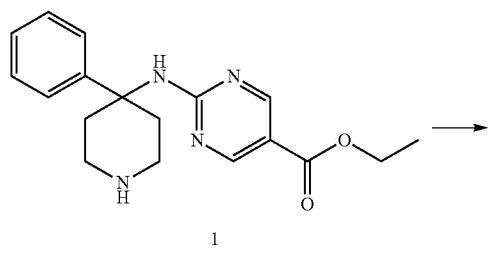
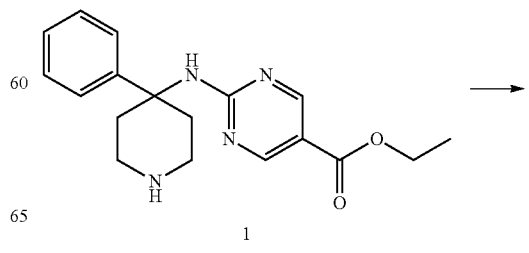

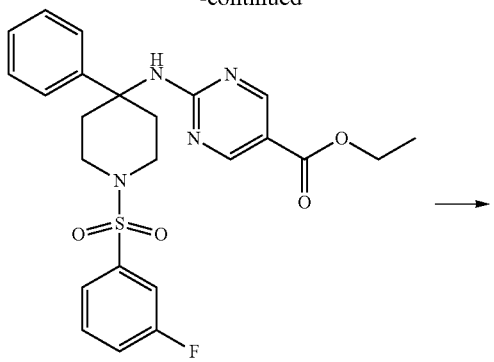

2

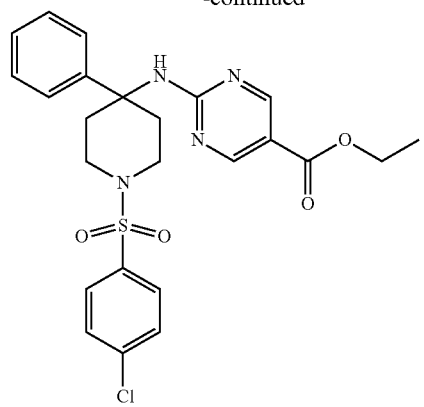

2

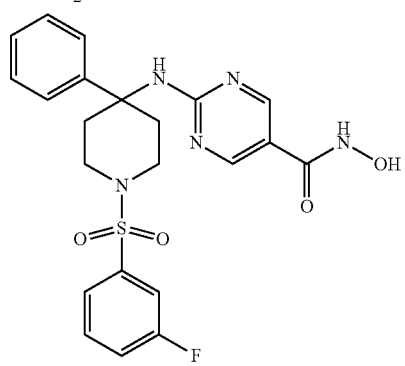

2

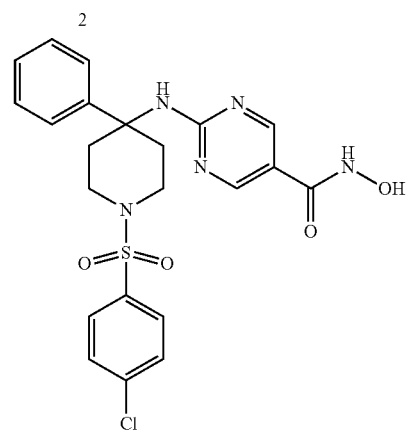

2

Step 1:

To a solution of compound 1 (55 mg, 0.14 mmol), 3-fluorobenzene sulfochloride (27 mg, 0.14 mmol) in 5 ml THF was added DIPEA (44 mg, 0.34 mmol). The mixture was stirred at r.t. for 2 h. LCMS was used to monitor the reaction to completion. The target compound (30 mg, 46%) was purified by flash chromatography with PE/EA (3:1).

Step 2:

To a solution of compound 2 (30 mg, 0.06 mmol) in 5 ml $CH_3OH/CH_2Cl_2$ was slowly added $NH_2OH$ (2 ml) at 0° C. followed by stirring for 10 mins. Then $NaOH/CH_3OH$ was slowly added to the solution and stirred for 3 h. After removing the solvent from the solution, the pH was adjusted to 6 by 2N HCl. The target compound, Compound 018, (13 mg, 46%) was purified by pre-HPLC. $^1$H NMR (500 MHz, DMSO) δ 8.91 (s, 1H), 8.47 (s, 1H), 8.29 (s, 1H), 7.75-7.68 (m, 1H), 7.66-7.55 (m, 3H), 7.32 (d, J=7.7 Hz, 2H), 7.25 (t, J=7.7 Hz, 2H), 7.15 (t, J=7.3 Hz, 1H), 3.61 (d, J=11.3 Hz, 2H), 2.63 (t, J=12.2 Hz, 4H), 2.00 (s, 2H). LCMS: m/z=472 (M+H)$^+$.

Example 19

Synthesis of 2-((1-((4-chlorophenyl)sulfonyl)-4-phenylpiperidin-4-yl)amino)-N-hydroxypyrimidine-5-carboxamide (Compound 019)

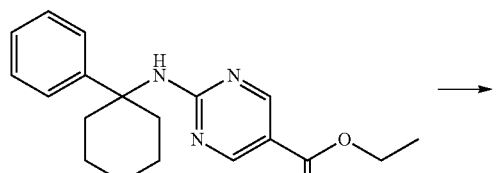

1

Step 1:

To a solution of compound 1 (70 mg, 0.17 mmol) and 4-chlorobenzene sulfochloride (36 mg, 0.17 mmol) in 5 ml THF was added DIPEA (44 mg, 0.34 mmol). The mixture was stirred at r.t. for 2 h. LCMS was used to monitor the reaction to completion. The target, compound 2, (56 mg, 65%) was purified by flash chromatography with PE/EA (3:1).

Step 2:

A procedure analogous to step 2 in Example 18 yielded Compound 019. $^1$H NMR (500 MHz, DMSO) δ 8.40 (t, J=60.5 Hz, 2H), 8.02 (s, 1H), 7.79 (d, J=8.5 Hz, 2H), 7.73 (d, J=8.5 Hz, 2H), 7.32 (d, J=7.6 Hz, 2H), 7.24 (d, J=7.7 Hz, 2H), 7.15 (t, J=7.1 Hz, 1H), 3.59 (d, J=11.3 Hz, 2H), 2.62 (dd, J=25.8, 13.9 Hz, 4H), 1.99 (s, 2H). LCMS: m/z=488 (M+H)$^+$.

Example 20

Synthesis of N-hydroxy-2-((4-phenyl-1-(o-tolylsulfonyl)piperidin-4-yl)amino)pyrimidine-5-carboxamide (Compound 020)

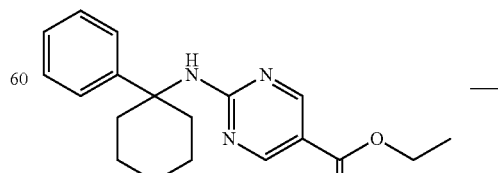

1

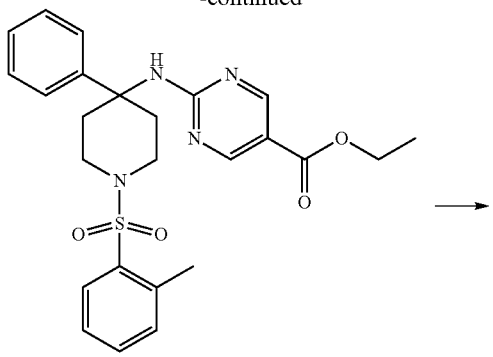

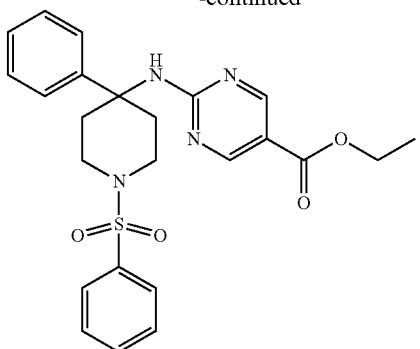

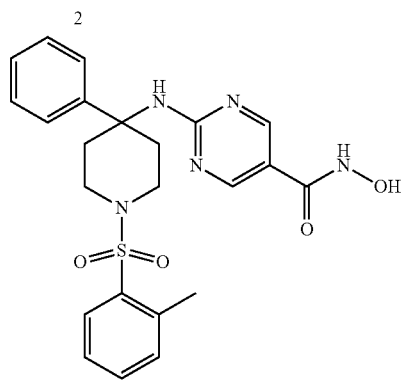

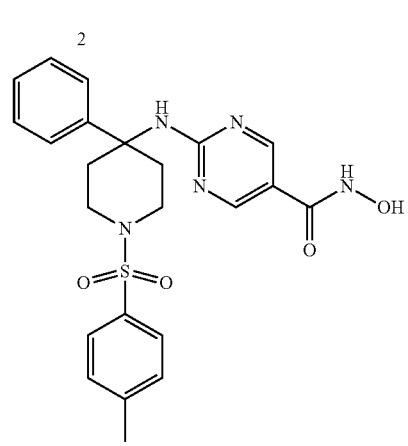

Step 1:

To a solution of compound 1 (55 mg, 0.14 mmol) and 2-methylbenzene sulfochloride (26 mg, 0.14 mmol) in 5 ml THF was added DIPEA (44 mg, 0.34 mmol). The mixture was stirred at r.t. for 2 h. LCMS was used to monitor the reaction to completion. The target compound (40 mg, 62.5%) was purified by flash chromatography with PE/EA (3:1).

Step 2:

A procedure analogous to step 2 in Example 18 yielded Compound 020. $^1$H NMR (500 MHz, DMSO) δ 8.96 (s, 1H), 8.47 (s, 1H), 8.31 (s, 1H), 8.08 (s, 1H), 7.82 (d, J=8.1 Hz, 1H), 7.58 (t, J=7.0 Hz, 1H), 7.44 (dd, J=20.0, 7.7 Hz, 2H), 7.34 (d, J=7.6 Hz, 2H), 7.26 (t, J=7.7 Hz, 2H), 7.15 (t, J=7.2 Hz, 1H), 3.53 (d, J=12.1 Hz, 2H), 2.89 (t, J=12.0 Hz, 2H), 2.67 (s, 2H), 2.59 (s, 3H), 1.96 (s, 2H). LCMS: m/z=468 (M+H)$^+$.

Example 21

Synthesis of N-hydroxy-2-((4-phenyl-1-tosylpiperidin-4-yl)amino)pyrimidine-5-carboxamide (Compound 021)

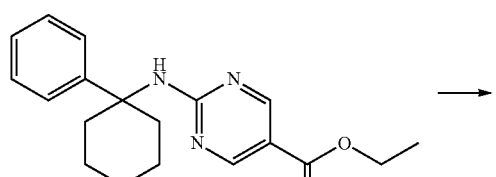

Step 1:

To a solution of compound 1 (55 mg, 0.14 mmol) and 4-methylbenzene sulfochloride (26 mg, 0.14 mmol) in 5 ml THF was added DIPEA (44 mg, 0.34 mmol). The mixture was stirred at r.t for 2 h. LCMS was used to monitor the reaction to completion. The target compound (48 mg, 75%) was purified by flash chromatography with PE/EA (3:1).

Step 2:

A procedure analogous to step 2 in Example 18 yielded Compound 021. $^1$H NMR (500 MHz, DMSO) δ 10.85 (s, 1H), 8.97 (s, 1H), 8.51 (s, 1H), 8.28 (s, 1H), 7.65 (d, J=8.1 Hz, 2H), 7.45 (d, J=8.1 Hz, 2H), 7.32 (d, J=7.7 Hz, 2H), 7.24 (t, J=7.6 Hz, 2H), 7.14 (t, J=7.1 Hz, 1H), 3.56 (d, J=11.7 Hz, 2H), 2.66 (s, 2H), 2.56 (t, J=11.9 Hz, 2H), 2.41 (s, 3H), 2.00 (d, J=10.5 Hz, 2H). LCMS: m/z=468 (M+H)$^+$.

Example 22

Synthesis of N-hydroxy-2-((4-phenyl-1-((4-(trifluoromethyl)phenyl)sulfonyl)piperidin-4-yl)amino)pyrimidine-5-carboxamide (Compound 022)

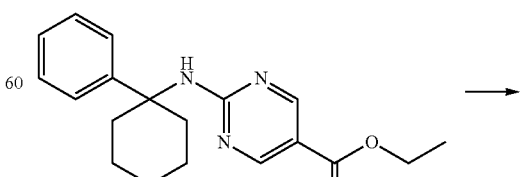

-continued

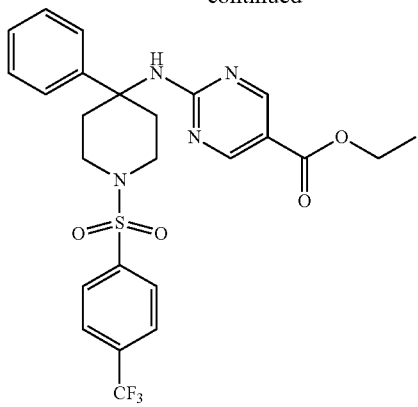

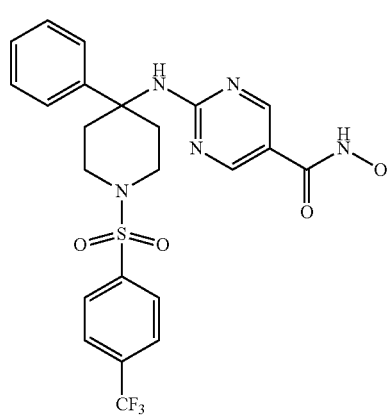

Step 1:
To a mixture of compound 1 (55 mg, 0.13 mmol) and 4-(trifluoromethyl)benzene-1-sulfonyl chloride (33 mg, 0.13 mmol) in THF (4 ml) was added DIPEA (31 mg, 0.24 mmol) at r.t. followed by stirring for 20 min. The reaction mixture was concentrated and purified by gel chromatography (PE:EA=2:1) to afford compound 2 (55 mg, 79%) as a yellow solid.

Step 2:
To a solution of compound 2 (60 mg, 0.1 mmol) in MeOH (3 mL) and DCM (1 ml) at 0° C. was added $NH_2OH$ (0.1 ml) followed by stirring for 10 min. Then NaOH/MeOH (0.2 ml) was added and the reaction stirred for 2 hrs after which it was concentrated. The pH was adjusted to 5 and extracted with EA (10 ml). Purification by Pre-HPLC afforded Compound 022 (20 mg, 38%). $^1$H NMR (500 MHz, DMSO) δ 10.94 (s, 1H), 8.57 (t, J=163.9 Hz, 3H), 8.03 (q, J=8.4 Hz, 5H), 7.30 (d, J=7.7 Hz, 2H), 7.24 (t, J=7.7 Hz, 2H), 7.15 (t, J=7.2 Hz, 1H), 3.64 (d, J=12.1 Hz, 2H), 2.65 (t, J=11.3 Hz, 4H), 2.01 (d, J=11.1 Hz, 2H). LCMS: m/z=522 (M+H)+.

Example 23

Synthesis of N-hydroxy-2-((4-phenyl-1-(phenylsulfonyl)piperidin-4-yl)amino)pyrimidine-5-carboxamide (Compound 023)

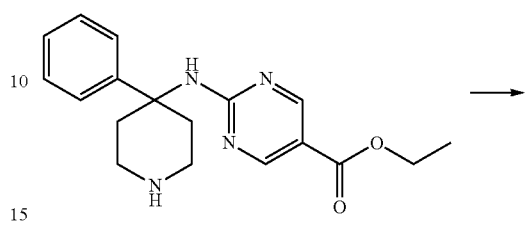

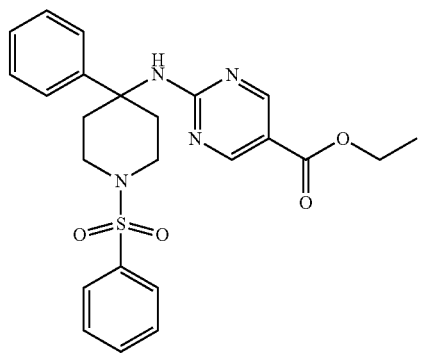

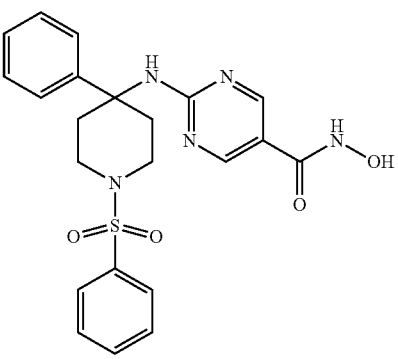

Step 1:
To a solution of compound 1 (80 mg, 0.25 mmol) and benzene sulfochloride (44 mg, 0.25 mmol) in 5 ml THF was added DIPEA (80 mg, 0.63 mmol). The mixture was stirred at r.t. for 3 h. LCMS was used to monitor the reaction to completion. The target compound (60 mg, 51%) was purified by flash chromatography with PE/EA (2:1).

Step 2:
A procedure analogous to step 2 in Example 18 yielded Compound 023. $^1$H NMR (400 MHz, DMSO) δ 10.88 (s, 1H), 8.96 (s, 1H), 8.50 (s, 1H), 8.28 (s, 1H), 8.01 (s, 1H), 7.82-7.75 (m, 2H), 7.73 (t, J=7.3 Hz, 1H), 7.65 (t, J=7.4 Hz, 2H), 7.32 (d, J=7.6 Hz, 2H), 7.24 (t, J=7.7 Hz, 2H), 7.14 (t, J=7.2 Hz, 1H), 3.59 (d, J=11.7 Hz, 2H), 2.67 (d, J=12.8 Hz, 2H), 2.58 (t, J=11.9 Hz, 2H), 1.99 (t, J=11.1 Hz, 2H). LCMS: m/z=454 (M+H)$^+$.

Example 24

Synthesis of 2-((1-((2,6-difluorophenyl)carbamoyl)-4-phenylpiperidin-4-yl)amino)-N-hydroxypyrimidine-5-carboxamide (Compound 024)

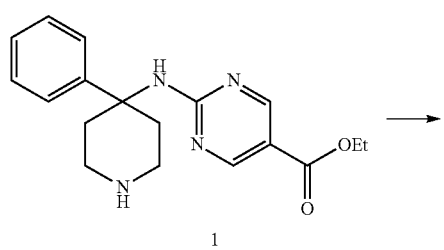

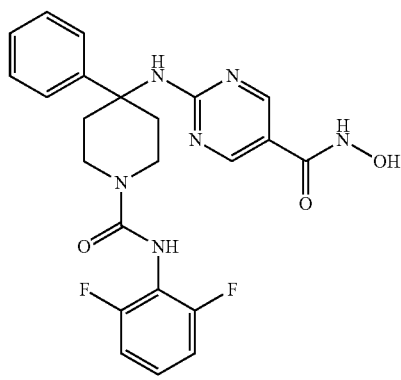

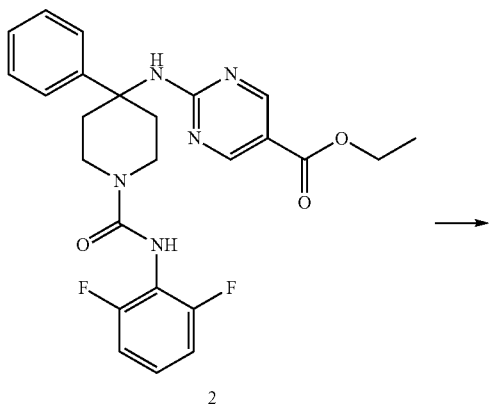

Step 1:

To a mixture of compound 1 (60 mg, 0.18 mmol) and 1,3-difluoro-2-isocyanatobenzene (28 mg, 0.18 mmol) in THF (4 ml) was added DIPEA (46 mg, 0.36 mmol) at r.t. followed by stirring for 20 mins. The reaction was concentrated and purified by gel chromatography (PE:EA=2:1) to afford compound 2 (70 mg, 81%) as a yellow solid.

Step 2:

A procedure analogous to step 2 in Example 9 yielded Compound 024 (28 mg, 43%). $^1$H NMR (500 MHz, DMSO) δ 10.94 (s, 1H), 8.97 (s, 1H), 8.62 (s, 1H), 8.35 (s, 1H), 8.24 (d, J=12.1 Hz, 2H), 7.40 (d, J=7.5 Hz, 2H), 7.32-7.22 (m, 3H), 7.17 (t, J=7.3 Hz, 1H), 7.10 (t, J=8.0 Hz, 2H), 3.97 (d, J=13.5 Hz, 2H), 3.16 (t, J=12.4 Hz, 2H), 2.64 (d, J=12.6 Hz, 2H), 1.92 (t, J=10.9 Hz, 2H). LCMS: m/z=469 (M+H)$^+$.

Examples 25-26

Synthesis of (R) and (S) N-hydroxy-2-((1-(3-methyl-2-phenylbutanoyl)-4-phenylpiperidin-4-yl)amino)pyrimidine-5-carboxamide (Compounds 025 and 026)

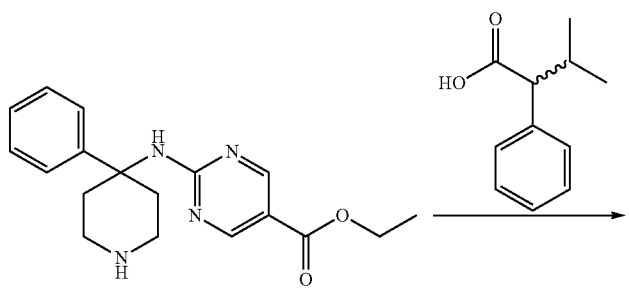

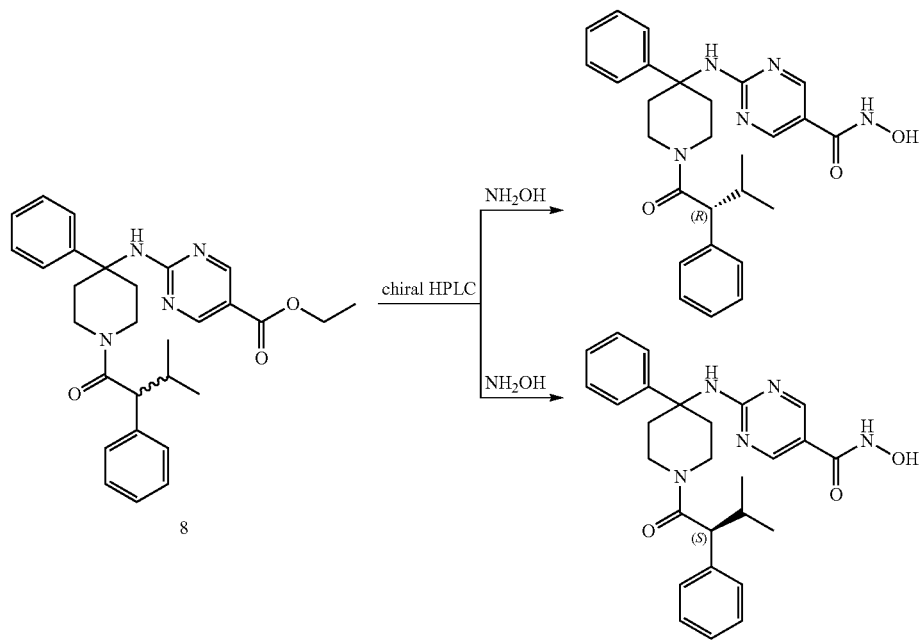

Step 1:

To a solution of compound 7 (200 mg, 0.50 mmol) and 3-methyl-2-phenylbutanoic acid (90 mg, 0.50 mmol) in 5 ml DMF was added HOAT (68 mg, 0.50 mmol), EDCI (78 mg, 050 mmol) and DIPEA (129 mg, 1 mmol). The mixture was stirred at 60° C. overnight and LCMS was used to monitor the reaction to completion. The racemic compound 8 (200 mg, 83%) was purified by filtration through silica gel after extraction by EA. Chiral-HPLC afforded R and S targets separately.

Step 2:

To a solution of each of the compounds from the above step (40 mg, 0.08 mmol) in 5 ml $CH_3OH/CH_2Cl_2$ was added $NH_2OH$ (0.1 ml) slowly at 0° C. followed by stirring for 10 min. $NaOH/CH3OH$ (0.3 ml) was added into the solution slowly and stirred for 2 h. After removing the solvent from the solution, the pH was adjusted to 6 by 2N HCl. The target compound was purified by pre-HPLC to afford Compound 025 (R) (26 mg, 26%). $^1H$ NMR (500 MHz, DMSO) δ 10.93 (s, 1H), 8.60 (s, 1H), 8.31 (s, 1H), 8.18 (d, J=6.4 Hz, 1H), 7.39-7.25 (m, 6H), 7.25-7.13 (m, 2H), 7.09 (d, J=7.2 Hz, 1H), 7.02 (d, J=7.6 Hz, 1H), 4.33 (d, J=12.6 Hz, 1H), 4.21-3.91 (m, 1H), 3.64 (dd, J=22.1, 9.9 Hz, 1H), 3.38-2.83 (m, 1H), 2.64 (s, 1H), 2.26 (s, 2H), 1.82 (d, J=43.9 Hz, 1H), 1.44 (s, 1H), 1.05 (t, J=7.0 Hz, 1H), 0.96 (dd, J=12.5, 6.4 Hz, 3H), 0.73 (s, 1H), 0.61 (t, J=7.3 Hz, 3H). LCMS: m/z=474 $(M+H)^+$. Compound 026 (S): (27 mg, 27%). $^1H$ NMR (500 MHz, DMSO) δ 10.94 (s, 1H), 8.97 (s, 1H), 8.60 (s, 1H), 8.30 (s, 1H), 8.18 (d, J=6.5 Hz, 1H), 7.39-7.25 (m, 6H), 7.19 (dt, J=14.9, 8.7 Hz, 2H), 7.08 (t, J=7.2 Hz, 1H), 7.02 (d, J=7.5 Hz, 1H), 4.33 (d, J=13.6 Hz, 1H), 4.14-3.97 (m, 1H), 3.64 (dd, J=21.8, 10.0 Hz, 1H), 3.02-2.86 (m, 1H), 2.63 (d, J=11.8 Hz, 1H), 2.24 (d, J=12.9 Hz, 2H), 1.91-1.70 (m, 1H), 1.44 (s, 1H), 0.96 (dd, J=12.6, 6.4 Hz, 3H), 0.73 (s, 1H), 0.61 (t, J=7.4 Hz, 3H). LCMS: m/z=474 $(M+H)^+$.

Example 27

Synthesis of (R)—N-hydroxy-2-((4-methyl-1-(2-phenylpropanoyl)piperidin-4-yl)amino)pyrimidine-5-carboxamide (Compound 027)

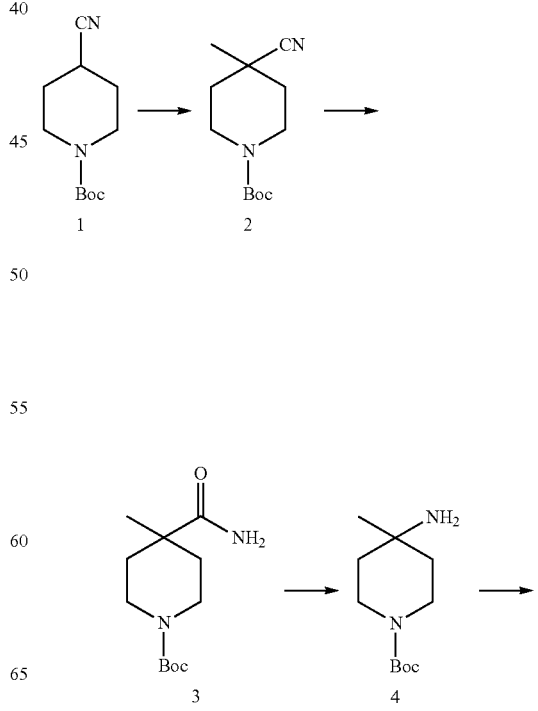

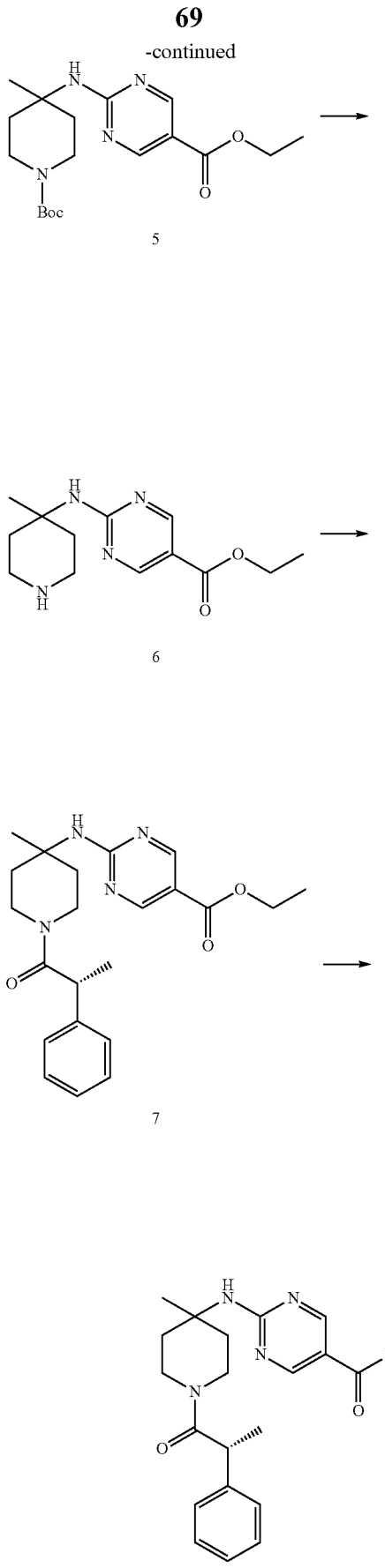

Step 1:
Lithium bis(trimethylsilyl)amide (1.0 M solution in THF, 240 mL, 240 mmol) was slowly added to a round-bottomed flask with compound 1 (25 g, 120 mmol) at −76° C. under $N_2$. The reaction was stirred for 4 h at −76° C. Then iodomethane (15 ml, 240 mmol) was added into the system. The reaction mixture was stirred at −76° C. for 30 min and then warmed to room temperature overnight. The resulting mixture was quenched with 150 ml saturated aqueous $NH_4Cl$, diluted with water, and extracted with EtOAc. The organic layers were washed with water and brine then dried over sodium sulfate, filtered and concentrated to afford the target compound 2 (25 g, 93%) as a white solid.

Step 2:
$K_2CO_3$ (31 g, 223 mmol) was added to the solution of the compound 2 (25 g, 111 mmol) in DMSO (120 mL). Then $H_2O_2$ (100 mL) was slowly added to the reaction dropwise at 60° C. The reaction was stirred overnight at 60° C. After completion, cold water was added and the mixture was extracted with EA. The organic layers were washed with water and brine, and dried over sodium sulfate, filtered and concentrated to afford the target, compound 3, (26 g, 96%) as a white solid.

Step 3:
Compound 3 (26 g, 107 mmol) was dissolved with $CH_3CN$ (200 mL) and 2N KOH (100 mL). Then 1,3-dibromo-5,5-dimethylimidazolidine-2,4-dione (15 g, 54 mmol) was added to the reaction and stirred overnight. Then the reaction pH was adjusted to 5 with 2N HCl and extracted with EA to remove the impurity. The aqueous phase was adjusted to a pH of 10. The precipitate was collected to afford the desired product as a white solid (16 g, 69%).

Step 4:
The solution of compound 4 (2 g, 9.34 mmol), ethyl 2-chloropyrimidine-5-carboxylate (2.6 g, 14.02 mmol) and DIPEA (5.3 g, 28.03 mmol) in 1,4-dioxane (25 mL) was heated at 95° C. overnight. Concentration and purification by a silica gel column with EA/PE=1/5 afforded compound 5 (1.8 g, 53%) as a light yellow solid.

Step 5:
To a solution of compound 5 (150 mg, 0.41 mmol) in DCM (3 ml) was added TFA (3 ml) at r.t. The reaction was stirred for 30 min. and the resulting mixture was concentrated to afford compound 6 without further purification (108 mg, 100%).

Step 6:
To a solution of compound 6 (108 mg, 0.41 mmol) and (R)-2-phenylpropanoic acid (61.5 mg, 0.41 mmol) in 5 ml DCM was added 2 ml TEA. The mixture was stirred at r.t. for 2 h and LCMS was used to monitor the reaction to completion. The target compound 7 (100 mg, 62%) was purified by filtration through silica gel.

Step 7:
To a solution of compound 7 (100 mg, 0.25 mmol) in 5 ml $CH_3OH/CH_2Cl_2$ was slowly added $NH_2OH$ (1 ml) at 0° C.

followed by stirring for 10 min. NaOH/CH₃OH (2 ml) was added into the solution slowly then stirred for 2 h. After removing the solvent from the solution, the pH was adjusted to 6 by 2N HCl. The target compound, Compound 027 (62 mg, 62%) was purified by Pre-HPLC to yield a white solid. ¹H NMR (500 MHz, DMSO) δ 11.04 (s, 1H), 8.58 (d, J=10.3 Hz, 2H), 7.48-7.41 (m, 1H), 7.36-7.16 (m, 5H), 4.10 (dq, J=20.4, 6.8 Hz, 1H), 3.96 (dd, J=47.4, 13.4 Hz, 1H), 3.57 (dd, J=37.9, 13.8 Hz, 1H), 3.22 (t, J=11.3 Hz, 0.5H), 3.05-2.86 (m, 1.5H), 2.27 (t, J=15.7 Hz, 1H), 2.02 (t, J=14.7 Hz, 1H), 1.46 (ddd, J=28.7, 17.1, 7.1 Hz, 1H), 1.37 (s, 1H), 1.30-1.20 (m, 3H), 1.18 (s, 0.5H), 1.17 (s, 1H), 0.56 (t, J=10.4 Hz, 0.5H). LCMS: m/z=384 (M+H)⁺.

Example 28

Synthesis of 2-((1-(2-(1H-indol-3-yl)acetyl)-4-phenylpiperidin-4-yl)amino)-N-hydroxypyrimidine-5-carboxamide (Compound 028)

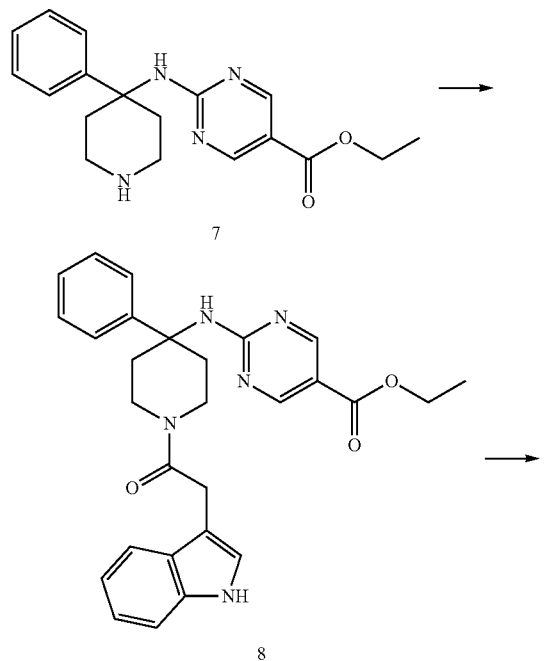

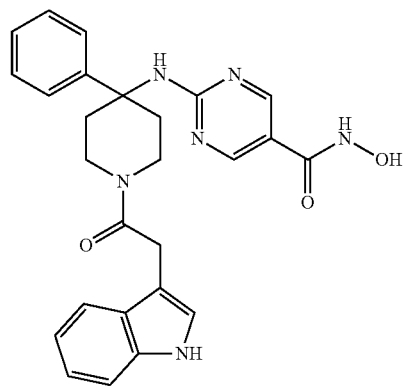

Step 1:
To a solution of compound 7 (100 mg, 0.25 mmol) and 2-(1H-indol-3-yl)acetic acid (44 mg, 0.25 mmol) in 5 ml DMF was added HOAT (68 mg, 0.50 mmol), EDCI (78 mg, 050 mmol) and DIPEA (129 mg, 1 mmol). The mixture was stirred at 60° C. for overnight. LCMS was used to monitor the reaction to completion. The target compound 8 (90 mg, 75%) as a yellow solid was obtained by filtration through silica gel after extraction by EA.

Step 2:
To a solution of compound 8 (90 mg, 0.19 mmol) in 5 ml CH3OH/CH2Cl2 was added NH2OH (0.2 ml) slowly at 0° C., then stirred for 10 min, NaOH/CH3OH (0.5 mL) was added into the solution slowly then stirred for 2 hrs, After removing the solvent from the solution, the PH was adjusted to 6 by 2N HCl. The target compound, Compound 028 (9 mg, 10%) was purified by Pre-HPLC to yield a white solid. ¹H NMR (500 MHz, DMSO) δ 10.92 (d, J=11.9 Hz, 2H), 8.60 (s, 1H), 8.31 (s, 1H), 8.16 (s, 1H), 7.59 (d, J=7.9 Hz, 1H), 7.34 (d, J=8.1 Hz, 1H), 7.20 (dd, J=18.3, 10.7 Hz, 3H), 7.10 (dd, J=14.2, 7.4 Hz, 4H), 6.98 (t, J=7.4 Hz, 1H), 4.33 (d, J=13.1 Hz, 1H), 3.94-3.86 (m, 1H), 3.84 (s, 1H), 3.78 (s, 1H), 3.23 (t, J=12.3 Hz, 1H), 2.84 (t, J=12.3 Hz, 1H), 2.36 (s, 1H), 1.66 (s, 1H), 1.40 (s, 1H).). LCMS: m/z=471 (M+H)⁺.

Examples 29-30

Synthesis of (S) and (R) N-hydroxy-2-((1-(4-methyl-2-phenylpentanoyl)-4-phenylpiperidin-4-yl)amino) pyrimidine-5-carboxamide (Compounds 029 and 030)

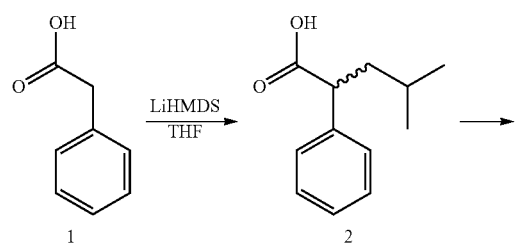

-continued

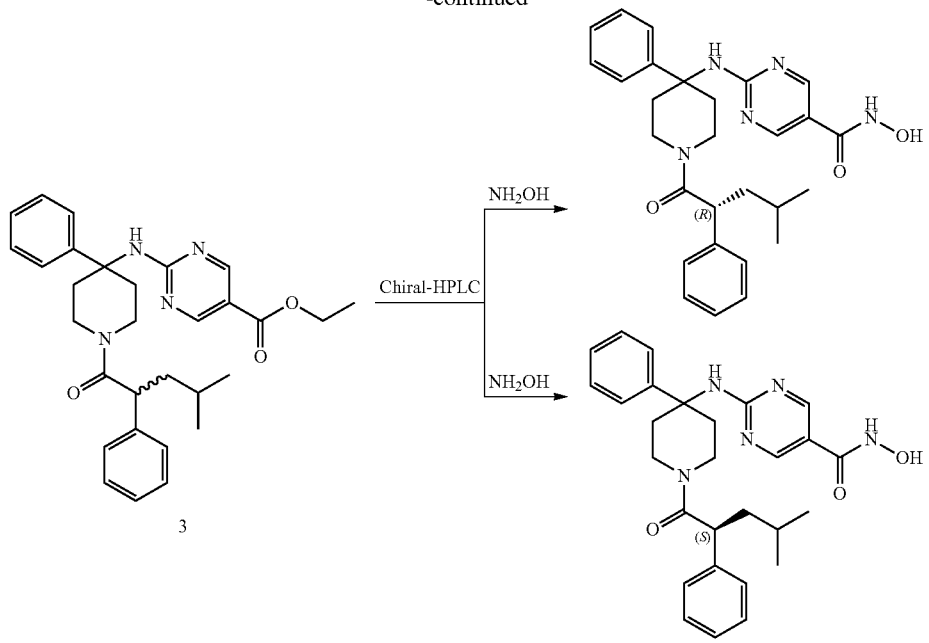

Step 1:
To a solution of 2-phenylacetic acid (250 mg, 1.84 mmol) in THF (3 mL) was added LHDMS (4 mL, 4 mmol) at 0° C. under $N_2$. The reaction was stirred for 15 min, then 1-iodo-2-methylpropane (0.23 mL, 2.02 mmol) was added into the solution and stirred at r.t. overnight. After completion, water was added and the mixture was extracted with EA. The target compound 2 (335 mg, 95%) was obtained as a white solid following purification by a silica gel column.

Step 2:
To a solution of compound 2 (188 mg, 0.98 mmol) and ethyl 2-(4-phenylpiperidin-4-ylamino)pyrimidine-5-carboxylate (400 mg, 0.98 mmol) in 5 ml DMF was added HOAT (267 mg, 1.96 mmol), EDCI (304 mg, 1.96 mmol) and DIPEA (507 mg, 3.93 mmol). The mixture was stirred at 60° C. overnight. LCMS was used to monitor the reaction to completion. The target compound 3 (220 mg, 75%) was purified by silica gel column with EA/PE=1/2. Compound 3 was isolated from Chiral-HPLC to afford compound R— (90 mg, 41%) and compound S— (90 mg, 41%).

Step 3:
To a solution of compounds from the above step (90 mg, 0.18 mmol) in 5 ml $CH_3OH/CH_2Cl_2$ was slowly added $NH_2OH$ (0.2 ml) at 0° C., followed by stirring for 10 min. $NaOH/CH_3OH$ (0.4 ml) was slowly added to the solution and then stirred for 2 h. After removing the solvent, the pH was adjusted to 6 by 2N HCl. The target compound was purified by Pre-HPLC: Compound 29 (S) (60 mg, 68%). $^1H$ NMR (500 MHz, DMSO) δ 10.91 (s, 1H), 8.96 (s, 1H), 8.55 (s, 1H), 8.31 (s, 1H), 8.14 (d, J=18.9 Hz, 1H), 7.44-7.23 (m, 6H), 7.13 (ddd, J=30.2, 19.8, 8.3 Hz, 2H), 7.01-6.95 (m, 2H), 4.34 (s, 1H), 4.11-3.91 (m, 2H), 2.84 (ddd, J=47.4, 25.9, 12.5 Hz, 1H), 2.72-2.56 (m, 1H), 2.50 (s, 1H), 2.23 (d, J=11.3 Hz, 0.5H), 1.90-1.79 (m, 2H), 1.75-1.30 (m, 2.5H), 0.94-0.74 (m, 6H), 0.72 (s, 1H). LCMS: m/z=488 (M+H)$^+$. Compound 030 (R) (60 mg, 68%): $^1$HNMR NMR (500 MHz, DMSO) δ 10.96 (s, 1H), 8.98 (s, 1H), 8.61 (s, 1H), 8.31 (s, 1H), 8.18 (d, J=19.3 Hz, 1H), 7.43-7.00 (m, 10H), 4.35 (d, J=12.0 Hz, 1H), 4.15-3.99 (m, 1H), 3.95 (d, J=13.1 Hz, 0.5H), 3.29 (d, J=12.5 Hz, 0.5H), 2.90 (dt, J=24.4, 12.5 Hz, 1H), 2.59 (dd, J=30.5, 16.2 Hz, 1H), 2.23 (d, J=12.9 Hz, 0.5H), 1.94-1.74 (m, 1.5H), 1.54-1.31 (m, 2.5H), 0.95-0.79 (m, 6H), 0.72 (t, J=11.1 Hz, 0.5H). LCMS: m/z=488 (M+H)$^+$.

Example 31

Synthesis of 2-((1-(2-(1H-indol-2-yl)acetyl)-4-phenylpiperidin-4-yl)amino)-N-hydroxypyrimidine-5-carboxamide (Compound 031)

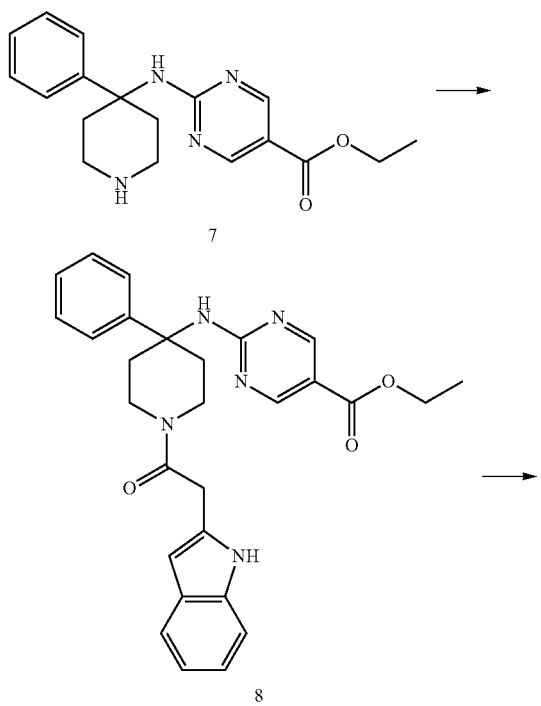

-continued

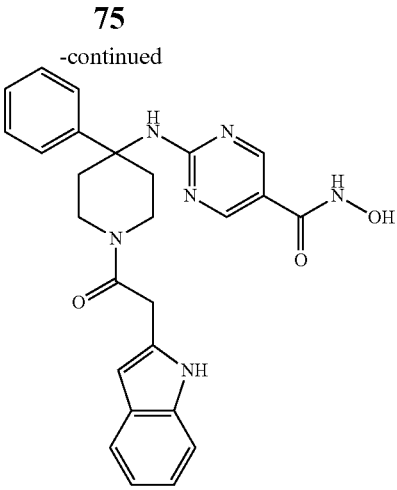

Step 1:

To a solution of compound 7 (100 mg, 0.25 mmol) and 2-(1H-indol-2-yl)acetic acid (44 mg, 0.25 mmol) in 5 ml DMF was added HOAT (68 mg, 0.50 mmol), EDCI (78 mg, 0.50 mmol) and DIPEA (129 mg, 1 mmol). The mixture was stirred at 60° C. overnight, LCMS monitored the reaction to completion. The target compound 8 (80 mg, 766%) was obtained as a yellow solid following extraction with EA and filtration through silica gel.

Step 2:

To a solution of compound 8 (80 mg, 0.17 mmol) in 5 ml $CH_3OH/CH_2Cl_2$ was slowly added NH2OH (0.2 ml) at 0° C. followed by stirring for 10 min. NaOH/CH3OH (0.4 ml) was added to the solution slowly and stirred for 2 h. After removing the solvent from the solution, the PH was adjusted to 6 by 2N HCl. Purified by Pre-HPLC yielded the target compound, Compound 031, (9 mg, 10%) was as a white solid. $^1$H NMR (500 MHz, DMSO) δ 10.94 (s, 2H), 8.61 (s, 1H), 8.32 (s, 1H), 8.24 (s, 1H), 7.42 (d, J=7.7 Hz, 1H), 7.31 (d, J=7.3 Hz, 3H), 7.24 (t, J=7.7 Hz, 2H), 7.14 (t, J=7.2 Hz, 1H), 7.00 (t, J=7.1 Hz, 1H), 6.92 (t, J=7.2 Hz, 1H), 6.20 (s, 1H), 4.34 (d, J=13.4 Hz, 1H), 3.92 (d, J=16.1 Hz, 2H), 3.34 (t, J=12.0 Hz, 1H), 2.91 (t, J=12.6 Hz, 1H), 2.64 (s, 1H), 1.88-1.70 (m, 2H). LCMS: m/z=471 (M+H)$^+$.

Example 32

HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 μM TCEP) to 6 fold their final concentration. The HDAC enzymes (purchased from BPS Biosciences) were diluted to 1.5 fold their final concentration in assay buffer. The tripeptide substrate and trypsin at 0.05 μM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 μM (HDAC1), 10 μM (HDAC2), 17 μM (HDAC3) and 14 μM (HDAC6).

Five μl of compounds and 20 μl of enzyme were added to wells of a black, opaque 384 well plate in duplicate. Enzyme and compound were incubated together at room temperature for 10 minutes. Five μl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit. The $IC_{50}$ values obtained for several of the compounds of this invention are found in Table 1.

Example 33

Pharmacological Inhibition of Histone Deacetylase (HDAC) 1, 2 or 3 have Distinct Effects on Cellular Viability, Erythroid Differentiation, and Fetal Globin (HbG) Induction In this example, the effects of selective inhibitors of HDAC1, 2, or 3, on cytoxicity, erythroid differentiation, and HbG induction in cultured human CD34+ bone marrow cells was investigated.

A prior compound, Compound A, is a class I HDAC inhibitor with $IC_{50}$ values of 5, 5, and 8 nM against HDAC1, 2, and 3, respectively (i.e., it is a non-selective HDAC inhibitor). Compound 001 is 30-fold selective for HDAC1 and 2, with $IC_{50}$ values of 38, 34, and 1010 nM against HDAC1, 2, and 3, respectively. Treatment of cells for 4 days with Compound A (1 μM) resulted in a 20-fold decrease in cells viability, while treatment with Compound 001 (1 μM) resulted in a minimal reduction in viability (1.2-fold) and a 2-fold increase in the percentage of HbG relative to other beta-like globin transcripts (see FIG. 1). This result suggests that pharmacological inhibition of HDAC3 is cytotoxic and is consistent with the therapeutic rationale for the design of selective inhibitors of HDAC1 and 2.

Example 34

Evaluation of Test Compounds on Human Erythroid, Myeloid and Megakaryocyte Hematopoietic Progenitor Proliferation in Media Formulations Containing Various Cytokines This study evaluated the potential effect of test compounds on human erythroid, myeloid and megakaryocyte hematopoietic progenitor proliferation in media formulations containing various cytokines. Normal human bone marrow light density cells derived from a normal bone marrow donor (Lonza, Md.) were used for these studies. Clonogenic progenitors of human erythroid (CFU-E, BFU-E) and granulocyte-monocyte (CFU-GM) lineages were assessed in a semi-solid methylcellulose-based media formulation containing rhIL-3 (10 ng/mL), rhGM-SCF (10 ng/mL), rhSCF (50 ng/mL) and Epo (3 U/mL). Clonogenic progenitors of human megakaryocyte lineage were assessed in a semi-solid collagen based matrix containing rhIL-3 (10 ng/mL), rhIL-6 (10 ng/mL) and rhTpo (50 ng/mL).

Compounds were added to the medium to give the final desired concentrations. Solvent control cultures (containing no compound but 0.1% DMSO) as well as standard controls (containing no compound and no DMSO) were also initiated for both media formulations. Human myeloid and erythroid progenitor assays were initiated at $2.5 \times 10^4$ cells per culture and human megakaryocyte progenitor assays were initiated with 1×10$^5$ cells per culture. Following 14-16 days in culture, myeloid and erythroid colonies were assessed microscopically and scored by trained personnel. The colonies were divided into the following categories, based on size and morphology; CFU-E, BFU-E, and CFU-GM. For the human megakaryocyte assay, the cultures were transferred from the 35 mm dishes to labeled glass slides, were fixed (methanol/acetone) and then stained using an anti-human CD41 antibody and an alkaline phosphate detection system according to manufactures' instructions. The colonies were assessed and scored by trained personnel and divided into the following categories based on size; CFU-Mk (3-20), CFU-Mk (21-49) and CFU-Mk (≥50).

The mean±1 standard deviation of three replicate cultures was calculated for progenitors in both media formulations. To calculate the concentration of 50% inhibition of colony growth (IC$_{50}$) for each compound, a dose response curve was generated plotting the log of the compound concentration versus the percentage of control colony growth using Origin® 8. A sigmoidal curve was then fit to the graph and from this curve the inhibitory concentration (μM) was then calculated using the Boltzman equation $$y = \left[ \frac{A_1 - A_2}{1 + e^{\left(\frac{x-x_0}{dx}\right)}} \right] + A_2$$

where $A_1$=the initial value (baseline response), $A_2$=0 (maximum response), $x_o$=center (drug concentration that provokes a response halfway between $A_1$ and $A_2$) and dx=slope of the curve at midpoint as determined by Origin® 8. Results are shown in FIGS. 2A-F.

This example demonstrates that Compound-001, an HDAC1,2-selective compound, has significantly less cytotoxicity against erythroid, myeloid and megakaryocytes than does MS-275, an HDAC1,2,3-selective compound. These results suggest that selective inhibition of HDAC1 and 2 using Compound-001 may result in significantly less in vivo cytotoxicity in the hematopoietic compartment than pan-HDAC inhibitors.

Example 35

In Vitro Cell Proliferation

Figure 3A:
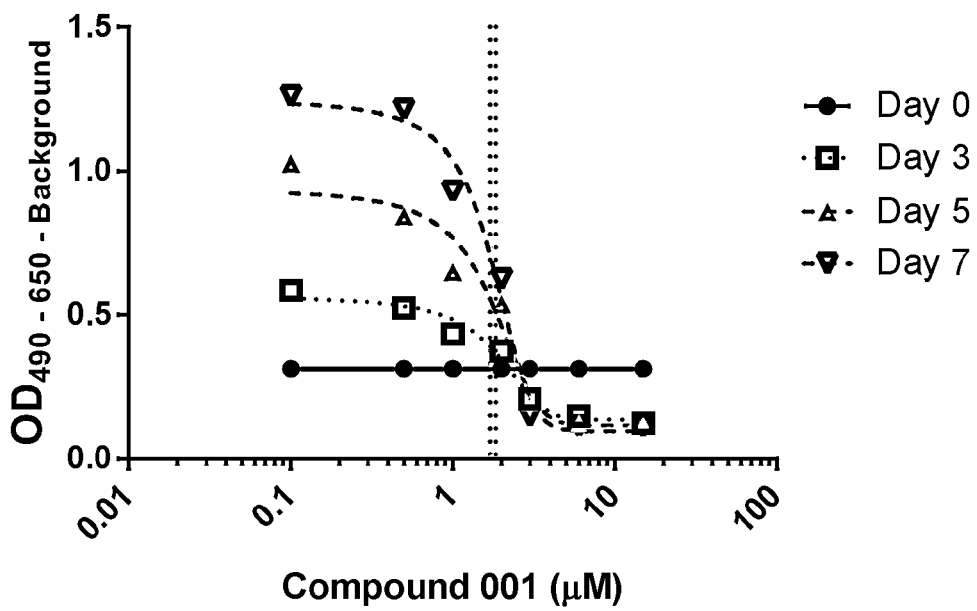
FIG. 3A shows dose-response curves for Compound 001 at Day 0, Day 3, Day 5, and Day 7, with the half-maximal dose ($IC_{50}$) at each day indicated by a dashed line.
Figure 3B:
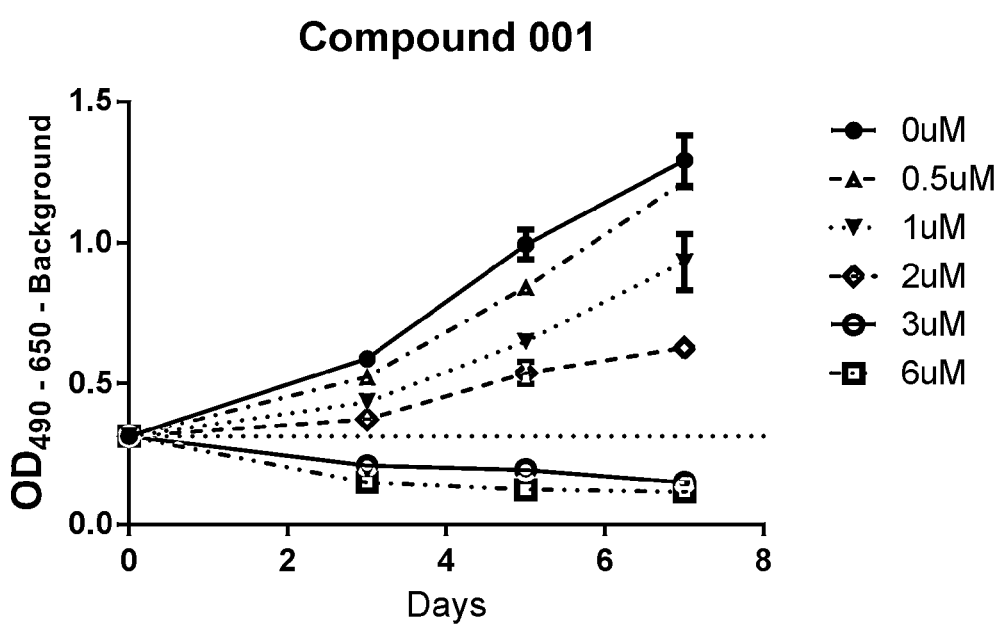
FIG. 3B shows the relative growth of H929 cells over time in the absence of drug as well as in the presence of increasing doses of Compound 001. The dashed line indicates the level of viability at Day 0, thus doses over 3 uM resulted in a net decrease in the viability of H929 cells.

H929 human myeloma cells were seeded in 96-well plates and grown in the presence of increasing levels of Compound 001 for a period up to 7 days. Cellular viability was assessed using Aqueous One MTS reagent at Days 0 (immediately after seeding), 3, 5, and 7. FIG. 3A shows dose-response curves for Compound 001 at Day 0, Day 3, Day 5, and Day 7, with the half-maximal dose (IC$_{50}$) at each day indicated by a dashed line. FIG. 3B shows the relative growth of H929 cells over time in the absence of drug as well as in the presence of increasing doses of Compound 001. The dashed line indicates the level of viability at Day 0, thus doses over 3 uM resulted in a net decrease in the viability of H929 cells.

Example 36

Synthesis of N-(2-amino-5-(thiophen-2-yl)phenyl)-2-cyclopropyl-1-(2-morpholinoethyl)-1H-indole-5-carboxamide (Compound X)

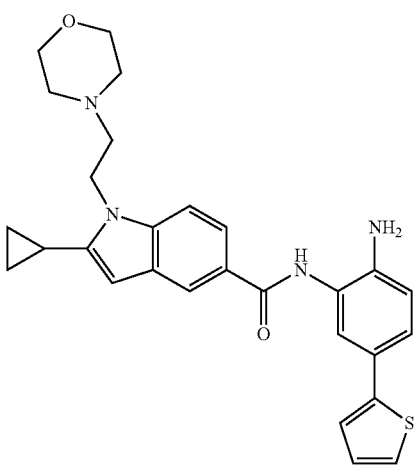 [SMILES: Nc1ccc(-c2cccs2)cc1NC(=O)c1ccc2c(c1)cc(C1CC1)n2CCN1CCOCC1]

Reaction Scheme

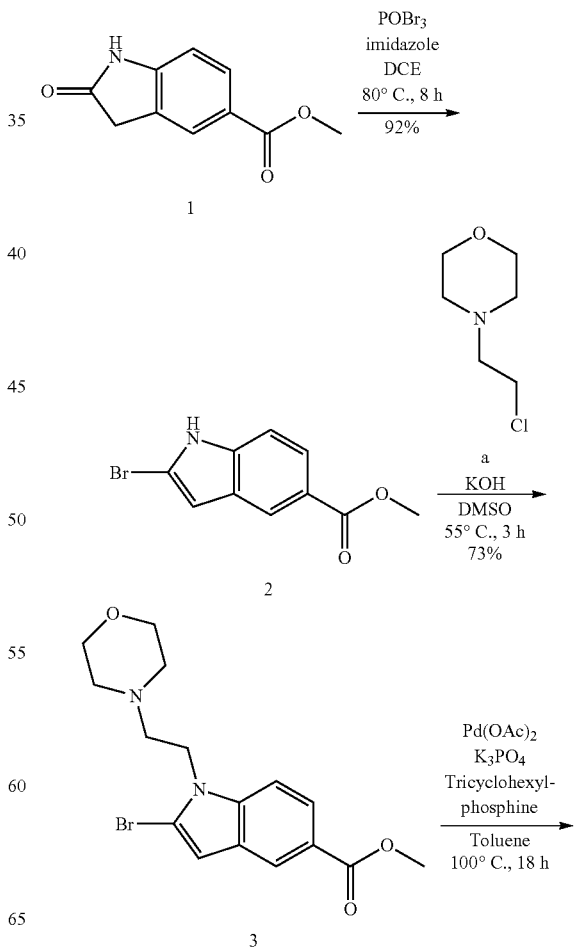

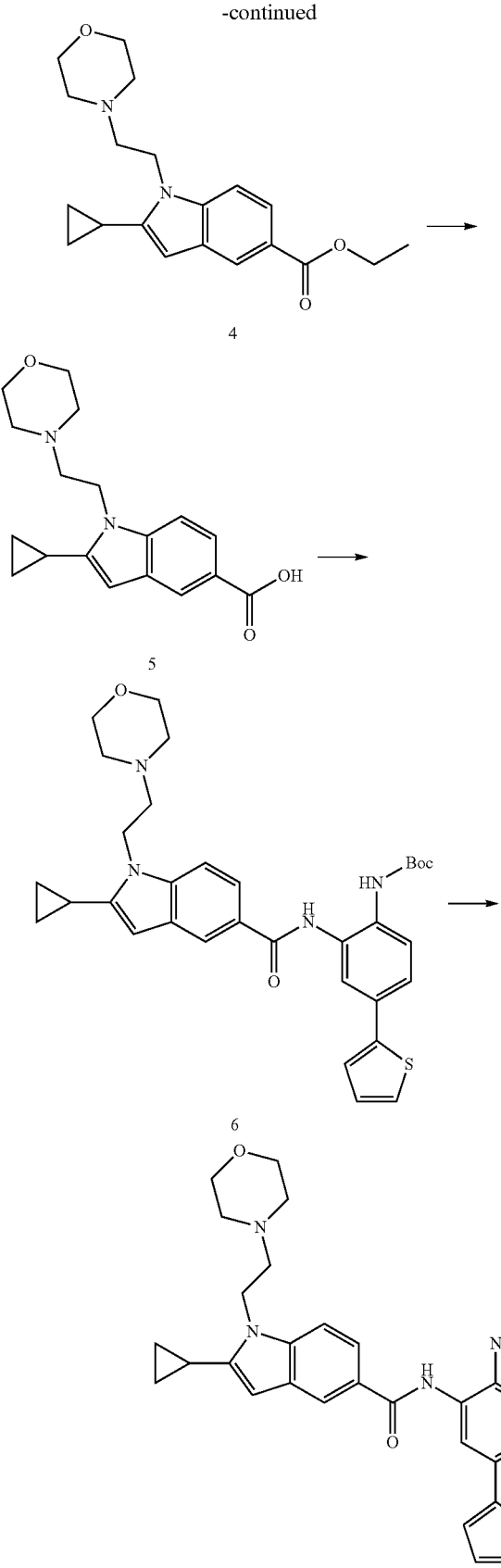

Experimental Procedure

Step 1:

To a solution of compound 1 in DCE was added POBr$_3$ and imidazole. The reaction was stirred at 80° C. overnight. Water and DCM were added to the reaction, and the organic layer was separated, washed with brine, and dried under reduced pressure to give compound 2.

Step 2:

To a solution of compound 2 in DMSO was added compound a and KOH. The resulting reaction mixture was stirred at 45° C. for 4 h, quenched with H$_2$O, and extracted with EA. The combined organic layers were purified by gel chromatography to yield the desired product, compound 3.

Step 3:

A mixture of compound 3, cyclopropyl boronic acid, Pd(OAc)$_2$, tricyclohexylphosphine, and K$_3$PO$_4$ in toluene and water was stirred at 100° C. under N$_2$ atmosphere overnight. The mixture was cooled, filtered, and concentrated to obtain a residue, which was purified by Prep-TLC to get compound 4.

Step 4:

A mixture of compound 4 and NaOH in EtOH and THF was stirred at 60° C. for 5 h. The mixture was concentrated to obtain a residue, to which was added aq. sat. citric acid and extracted with EA. The organic layers were separated, dried, filtered and concentrated to obtain compound 5.

Step 5:

A mixture of compound 5, tert-butyl 2-amino-4-(thiophen-2-yl)phenylcarbamate, HOAT, EDCI, and DIPEA in DMF was stirred at 55° C. for overnight. Water was added to the mixture, and extracted with EA. The organic layers were separated, dried, filtered, and concentrated to get a residue, which was purified by Prep-TLC to afford compound 6.

Step 6:

To a solution of compound 6 in DCM was added TFA and stirred at r.t. for 1 h. The mixture was concentrated to obtain a residue, which was purified by Prep-HPLC to afford compound 7. $^1$H NMR (500 MHz, DMSO) δ 9.63 (s, 1H), 8.16 (s, 1H), 7.79-7.73 (m, 1H), 7.51 (d, J=2.1 Hz, 2H), 7.36 (d, J=5.1 Hz, 1H), 7.29 (dd, J=8.3, 2.1 Hz, 1H), 7.25 (d, J=3.5 Hz, 1H), 7.05 (dd, J=5.0, 3.6 Hz, 1H), 6.82 (d, J=8.3 Hz, 1H), 6.24 (s, 1H), 5.12 (s, 2H), 4.43 (s, 2H), 3.57 (s, 5H), 2.77-2.58 (m, 2H), 2.09 (s, 1H), 1.02 (d, J=8.0 Hz, 2H), 0.76 (d, J=4.4 Hz, 2H). LCMS: m/z=487.2 (M+H)+.

Table 2 below shows the IC$_{50}$ (nM) of Compound X for HDACs 1, 2, and 3.

TABLE 2

| Compound | HDAC1 | HDAC2 | HDAC3 |
|---|---|---|---|
| Compound X | 6 | 36 | 445 |

Example 37

HDAC1/2/6 Selective Inhibitor Blocks Neuroblastoma Migration

Many cultured cancer cells are able to migrate across a membrane and this activity indicates the metastatic potential of the cancer cells. The migration of neuroblastoma cell line SK-N-SH was compared in the presence or absence of Compound 001, a HDAC1/2/6 inhibitor. The cancer cells were seeded and grown on a membrane surface, and the cell numbers on the other side of the membrane were counted under a microscope after 12 hours. A decreased number of migrated cells by the HDAC1/2/6 inhibitor suggests a migration suppression activity of HDAC1/2/6 inhibitor. In the study, an HDAC inhibitor was added to the cells either 2 hours before or when the migration was measured. The effect of HDAC1/2/6 inhibitor on Epidermal Growth Factor (EGF) stimulated cancer cell migration using 40 ng/ml of EGF in the assay was investigated.

The protocol for the migration assay was as follows. The compounds were prepared in DMSO at 400× stock of the final required concentrations. See Table 3.

TABLE 3

| Compound | Final conc. (µM) | Cpds 400* Conc. (µM) |
|---|---|---|
| Compound 001 | 0.5 | 200 |
| Gefitinib | 1 | 400 |
| EGF | 20 | 8 |

200 µl of warm basal RPMI1640 medium was added to the interior of the inserts, allowed to rehydrate for 2 hours in a humidified tissue culture incubator at 37° C., 5% $CO_2$ atmosphere. During rehydration, the cells were harvested with trypsin, washed 3 times, and then resuspended with pre-warmed basal RPMI1640 medium containing 500,000 cells/ml or 250,000 cells/ml. The compounds were diluted to 20× with basal RPMI1640 medium. 25 µl of 20× compound was added to the 500 µl cell suspension to make the final cell suspension with compound. 100 µl of 20× compound was added to 1,900 µl RPMI1640 medium with 10% FBS to get the final medium, and 500 µl of the final medium was added to the well a new 24-well plate. After rehydration, the medium was removed from the inserts, and then 100 µl final cell suspension was added to the chambers. The chambers were transferred to the wells containing final medium. 100 µl/well of final cell suspension (diluted with final medium to ½ density) was added to a 96-well plate (triplicate). After 8 hours incubation at 37° C., the non-invading cells were removed from the upper surface of the membrane with cotton swabs. Cells on the lower surface of the membrane were fixed with 4% paraformaldehyde for 15 minutes at room temperature, and then stained with crystal violet for 30 minutes. After staining, the inserts were washed in PBS several times to ensure that there was no crystal violet on the membrane, except the cells. The number of migrated cells were counted under a microscope in five fields at 100× magnification. The viable cells were seeded in the 96 well plate with the same treatment as in the migration assay were measured using CTG (Cell Titer Glow).

Figure 4A:
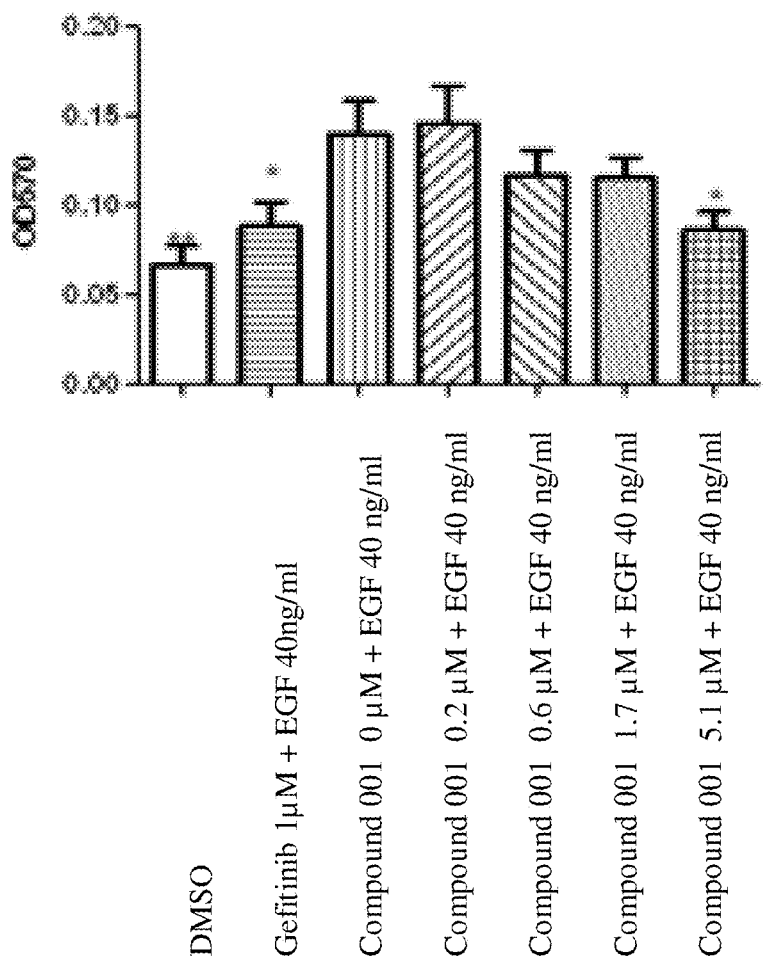
FIGS. 4A-C are a set of graphs that show the results of migration assays in neuroblastoma cells.
Figure 4B:
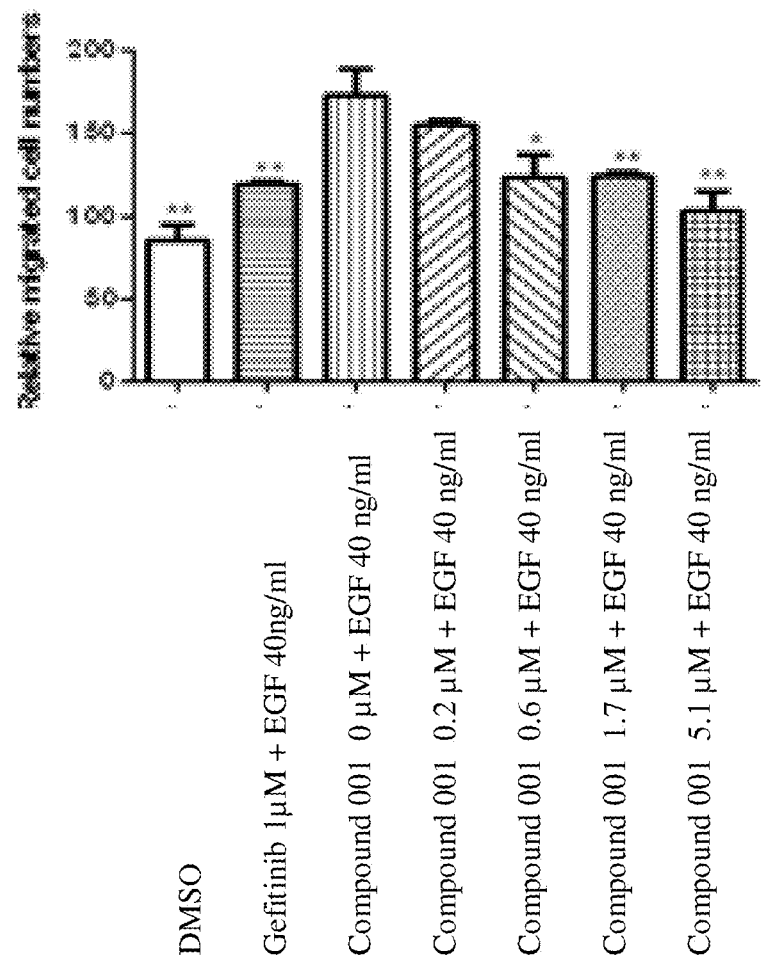
Figure 4C:
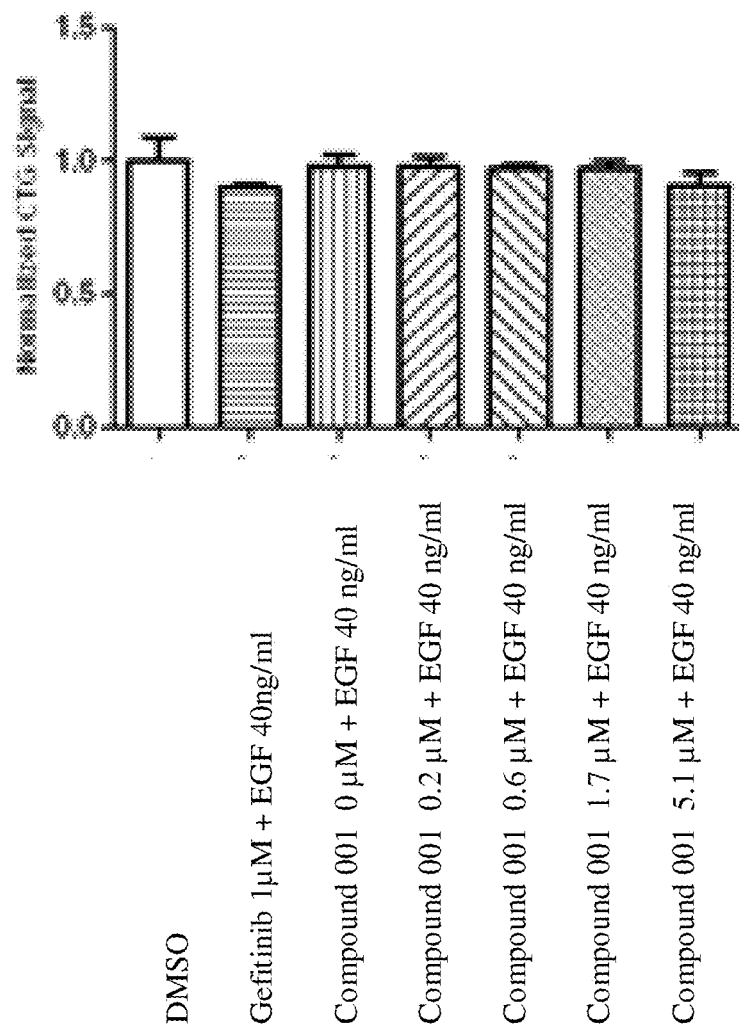

The results of these experiments are shown in FIGS. 4A-C.

Example 38

HDAC1/2 Selective Inhibitors Induce Neuroblastoma Maturation

The following is a quick summary of the HDAC neuroblastoma maturation experiments. Adherent cells were plated into 12- or 24-well plates at $10^6$ cells/well and allowed to adhere for 2-4 hours. Compounds were dispensed in DMSO at the indicated concentrations using an automated liquid handling system (Tecan D300) and incubated for the indicated times at 37° C. with 5% $CO_2$. Cells were harvested and RNA extracted using the Qiagen RNeasy Mini Kit according to manufacture protocols. The RNA was quantified and relative expression levels were assessed using the Applied Biosystems TaqMan RNA-to-Ct Kit according to manufacture protocols using the indicated TaqMan probes.

The protocol for the maturation experiments was as follows. The day before the experiment, the cells were fed in the flask by doubling the media. The cells were then harvested by adding non-enzymatic cell dissociation media and incubating at 37° C. for 15 minutes. The cells were transferred to a 50 ml tube and pipet to create a single-cell suspension. The cells were washed with PBS buffer. The cells were then resuspended in complete media at $5\times10^5$ cells per ml. Next, 2 ml of cells were transferred to 24- or 12-well plates. The treatment compounds were then dispensed into each well using the D300 liquid handler. The cells were then incubated for the indicated time at 37° C. The cells were harvested by scraping the cells and transferring to a 2 ml tube. The cells were spun to form a pellet. Next, RNA was extracted using the Qiagen RNeasy Mini kit according to manufacture protocols. The RNA concentration was recorded. The relative RNA levels were assessed using the Applied Biosystems TaqMan RNA-to-Ct kit according to manufacture protocols using the indicated Taqman probes.

Figure 5A:
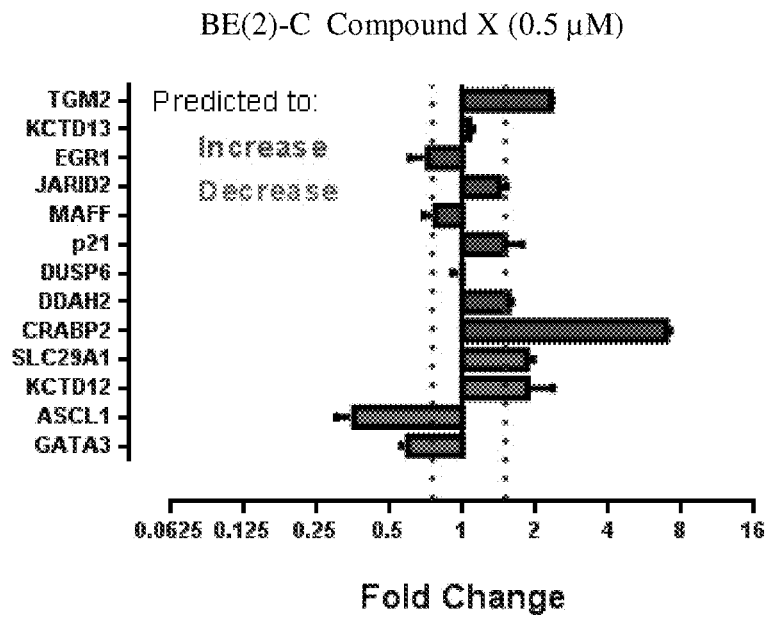
FIGS. 5A-C are a set of graphs that show the fold change of genes associated with maturation in BE(2)-C neuroblastoma cells upon treatment for 4 days with Compound X at 0.5 μM (FIG. 5A), 1 μM (FIG. 5B), and 3 μM (FIG. 5C).
Figure 5B:
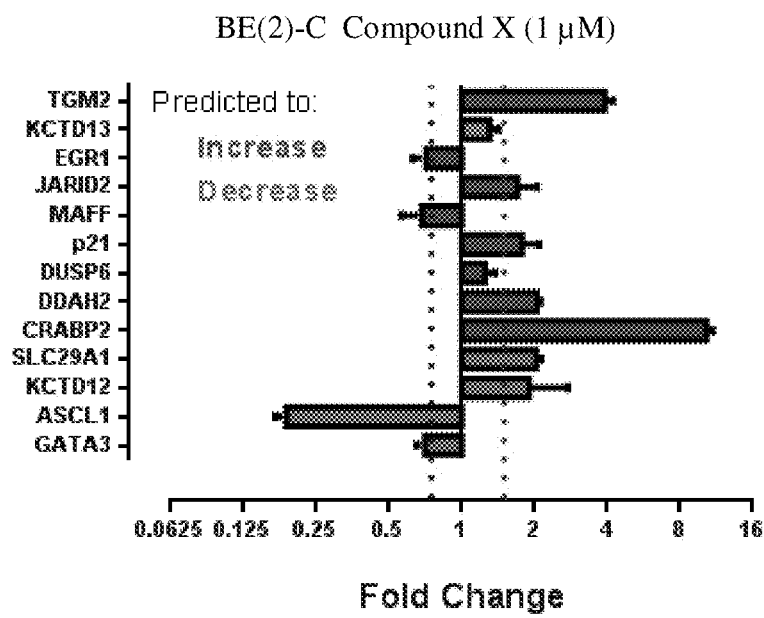
Figure 5C:
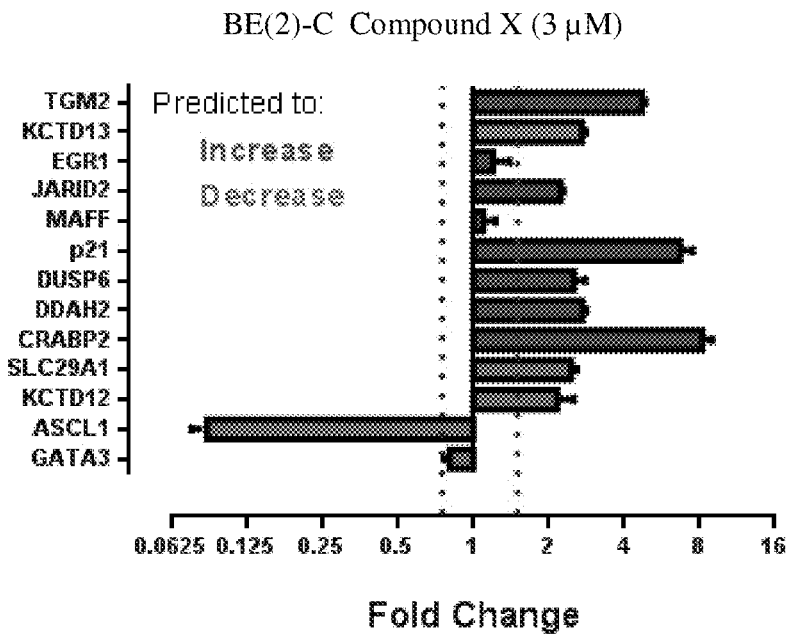
Figure 5D:
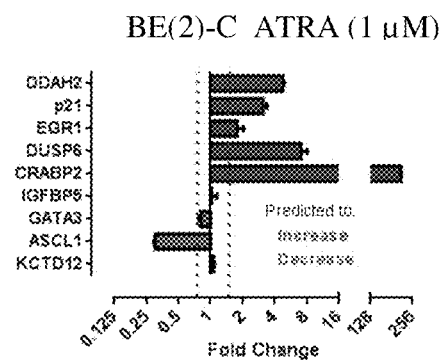
FIG. 5D shows the results of a positive control experiment in which BE(2)-C neuroblastoma cells were treated for 4 days with 1 μM ATRA (all trans retinoic acid).
Figure 5E:
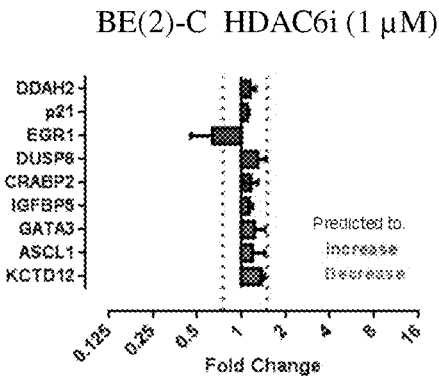
FIG. 5E shows the results of a negative control experiment in which BE(2)-C neuroblastoma cells were treated for 4 days with 1 μM of a HDAC6 selective inhibitor.

In one set of experiments, BE(2)-C neuroblastoma cells were treated for 4 days with Compound X at 0.5 µM (FIG. 5A), 1 µM (FIG. 5B), and 3 µM (FIG. 5C). Each of the experiments measured the fold change of various genes associated with maturation, such as TGM2, KCTD13, EGR1, JARID2, MAFF, p21, DUSP6, DDAH2, CRABP2, SLC29A1, KCTD12, ASCL1, and GATA3. FIG. 5D shows the results of a positive control experiment in which BE(2)-C cells were treated for 4 days with 1 µM ATRA (all trans retinoic acid). FIG. 5E shows the results of a negative control experiment in which BE(2)-C cells were treated with 1 µM of a HDAC6 selective inhibitor. The results of these experiments show that Compound X, a HDAC1/2 selective inhibitor, alters genes associated with maturation. The strongest effects were seen at 3 µM of compound.

Figure 6A:
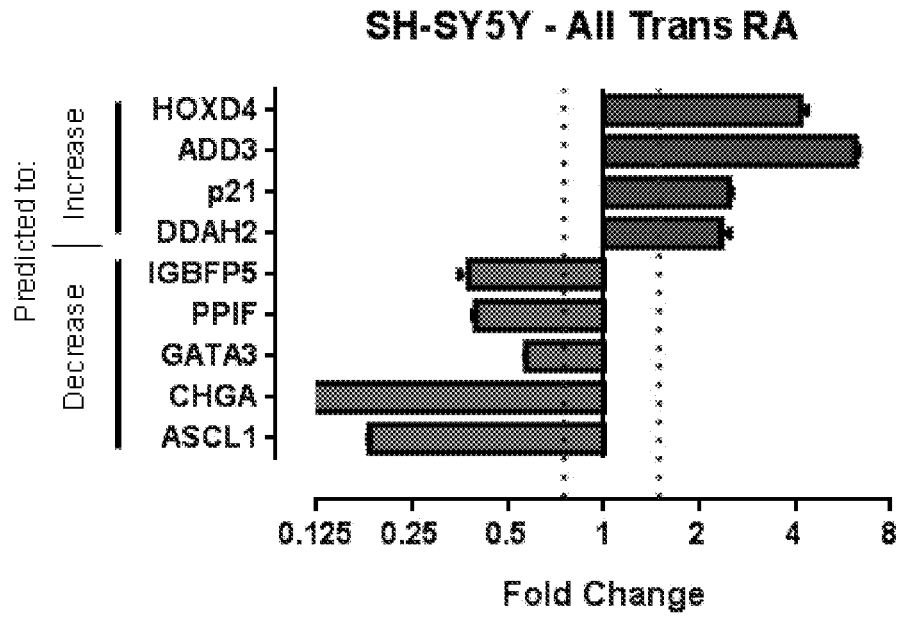
FIGS. 6A-D are a set of graphs that show the fold change of genes associated with maturation in SH-SY5Y neuroblastoma cells upon treatment for 72 hours with 1 μM of ATRA (all trans retinoic acid) (FIG. 6A), a HDAC6 selective inhibitor (FIG. 6B), Compound X (FIG. 6C), and another HDAC6 selective inhibitor (FIG. 6D).
Figure 6B:
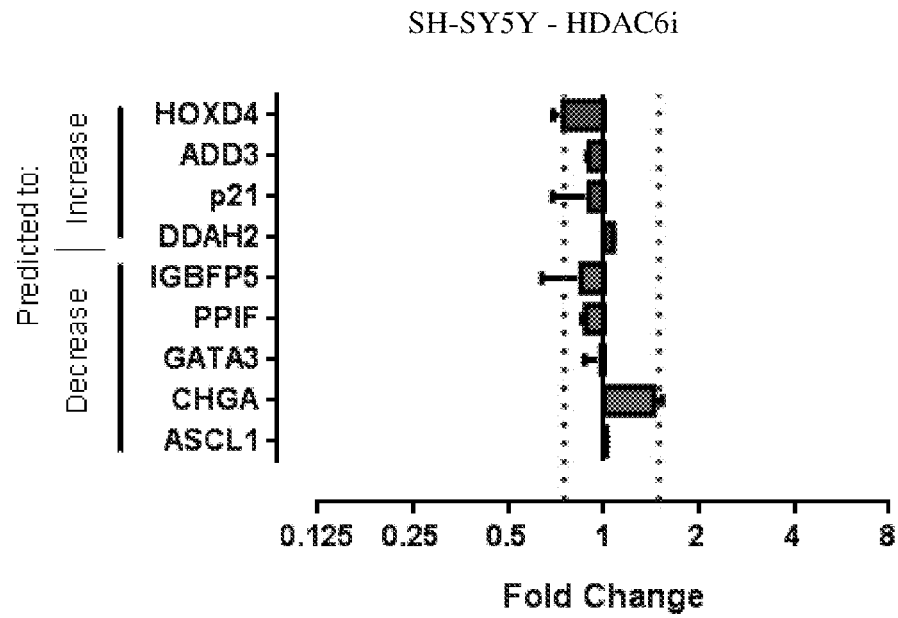
Figure 6C:
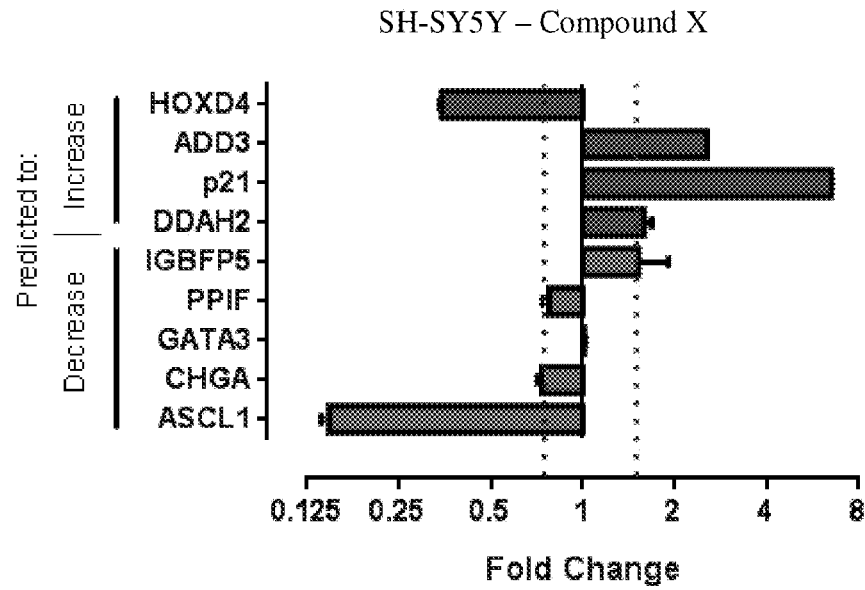
Figure 6D:
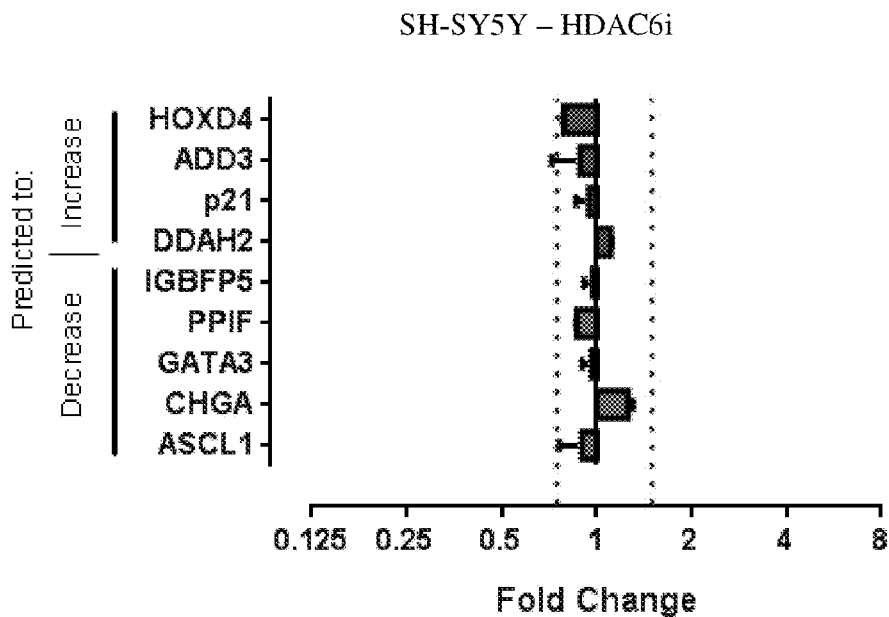

In another set of experiments, SH-SY5Y neuroblastoma cells were treated for 72 hours with 1 µM ATRA (all trans retinoic acid) (FIG. 6A), a HDAC6 selective inhibitor (FIG. 6B), Compound X (FIG. 6C), and another HDAC6 selective inhibitor (FIG. 6D). Each of the experiments measured the fold change of various genes associated with maturation, such as HOXD4, ADD3, p21, DDAH2, IGBFP5, PPIF, GATA3, CHGA, and ASCL1. Table 4 below shows the $IC_{50}$s in nM of the various compounds.

TABLE 4

|  | HDAC1 | HDAC2 | HDAC3 | HDAC6 |
|---|---|---|---|---|
| HDAC6i | 2123 | 2570 | 11223 | 7 |
| another HDAC6i | 33 | 54 | 61 | 5 |
| Compound X | 6 | 36 | 445 | — |

The results of these experiments show that Compound X, a HDAC1/2 selective inhibitor, alters genes associated with maturation.

Figure 7A:
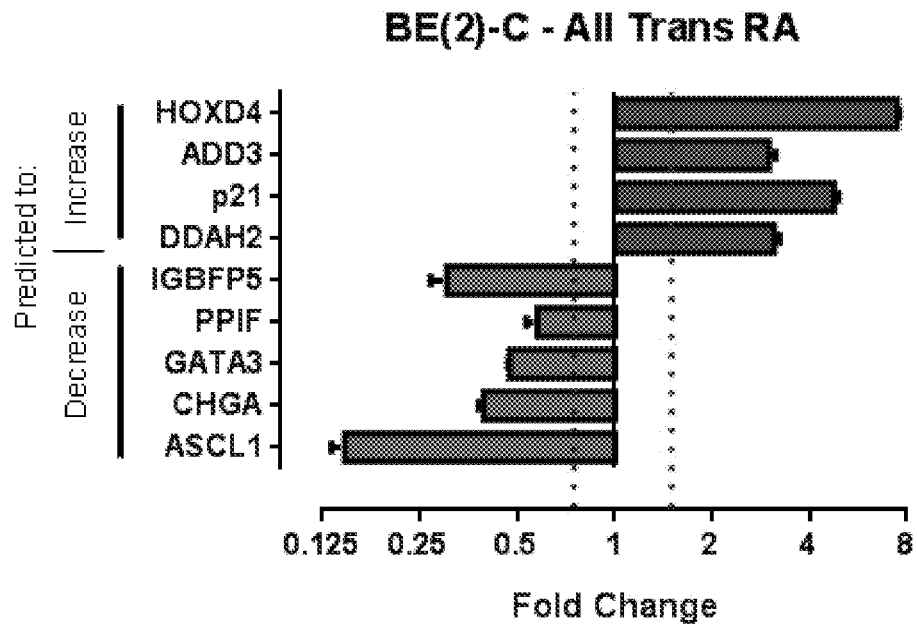
FIGS. 7A-D are a set of graphs that show the fold change of genes associated with maturation in BE(2)-C neuroblastoma cells upon treatment for 72 hours with 1 μM of ATRA (all trans retinoic acid) (FIG. 7A), a HDAC6 selective inhibitor (FIG. 7B), Compound X (FIG. 7C), and another HDAC6 selective inhibitor (FIG. 7D).
Figure 7B:
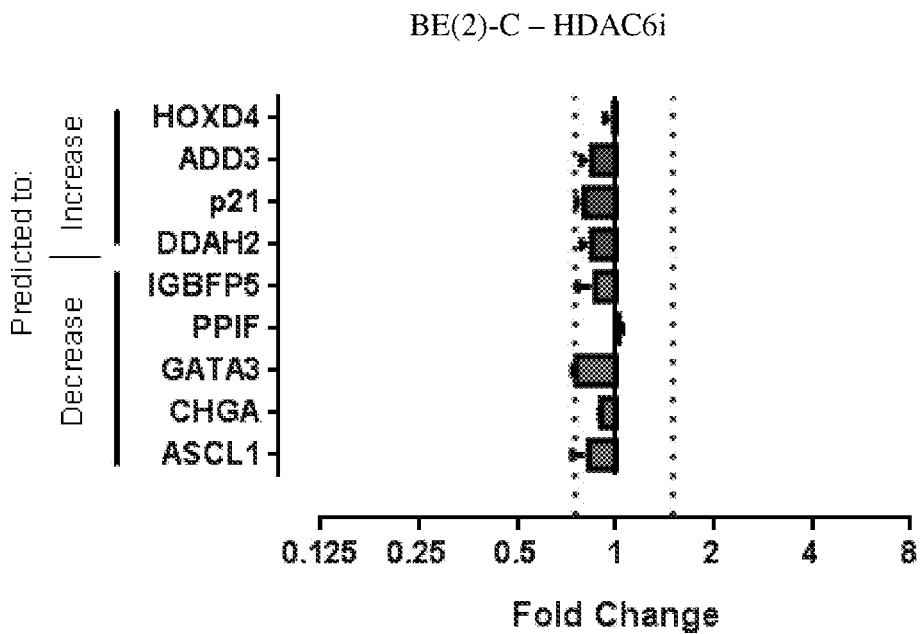
Figure 7C:
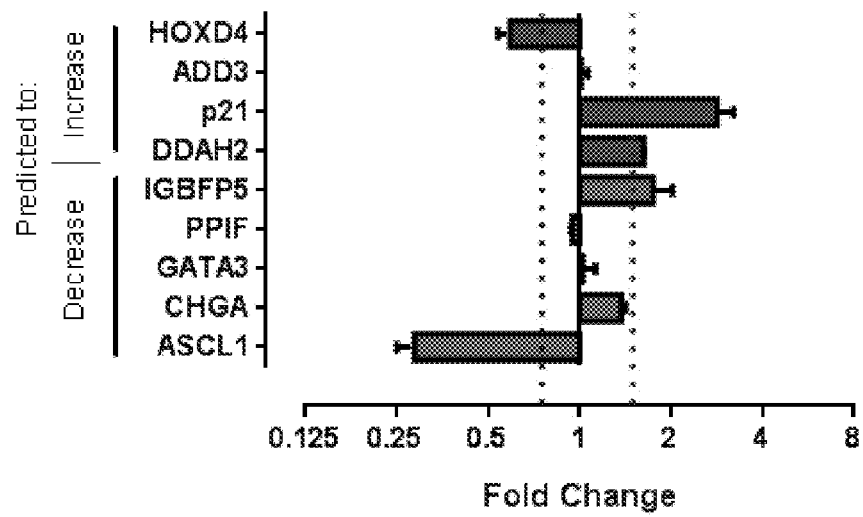
Figure 7D:
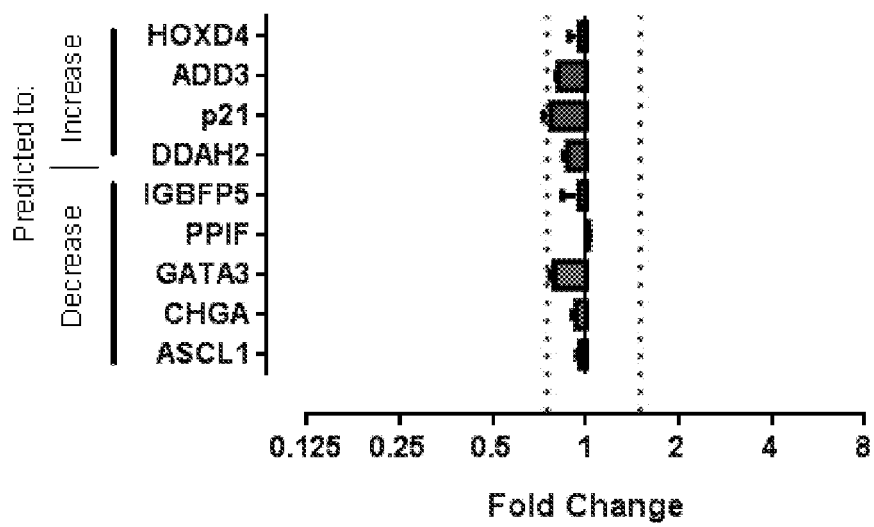

In yet another set of experiments, BE(2)-C neuroblastoma cells were treated for 72 hours with 1 µM ATRA (all trans retinoic acid) (FIG. 7A), a HDAC6 selective inhibitor (FIG. 7B), Compound X (FIG. 7C), and another HDAC6 selective inhibitor (FIG. 7D). Each of the experiments measured the fold change of various genes associated with maturation, such as HOXD4, ADD3, p21, DDAH2, IGBFP5, PPIF, GATA3, CHGA, and ASCL1. Table 5 below shows the $IC_{50}$s in nM of the various compounds.

TABLE 5

|  | HDAC1 | HDAC2 | HDAC3 | HDAC6 |
|---|---|---|---|---|
| HDAC6i | 2123 | 2570 | 11223 | 7 |
| another HDAC6i | 33 | 54 | 61 | 5 |
| Compound X | 6 | 36 | 445 | — |

The results of these experiments show that Compound X, a HDAC1/2 selective inhibitor, alters genes associated with maturation.

Figure 8A:
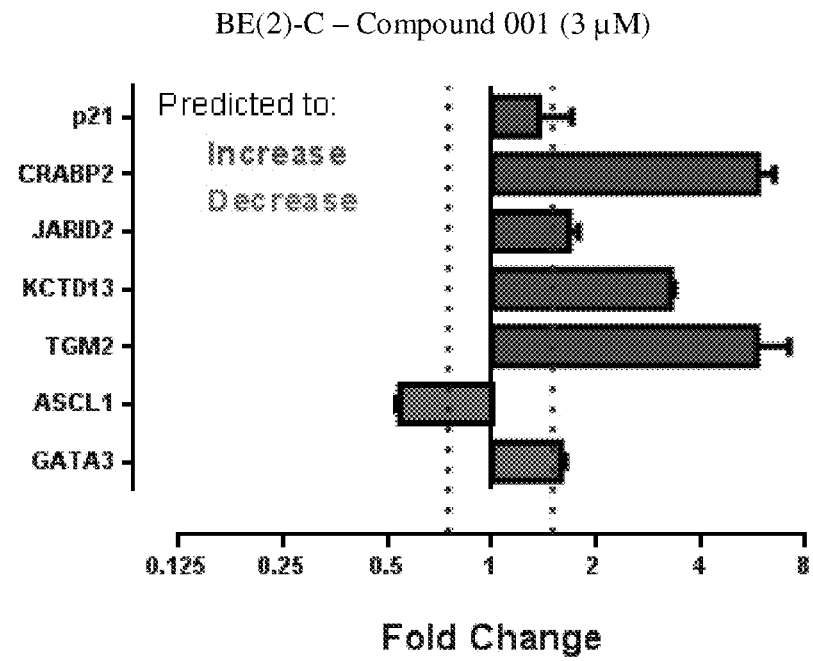
FIGS. 8A-C are a set of graphs that show the fold change of genes associated with maturation.
Figure 8B:
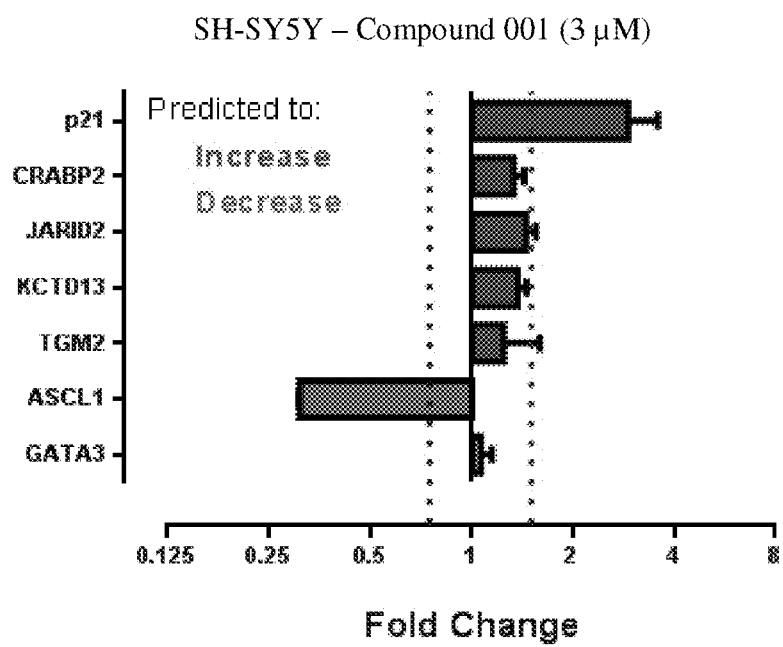
Figure 8C:
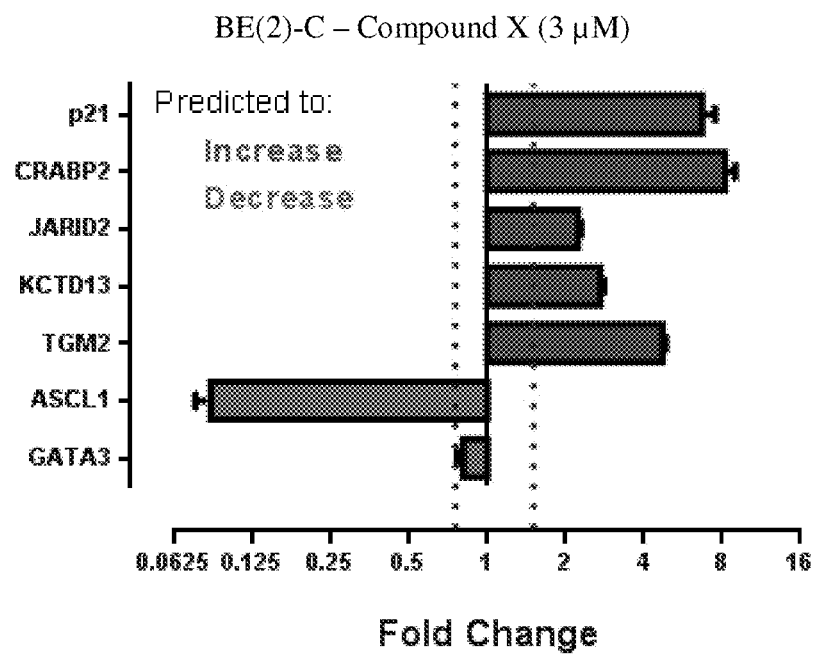

In another set of experiments, the fold change of genes associated with maturation were assessed. In one experiment, BE(2)-C neuroblastoma cells were treated for 2 days with 3 µM Compound 001 (FIG. 8A). In a second experiment, SH-SY5Y neuroblastoma cells were treated for 2 days with 3 µM Compound 001 (FIG. 8B). In a third experiment, BE(2)-C neuroblastoma cells were treated for 2 days with 3 µM Compound X (FIG. 8C). Each of the experiments measured the fold change of various genes associated with maturation, such as p21, CRABP2, JARID2, KCTD13, TGM2, ASCL1, and GATA3. The results of these experiments show that Compound 001, a HDAC1/2/6 selective inhibitor, induces gene expression changes that are consistent with maturation.

Figure 9A:
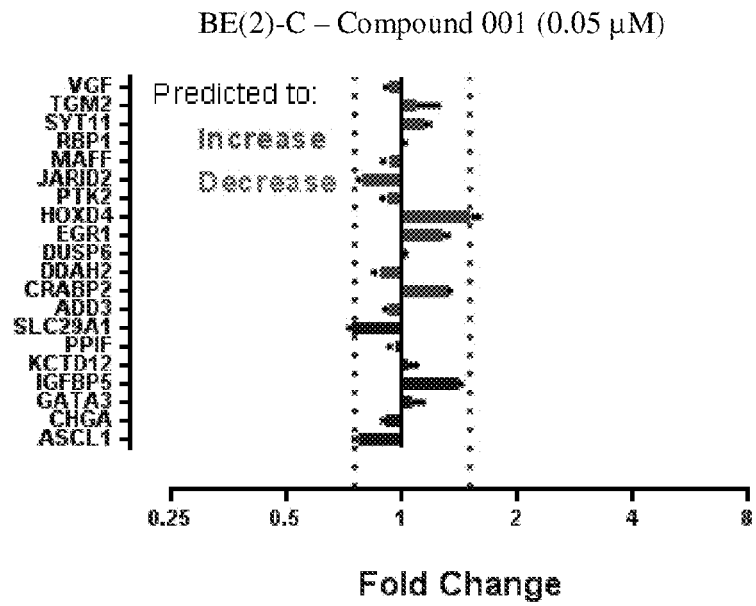
FIGS. 9A-C are a set of graphs that show the fold change of genes associated with maturation in BE(2)-C neuroblastoma cells upon treatment for 48 hours with Compound 001 at 0.5 μM (FIG. 9A), 2 μM (FIG. 9B), and 4 μM (FIG. 9C).
Figure 9B:
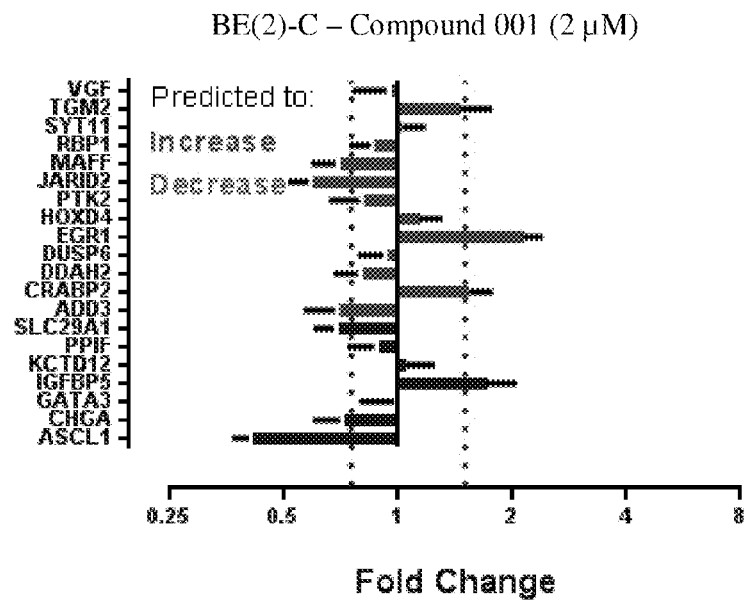
Figure 9C:
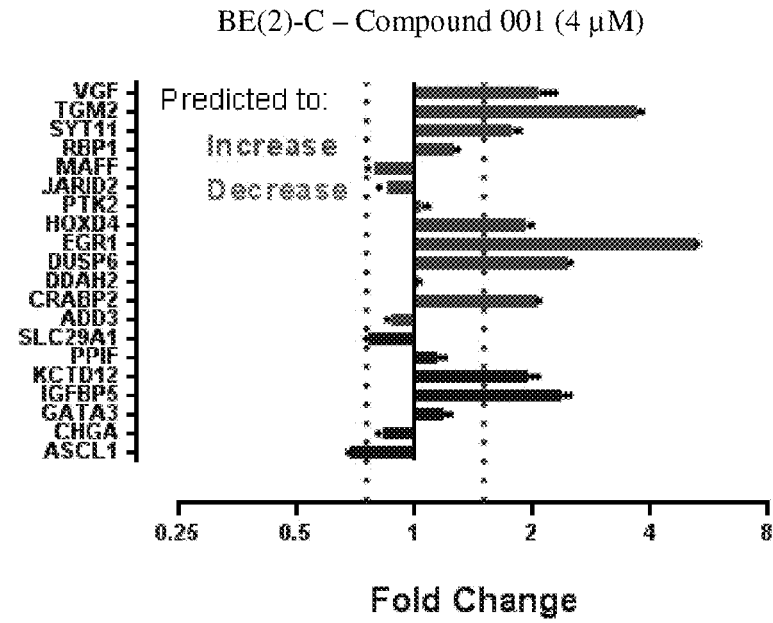
Figure 9D:
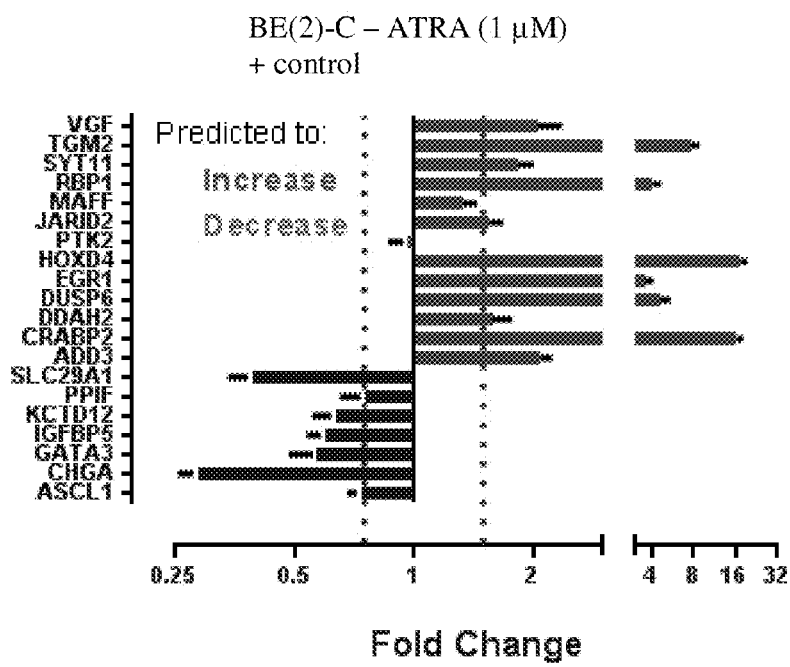
FIG. 9D is a graph that shows the results of a positive control experiment in which BE(2)-C neuroblastoma cells were treated for 48 hours with 1 μM ATRA (all trans retinoic acid).

In a set of experiments, BE(2)-C neuroblastoma cells were treated for 48 hours with Compound 001 at 0.5 µM (FIG. 9A), 2 µM (FIG. 9B), and 4 µM (FIG. 9C). FIG. 9D shows the results of a positive control experiment in which BE(2)-C cells were treated for 48 hours with 1 µM ATRA (all trans retinoic acid). Each of the experiments measured the fold change of various genes associated with maturation, such as VGF, TGM2, SYT11, RBP1, MAFF, JARID2, PTK2, HOXD4, EGR1, DUSP6, DDAH2, CRABP2, ADD3, SLC29A1, PPIF, KCTD12, IGFBP5, GATA3, CHGA, and ASCL1. The results of these experiments show that Compound 001 induces gene expression changes consistent with maturation at 4 µM, but not at 2 µM or less. HDAC2glo assay data suggest maximal HDAC2 inhibition was reached at 3-4 µM.

Figure 10A:
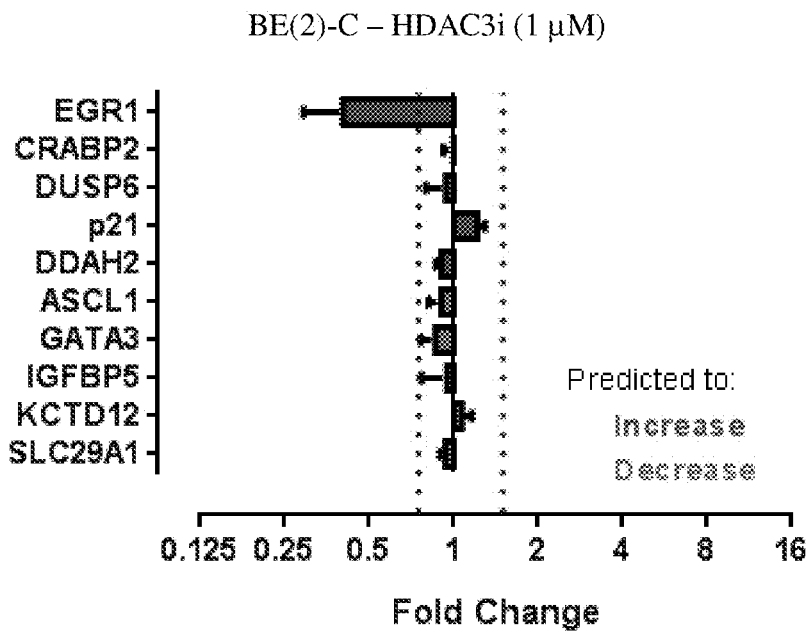
FIGS. 10A-C are a set of graphs that show the fold change of genes associated with maturation in BE(2)-C neuroblastoma cells upon treatment for 4 days with a HDAC3 selective inhibitor at 1 μM (FIG. 10A), 0.5 μM (FIG. 10B), and 3 μM (FIG. 10C).
Figure 10B:
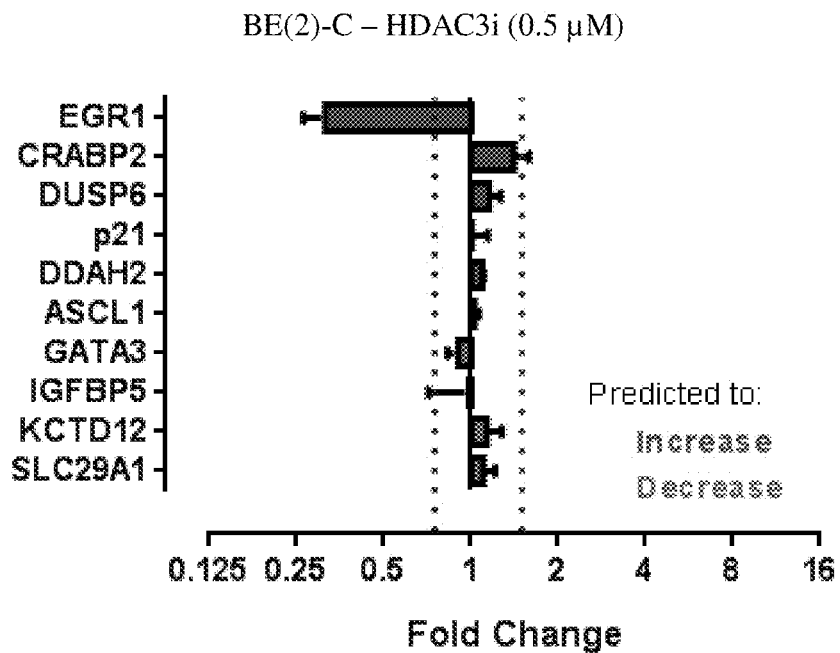
Figure 10C:
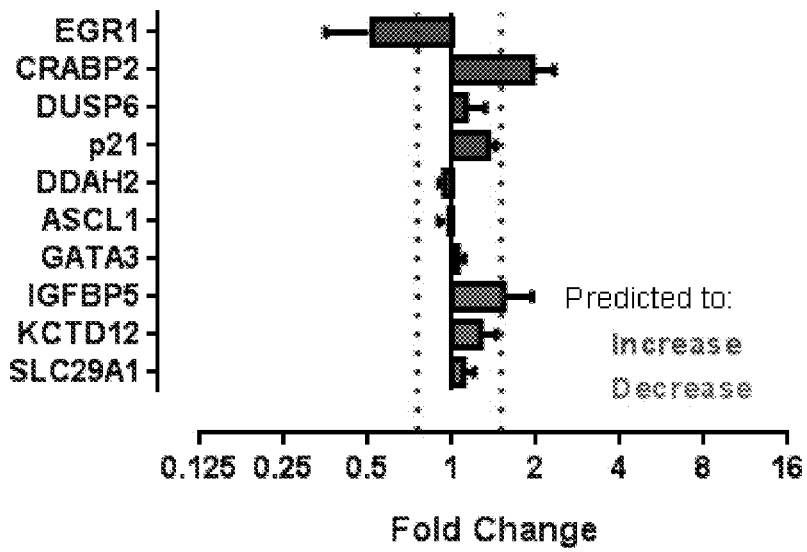
Figure 10D:
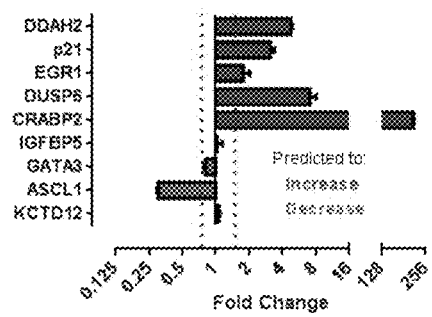
FIG. 10D shows the results of a positive control experiment in which BE(2)-C neuroblastoma cells were treated for 4 days with 1 μM ATRA (all trans retinoic acid).
Figure 10E:
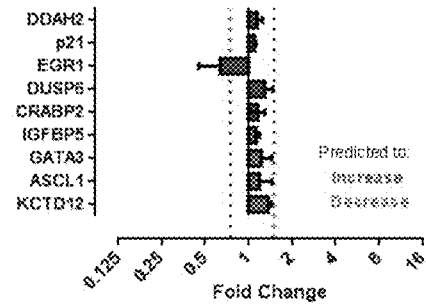
FIG. 10E shows the results of a negative control experiment in which BE(2)-C neuroblastoma cells were treated for 4 days with 1 μM of a HDAC6 selective inhibitor.

A set of experiments shows that a HDAC3 selective inhibitor fails to modulate genes associated with maturation. BE(2)-C neuroblastoma cells were treated for 4 days with a HDAC3 selective inhibitor at 1 µM (FIG. 10A), 0.5 µM (FIG. 10B), and 3 µM (FIG. 10C). Each of the experiments measured the fold change of various genes associated with maturation, such as EGR1, CRABP2, DUSP6, p21, DDAH2, ASCL1, GATA3, IGFBP5, KCTD12, and SLC29A1. FIG. 10D shows the results of a positive control experiment in which BE(2)-C neuroblastoma cells were treated for 4 days with 1 µM ATRA (all trans retinoic acid). FIG. 10E shows the results of a negative control experiment in which BE(2)-C neuroblastoma cells were treated for 4 days with 1 µM of a HDAC6 selective inhibitor. The results of these experiments show that a HDAC3 selective inhibitor did not alter gene expression in a manner consistent with neuroblastoma maturation. In addition, the dose response was modest, if present at all.

Figure 11A:
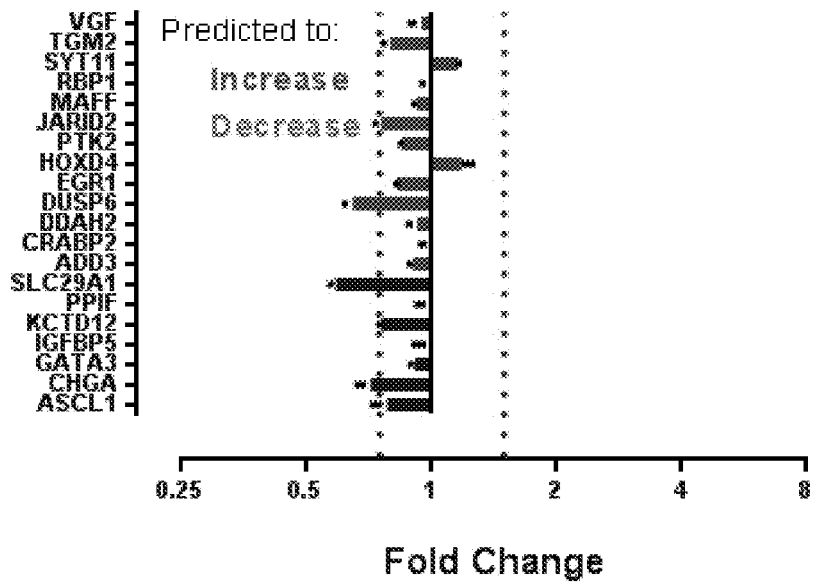
FIGS. 11A-C are a set of graphs that show the fold change of genes associated with maturation in BE(2)-C neuroblastoma cells upon treatment for 48 hours with a HDAC6 selective inhibitor at 0.5 μM (FIG. 11A), 2 μM (FIG. 11B), and 4 μM (FIG. 11C).
Figure 11B:
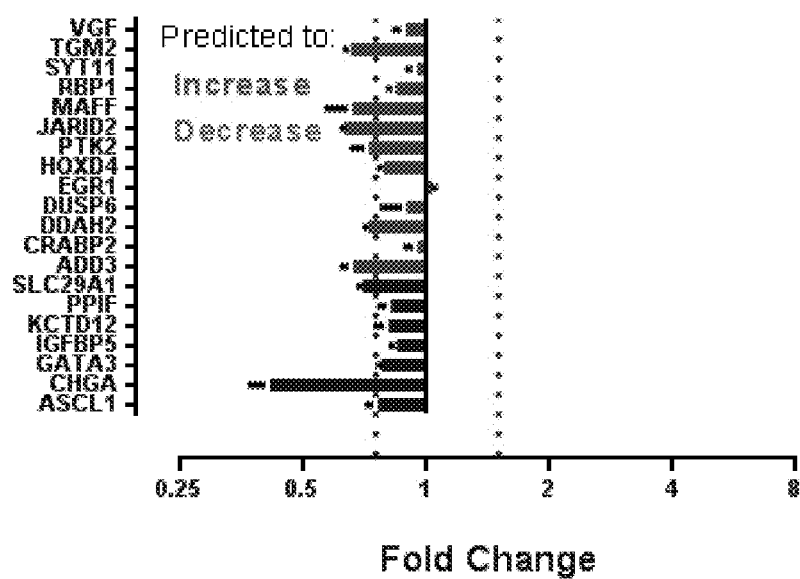
Figure 11C:
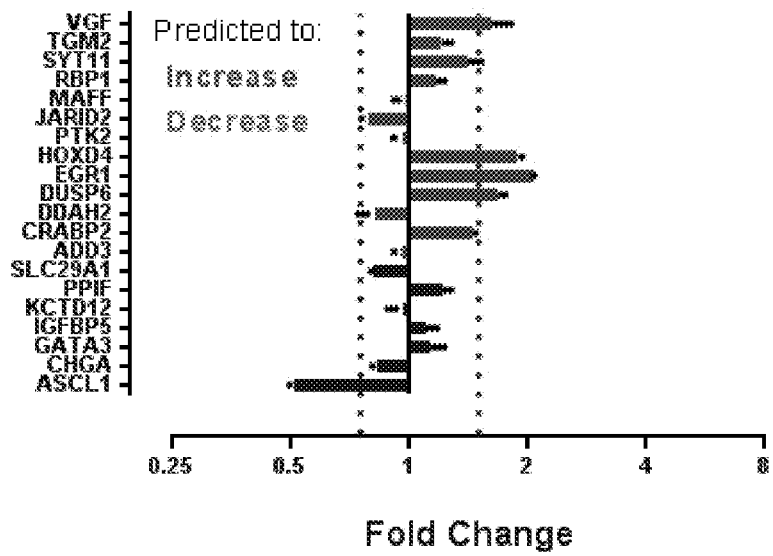
Figure 11D:
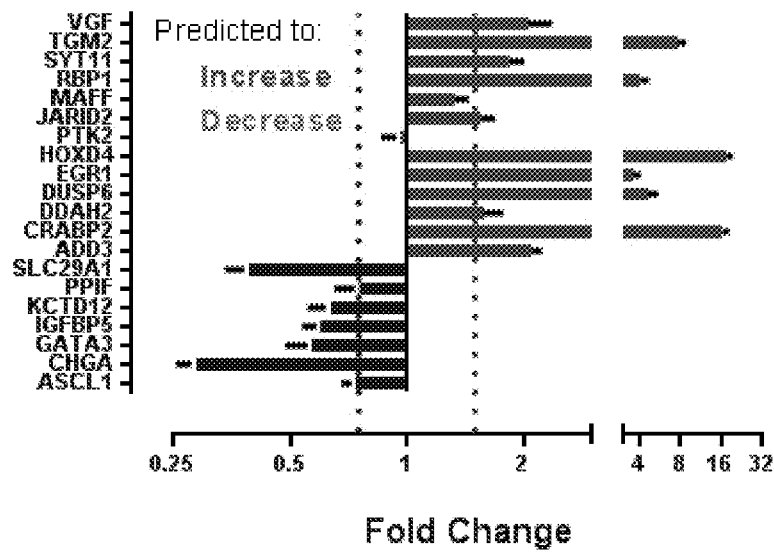
FIG. 11D shows the results of a positive control experiment in which BE(2)-C neuroblastoma cells were treated for 48 hours with 1 μM ATRA (all trans retinoic acid).

A set of experiments shows that a HDAC6 selective inhibitor fails to modulate genes associated with maturation. BE(2)-C neuroblastoma cells were treated for 48 hours with HDAC6 selective inhibitor at 0.5 µM (FIG. 11A), 2 µM (FIG. 11B), and 4 µM (FIG. 11C). FIG. 11D shows the results of a positive control experiment in which BE(2)-C neuroblastoma cells were treated for 48 hours with 1 µM ATRA (all trans retinoic acid). Each of the experiments measured the fold change of various genes associated with maturation, such as VGF, TGM2, SYT11, RBP1, MAFF, JARID2, PTK2, HOXD4, EGR1, DUSP6, DDAH2, CRABP2, ADD3, SLC29A1, PPIF, KCTD12, IGFBP5, GATA3, CHGA, and ASCL1. The results of these experiments show that a HDAC6 selective inhibitor failed to robustly induce gene changes consistent with maturation, even at 4 µM of exposure. These results are consistent with a previous experiment where maturation was not evident after 1 µM of treatment.

Example 39

HDAC1/2 Inhibition Induces Increased Sub-G1 Cell Populations at a Concentration where Maturation is Occurring The following is a quick summary of the neuroblastoma cell cycle experiments. Adherent cells were plated into 12-well plates at $10^6$ cells/well and allowed to adhere for 2-4 hours. Compounds were dispensed in DMSO at the indicated concentrations using an automated liquid handling system (Tecan D300) and incubated for the indicated times at 37° C. with 5% $CO_2$. Cells were harvested with enzyme-free cell disassociation solution and washed with buffered saline. Cells were fixed overnight with 100% ethanol. Cell cycle was assessed by flow cytometry using the Molecular Probes FxCycle PI/RNase Staining Solution kit according to manufacture protocols.

The protocol for the cell cycle experiments was as follows. The day before the experiment, the cells were fed in the flask by doubling the media. Then, the cells were harvested by adding non-enzymatic cell dissociation media and incubating at 37° C. for 15 minutes. Next, the cells were transferred to a 50 ml tube and pipet to create a single-cell suspension. The cells were then washed with PBS buffer. Then, the cells were resuspended in complete media at $5 \times 10^5$ cells per ml. Next, 2 ml of cells were transferred to 12-well plates. Then, the treatment compounds were dispensed into each well using the D300 liquid handler. The cells were incubated for the indicated time at 37° C. Then, the cells were harvested by adding 500 µl enzyme free cell dissociation solution and incubating at 37° C. for 15 minutes. Next, the cells were spun into a pellet and then washed with PBS. Then, 500 µl 100% EtOH was added and incubated at 4° C. overnight. Then, the cells were washed 3× with PBS. The cells were then resuspended in 500 ml FxCycle PI/RNase solution, and incubated for 2-4 hours at room temperature. Finally, the cells were assayed by flow cytometry.

Figure 12A:
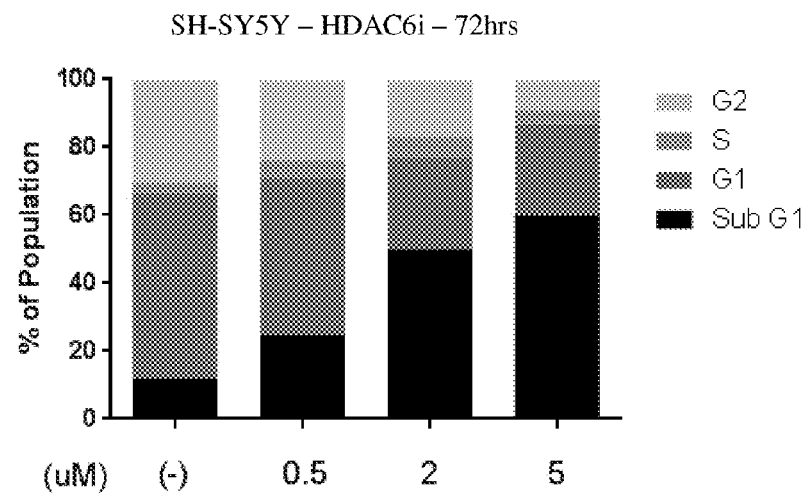
FIGS. 12A-D are a set of graphs that show that selective HDAC inhibitors alter cell cycle progression in neuroblastoma cells.
Figure 12B:
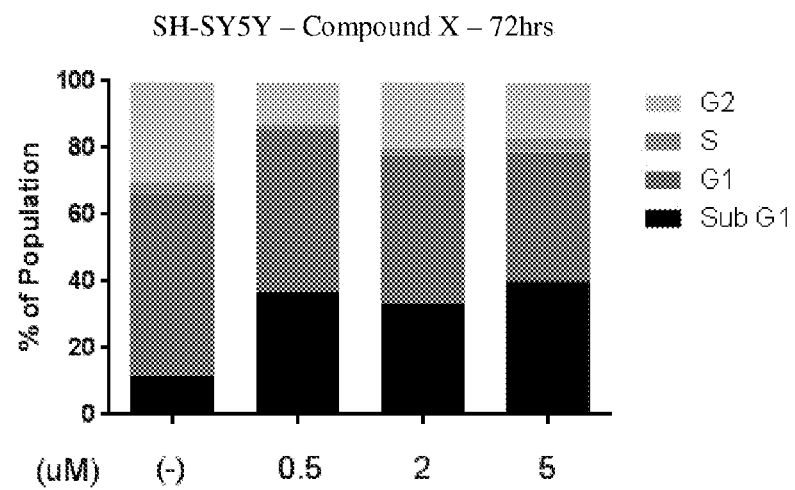
Figure 12C:
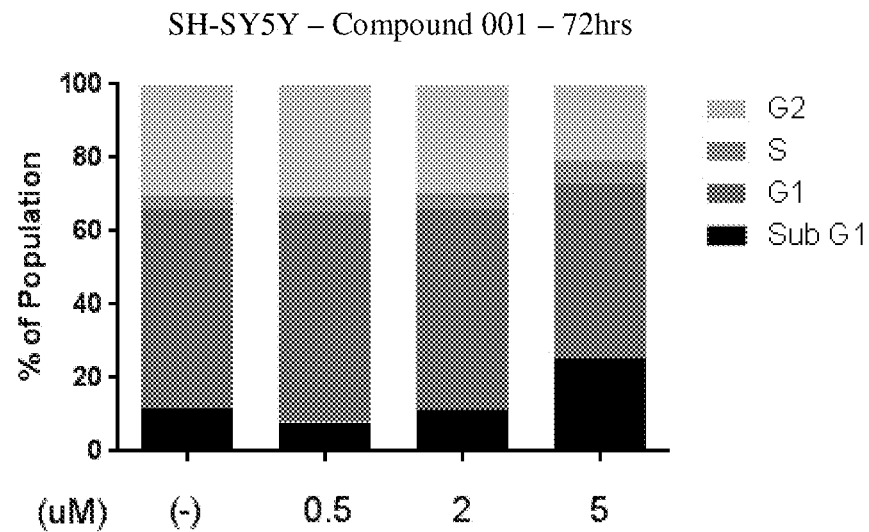
Figure 12D:
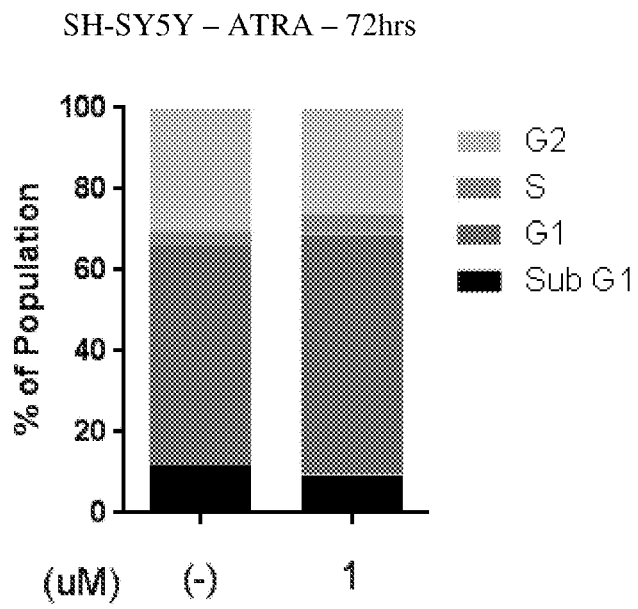
Figure 13A:
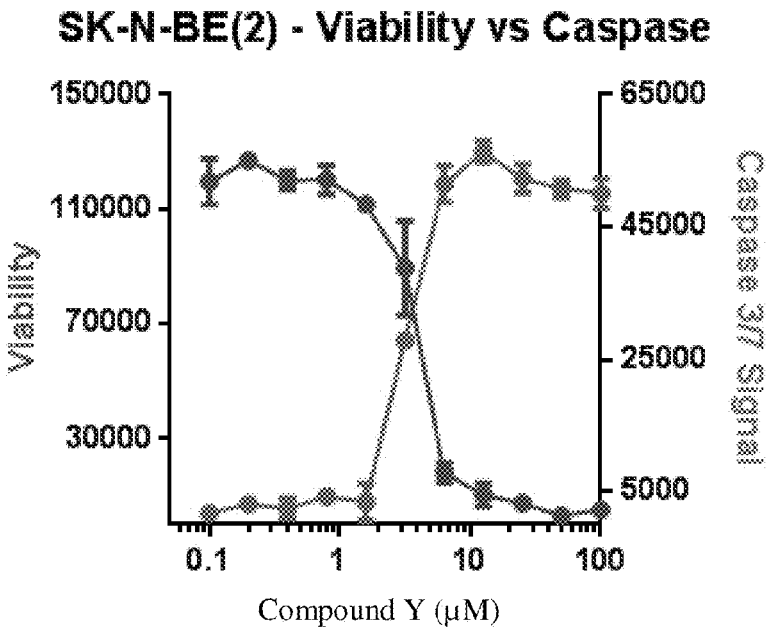
FIGS. 13A-D are a set of graphs that show that selective HDAC inhibitors decrease neuroblastoma viability and survival.
Figure 13B:
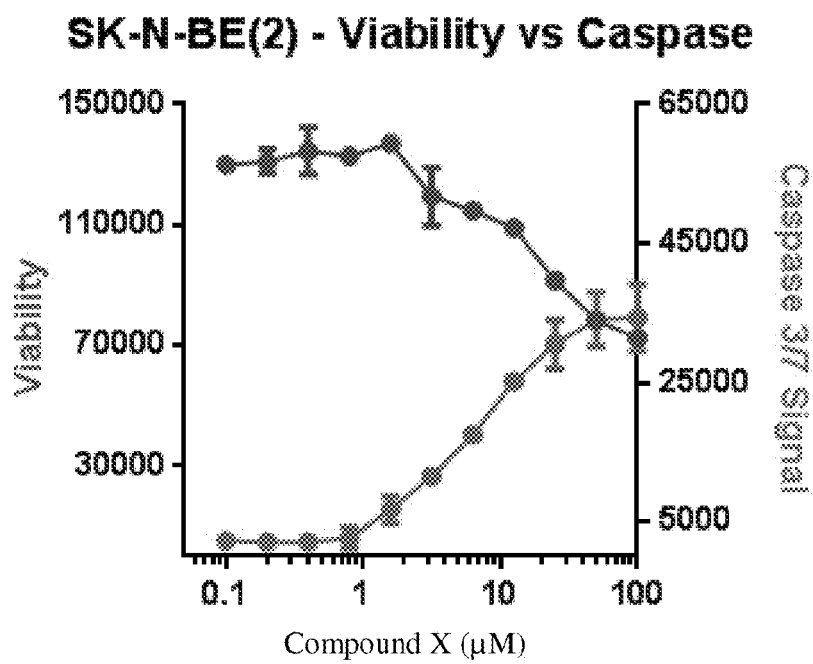
Figure 13C:
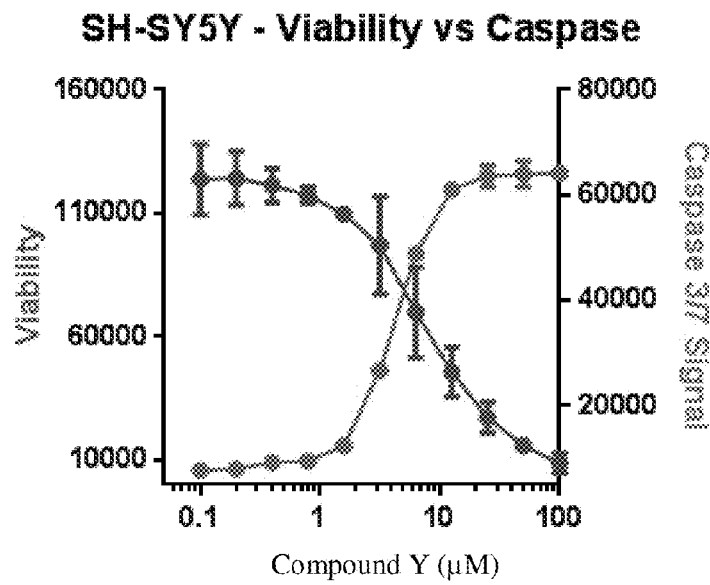
Figure 13D:
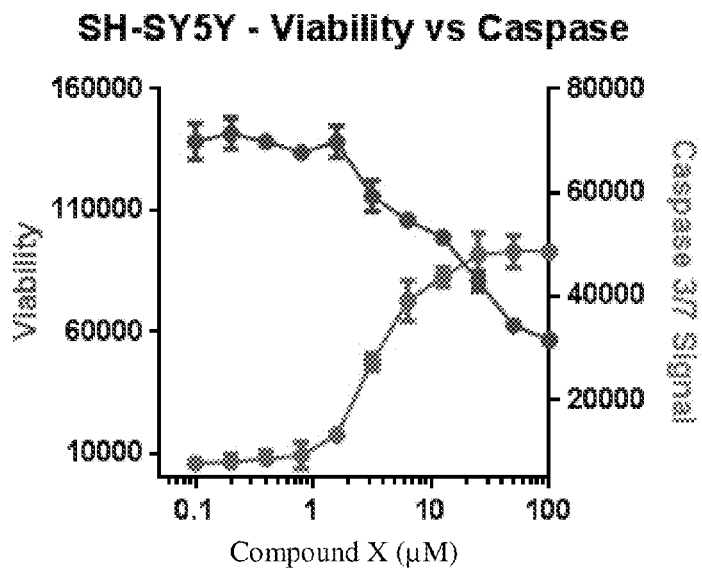
Figure 14A:
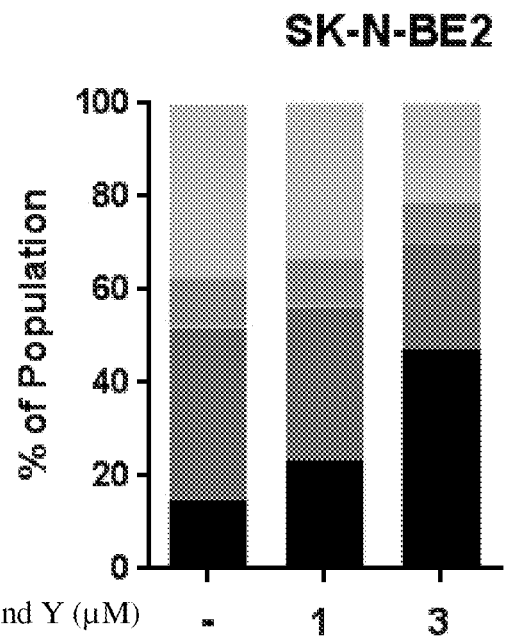
FIGS. 14A-D are a set of graphs that show that selective HDAC inhibitors decrease neuroblastoma viability and survival.
Figure 14B:
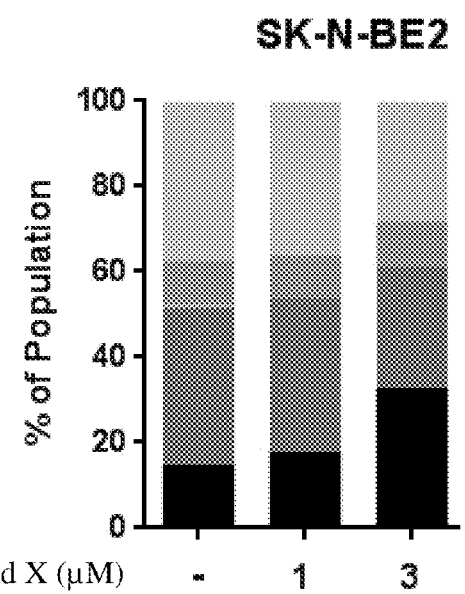
Figure 14C:
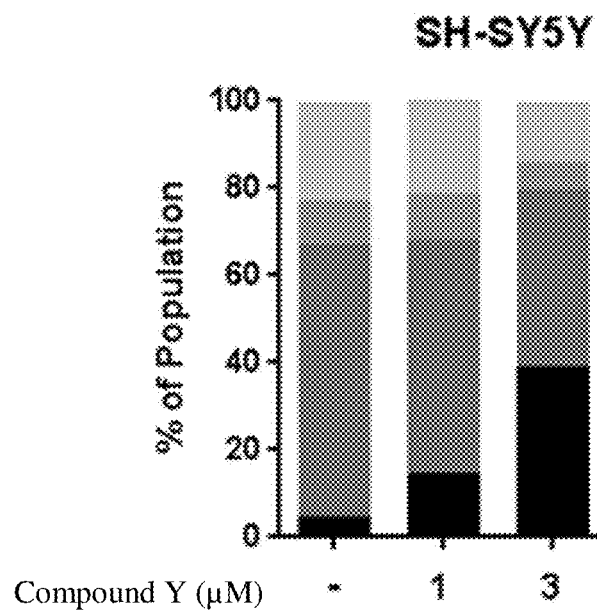
Figure 14D:
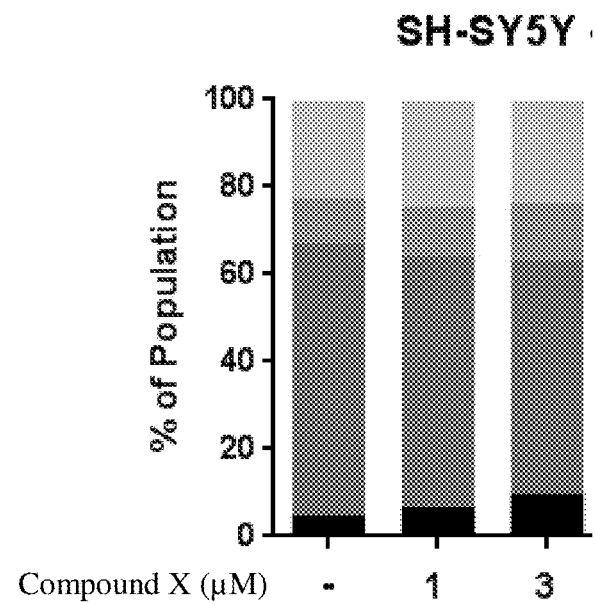
Figure 15A:
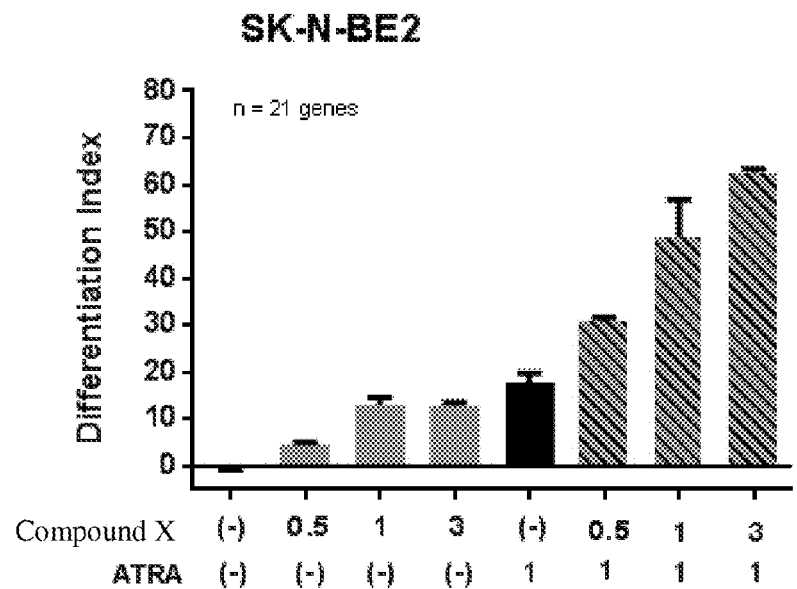
FIGS. 15A-D are a set of graphs that show that selective HDAC inhibitors drive neuroblastoma cells to differentiate.
Figure 15B:
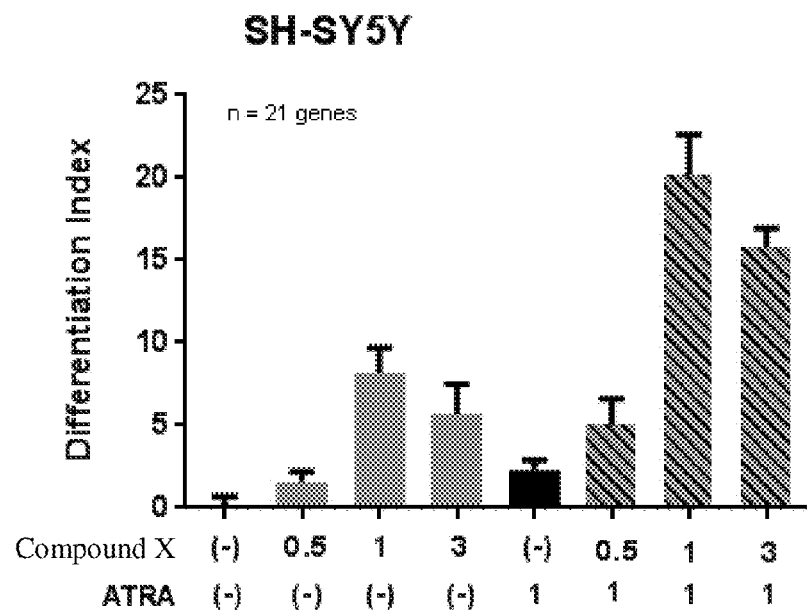
Figure 15C:
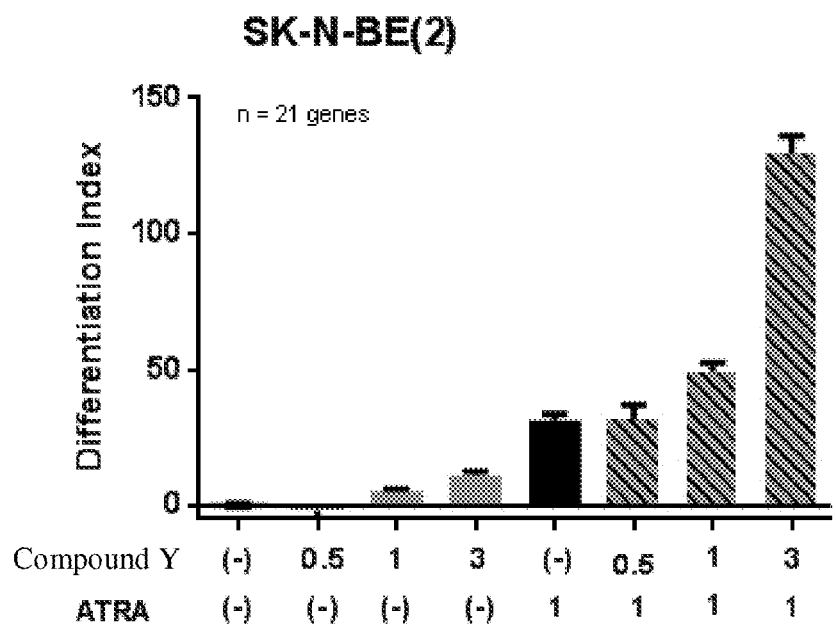
Figure 15D:
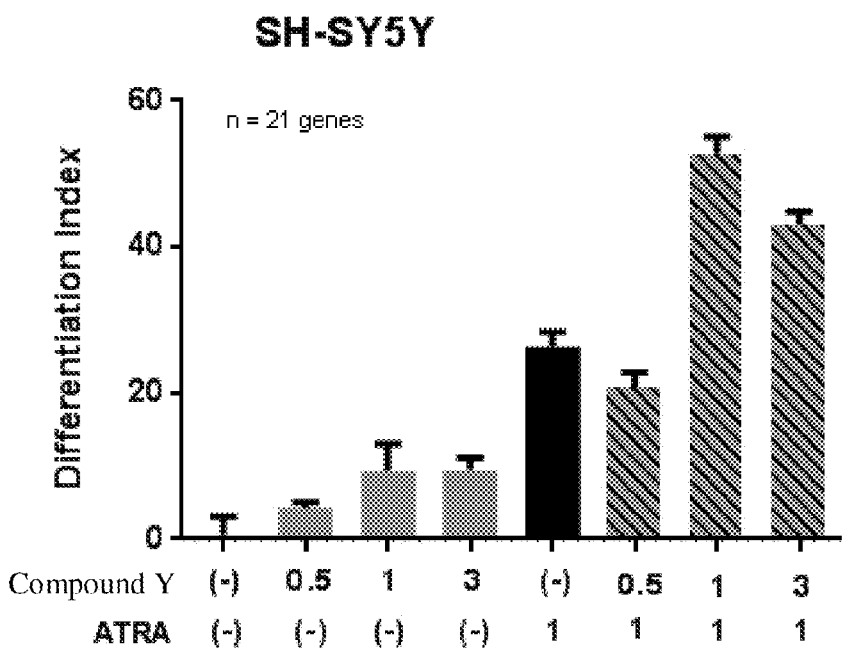

This set of experiments shows that selective HDAC inhibition alters cell cycle progression in neuroblastoma cells. In a first experiment, SH-SY5Y neuroblastoma cells were treated for 72 hours with 0, 0.5, 2, and 5 µM of a HDAC6 selective inhibitor (FIG. 12A). In a second experiment, SH-SY5Y neuroblastoma cells were treated for 72 hours with 0, 0.5, 2, and 5 µM Compound X (FIG. 12B). In a third experiment, SH-SY5Y neuroblastoma cells were treated for 72 hours with 0, 0.5, 2, and 5 µM Compound 001 (FIG. 12C). In a control experiment, SH-SY5Y neuroblastoma cells were treated for 72 hours with 0 and 1 µM ATRA (all trans retinoic acid) (FIG. 12D). Each of the experiments looked at the percent of the cell population in the G2 phase, S phase, G1 phase, and Sub G1 phase. The results of this experiment show that Compound 001 induced a reduction in G1/G2 and increase in sub-G1 at concentrations where maturation was observed. Also, Compound X induced similar cell cycle changes in all treatment groups, even at low doses associated with sub-optimal maturation. In addition, a HDAC6 selective inhibitor induced a dose-dependent decrease in G1/G2 with a corresponding increase in sub-G1. Finally, ATRA had little impact on cell cycle at concentrations associated with robust maturation at this time point.

Example 40

HDAC Inhibition Decreases Neuroblastoma Viability and Survival

SK-N-BE(2) or SH-SY5Y neuroblastoma cells were treated with varying concentrations of either Compound X or Compound Y. Viability and the Caspase 3/7 Signal were measured at 48 hours. The percentage of the population of the cells at various stages of the cell cycle were measured at 96 hours. See FIGS. 13A-D and FIGS. 14A-D. The results of these experiments show that low levels of apoptosis and cell death were detected at 48 hours after HDACi, the time when gene expression changes associated with differentiation were observed. An increase in the sub-G1 population became evident at 96 hours after treatment, indicating cell death at later times.

Example 41

HDAC Inhibition Drives Neuroblastoma Differentiation

SK-N-BE(2) or SH-SY5Y neuroblastoma cells were treated with varying concentrations of either Compound X or Y, and/or ATRA (all trans retinoic acid). The differentiation index was measured. See FIGS. 15A-D. The results of these experiments show that both Compound X and Compound Y induced an increase in the differentiation index, and the effect was markedly enhanced when an HDACi was combined with retinoic acid.

Example 42

HDAC Inhibition Enhances Low-Concentration ATRA

Figure 16A:
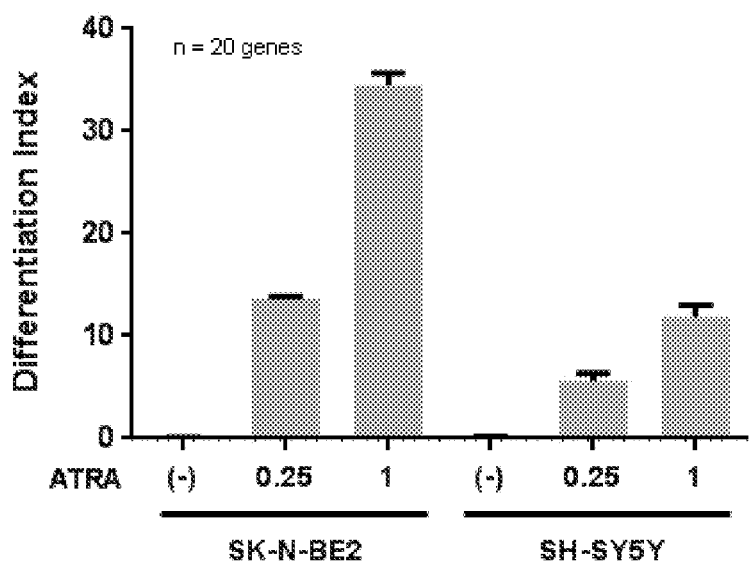
FIGS. 16A-C are a set of graphs that show that selective HDAC inhibitors enhance low-concentration ATRA.
Figure 16B:
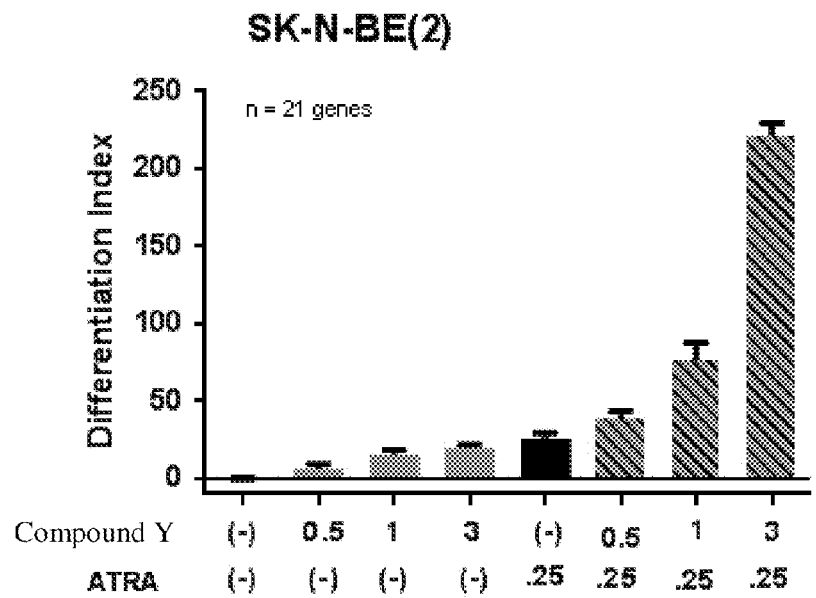
Figure 16C:
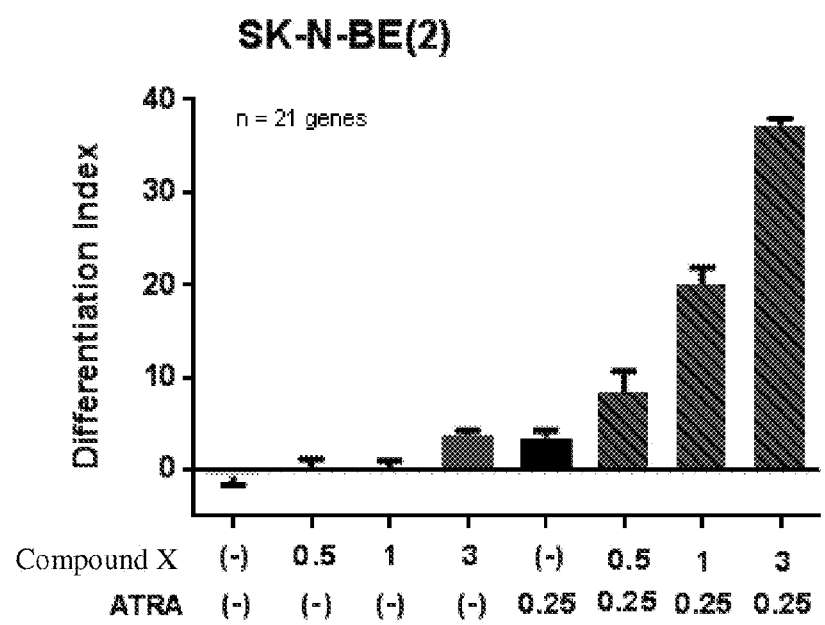
Figure 17A:
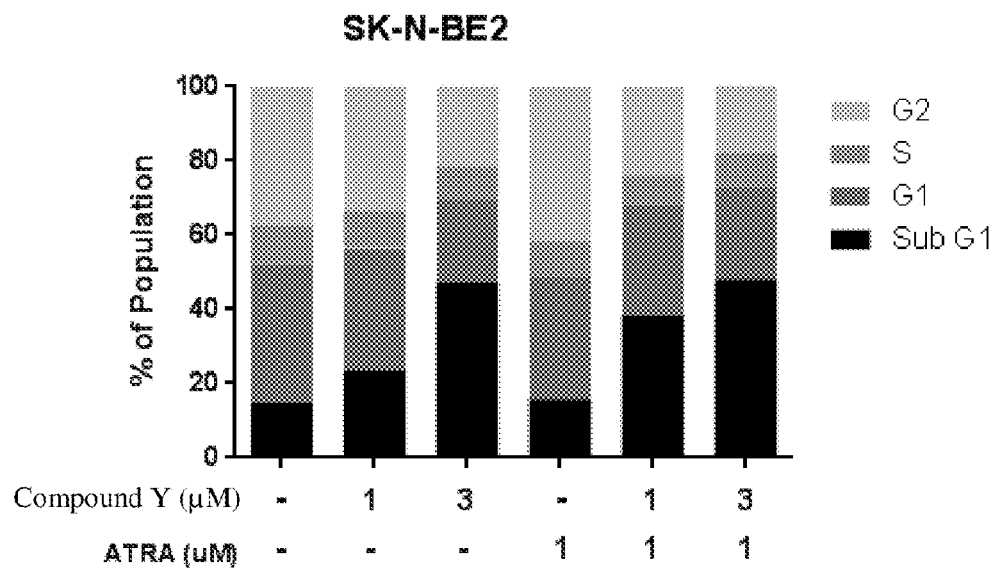
FIGS. 17A-D are a set of graphs that show that selective HDAC inhibitors induce cell cycle arrest in neuroblastoma cells.
Figure 17B:
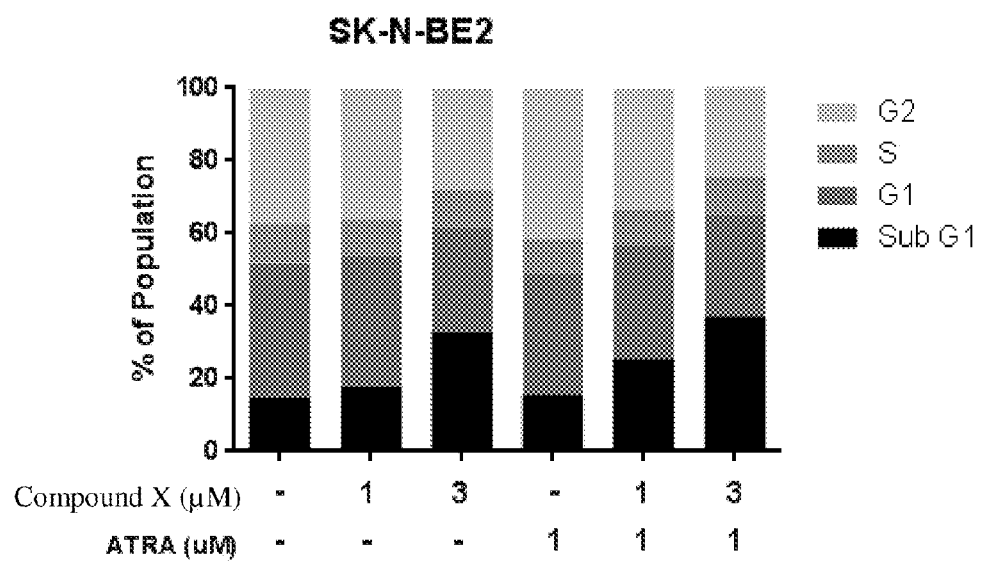
Figure 17C:
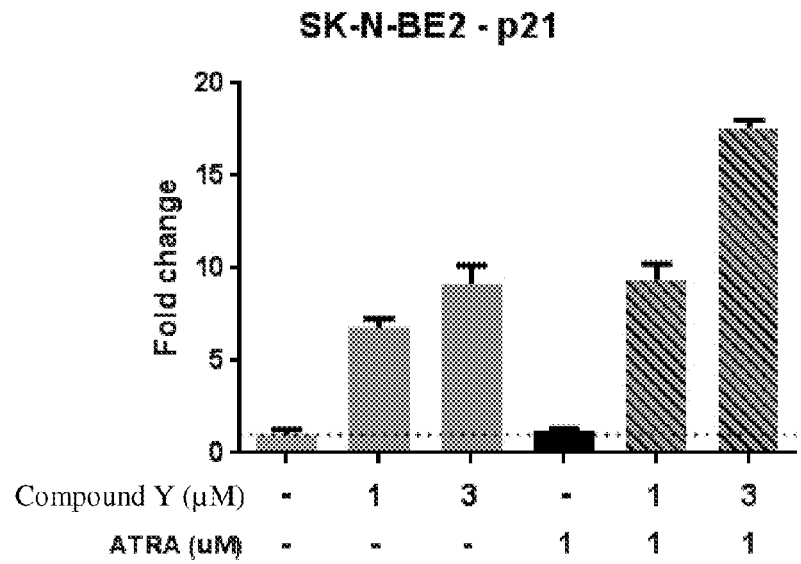
Figure 17D:
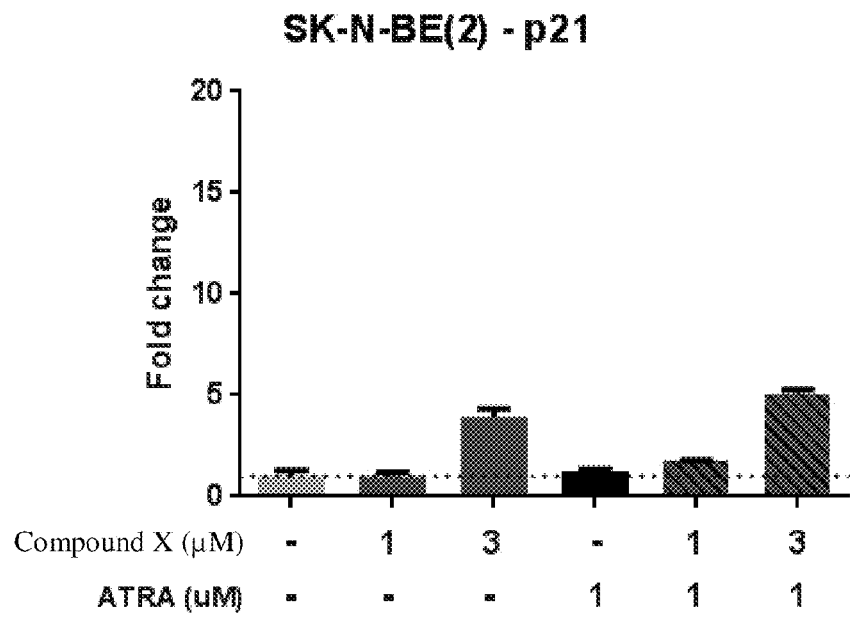
Figure 18A:
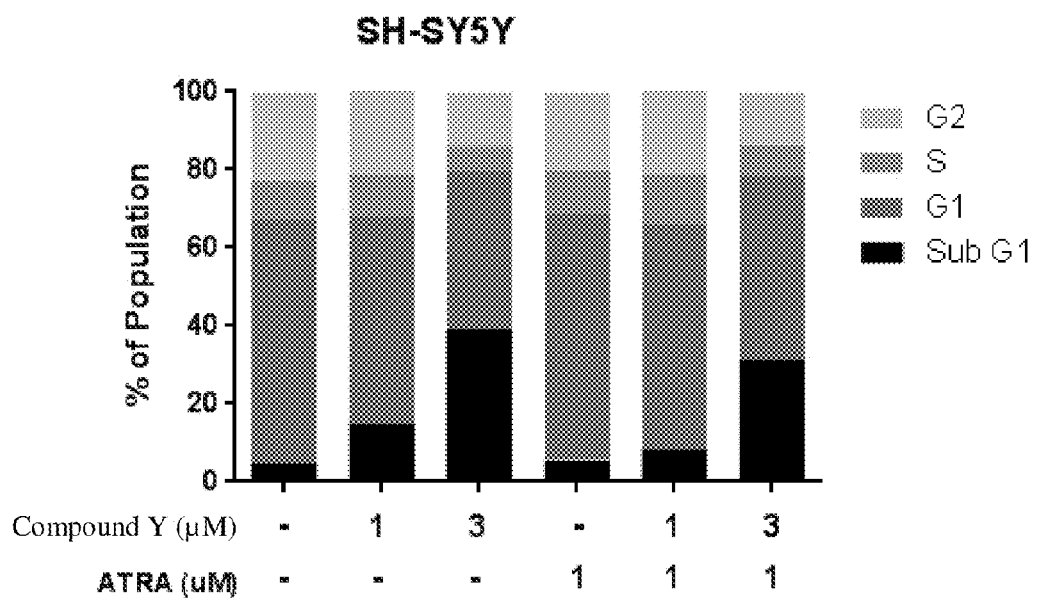
FIGS. 18A-D are a set of graphs that show that selective HDAC inhibitors induce cell cycle arrest in neuroblastoma cells.
Figure 18B:
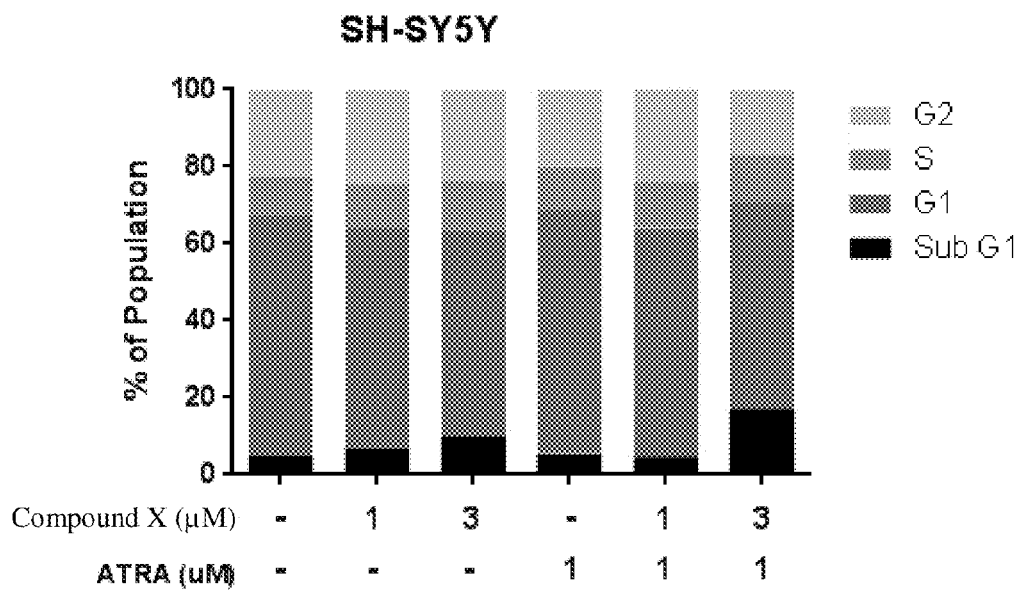
Figure 18C:
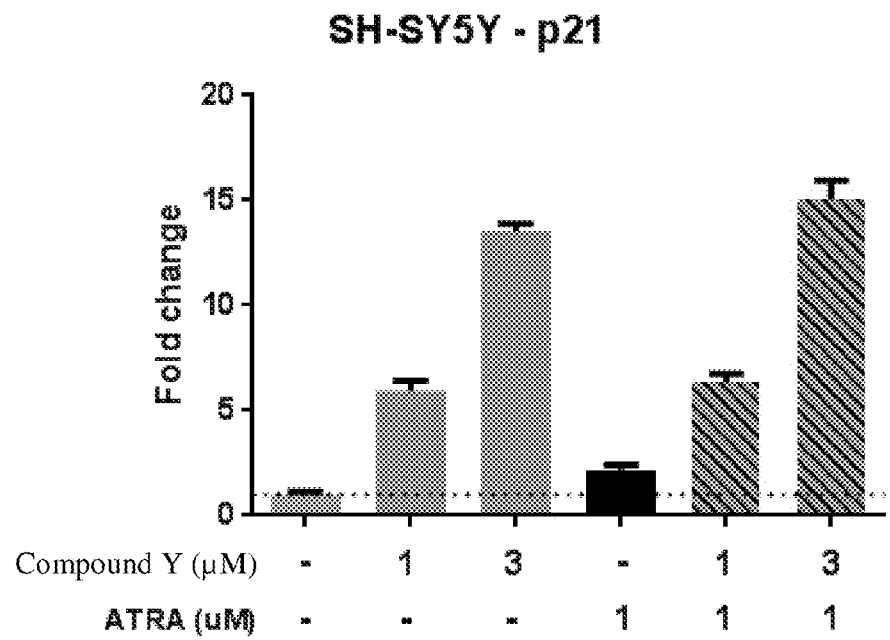
Figure 18D:
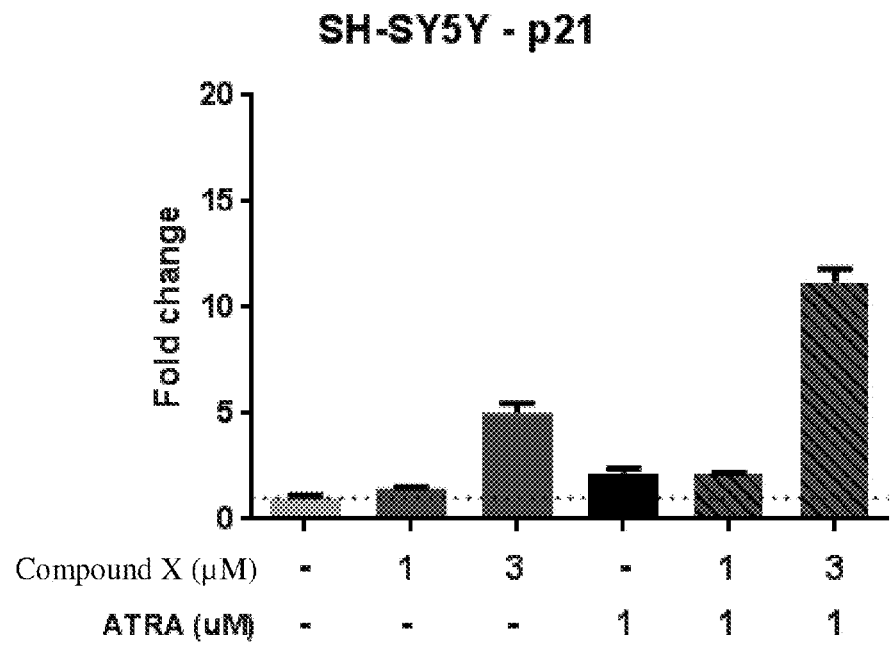

SK-N-BE(2) or SH-SY5Y neuroblastoma cells were treated with varying concentrations of either Compound X or Y, and/or ATRA (all trans retinoic acid). The differentiation index was measured. As a control, SK-N-BE(2) or SH-SY5Y neuroblastoma cells were treated with varying concentrations of ATRA. See FIGS. 16A-C. The results of these experiments show that ATRA differentiation was sub-optimal at 0.25 μM, and both Compound X and Compound Y potentiated 0.25 μM ATRA.

Example 43

HDAC Inhibition Induce Cell Cycle Arrest in Neuroblastoma Cells

SK-N-BE(2) neuroblastoma cells were treated with varying concentrations of either Compound X or Y, and/or ATRA (all trans retinoic acid). The percentage of the population of the cells at various stages of the cell cycle were measured after 4 days. In addition, the fold change of p21 was also calculated. See FIGS. 17A-D. Both Compound X and Compound Y induced cell cycle arrest, with Compound Y being the more potent agent. The HDACi/ATRA combination effects were modest, with little difference compared to single agents.

Example 44

HDAC Inhibition Induce Cell Cycle Arrest in Neuroblastoma Cells

SH-SY5Y neuroblastoma cells were treated with varying concentrations of either Compound X or Y, and/or ATRA (all trans retinoic acid). The percentage of the population of the cells at various stages of the cell cycle were measured after 4 days. In addition, the fold change of p21 was also calculated. See FIGS. 18A-D. Both Compound X and Compound Y induced cell cycle arrest, with Compound Y being the more potent agent. The HDACi/ATRA combination effects were modest, with little difference compared to single agents.

Example 45

Synthesis of 2-(diphenylamino)-N-(7-(hydroxyamino)-7-oxoheptyl) pyrimidine-5-carboxamide (Compound A)

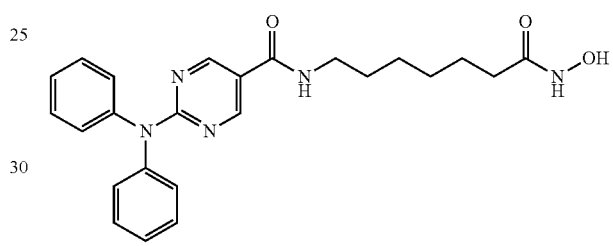

Reaction Scheme

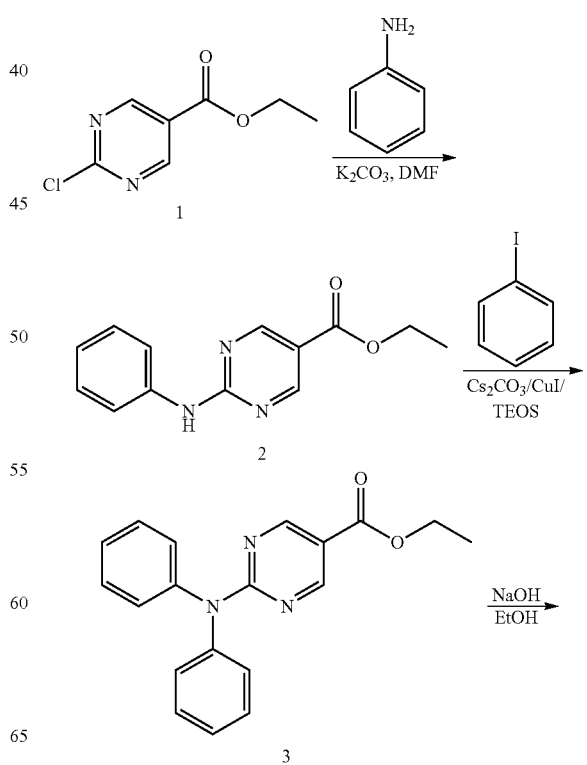

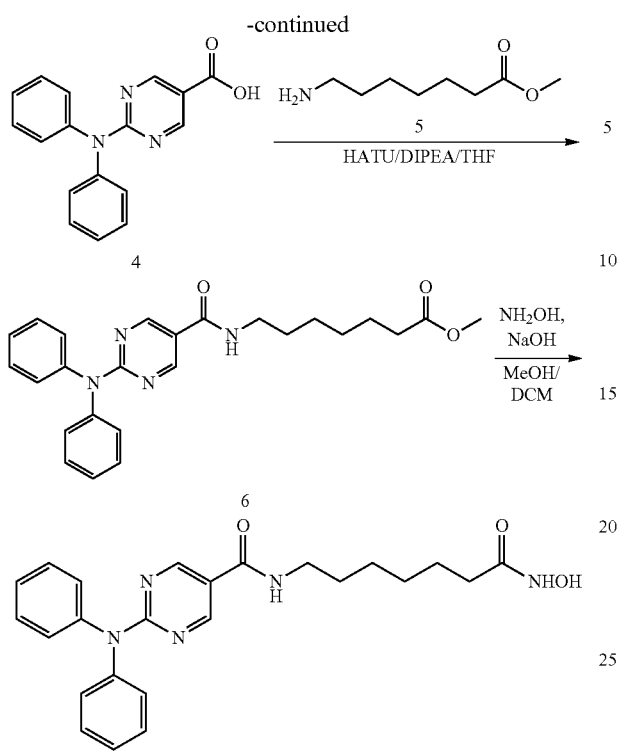

Synthesis of Intermediate 2:

A mixture of aniline (3.7 g, 40 mmol), compound 1 (7.5 g, 40 mmol), and K₂CO₃ (11 g, 80 mmol) in DMF (100 ml) was degassed and stirred at 120° C. under N₂ overnight. The reaction mixture was cooled to r.t. and diluted with EtOAc (200 ml), then washed with saturated brine (200 ml×3). The organic layers were separated and dried over Na₂SO₄, evaporated to dryness and purified by silica gel chromatography (petroleum ethers/EtOAc=10/1) to give the desired product as a white solid (6.2 g, 64%).

Synthesis of Intermediate 3:

A mixture of compound 2 (6.2 g, 25 mmol), iodobenzene (6.12 g, 30 mmol), CuI (955 mg, 5.0 mmol), Cs₂CO₃ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and NH₄F—H₂O on silica gel [50 g, pre-prepared by the addition of NH₄F (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4:

2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over Na₂SO₄. Removal of the solvent gave a brown solid (2.5 g, 92%).

Synthesis of Intermediate 6:

A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide (Compound A)

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 46

Synthesis of 2-((2-chlorophenyl)(phenyl)amino)-N-(7-(hydroxyamino)-7-oxoheptyl)pyrimidine-5-carboxamide (Compound Y)

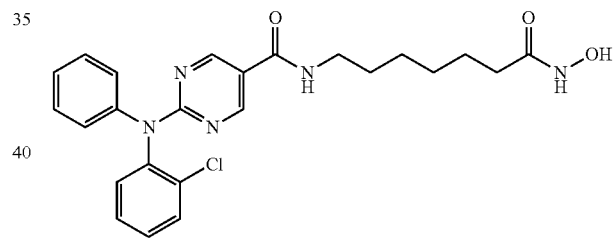

Reaction Scheme:

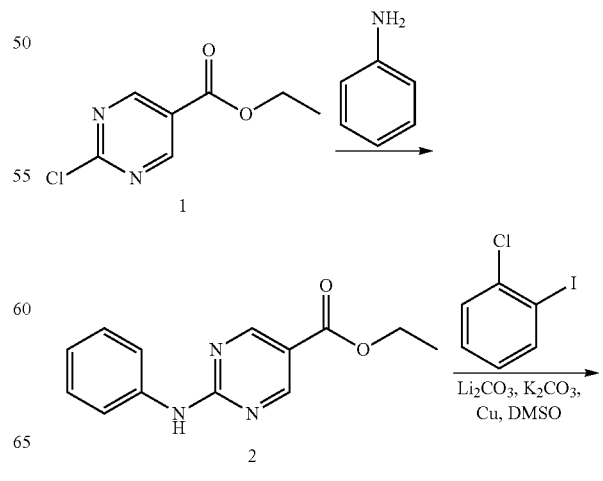

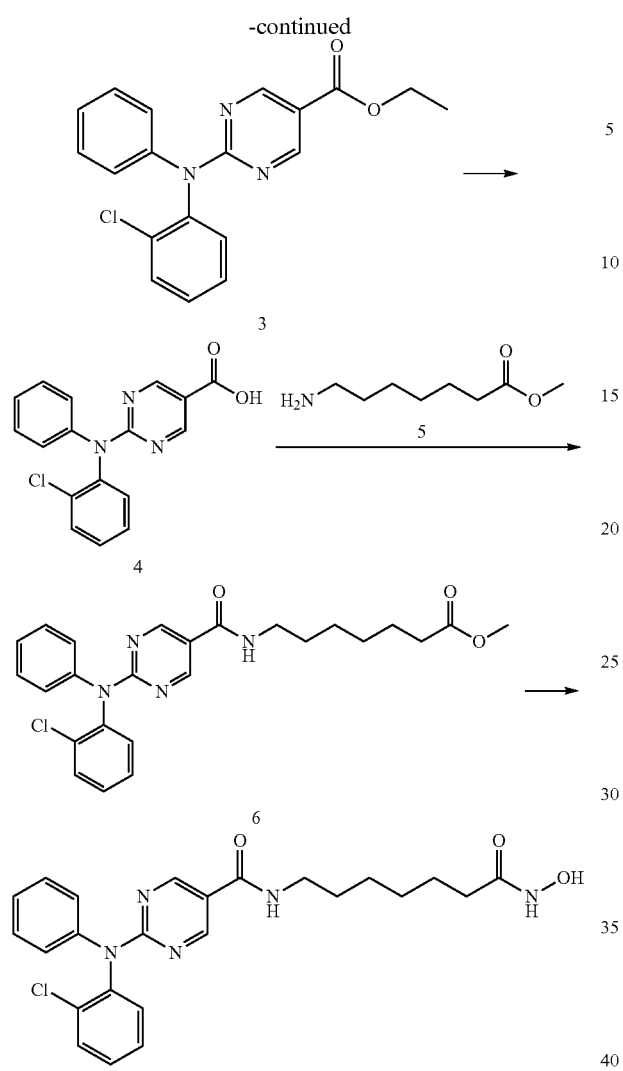

Synthesis of Intermediate 2:
See synthesis of intermediate 2 in Example 45.
Synthesis of Intermediate 3:
A mixture of compound 2 (69.2 g, 1 equiv.), 1-chloro-2-iodobenzene (135.7 g, 2 equiv.), $Li_2CO_3$ (42.04 g, 2 equiv.), $K_2CO_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.
Synthesis of Intermediate 4:
See synthesis of intermediate 4 in Example 45.
Synthesis of Intermediate 6: See synthesis of intermediate 6 in Example 45.

Synthesis of 2-((2-chlorophenyl)(phenyl)amino)-N-(7-(hydroxyamino)-7-oxoheptyl)pyrimidine-5-carboxamide (Compound B)

See synthesis of Compound A in Example 45.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:
1. A compound of Formula I:

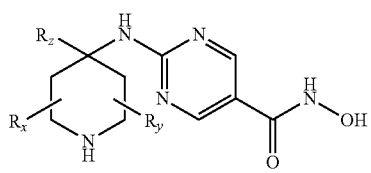

or a pharmaceutically acceptable salt thereof,
wherein,
$R_x$ is selected from the group consisting of $C_{1-6}$-alkyl, $C_{1-6}$-alkoxy, halo, —OH, —C(O)$R^1$, —CO$_2R^1$, —C(O)N($R^1$)$_2$, aryl, —C(S)N($R^1$)$_2$, and S(O)$_2R^1$, wherein aryl may be optionally substituted by one or more groups selected from $C_{1-6}$-alkyl, $C_{1-6}$-alkoxy, —OH, halo, and haloalkyl;
$R_y$ is selected from the group consisting of H, $C_{1-6}$-alkyl, $C_{1-6}$-alkoxy, halo, —OH, —C(O)$R^1$, —CO$_2R^1$, and —C(O)N($R^1$)$_2$;
$R_z$ is selected from the group consisting of $C_{1-6}$-alkyl, $C_{1-6}$-alkenyl, $C_{1-6}$-alkynyl, $C_{3-8}$-cycloalkyl, $C_{3-7}$-heterocycloalkyl, aryl, and heteroaryl, each of which may be optionally substituted by $C_{1-6}$-alkyl, $C_{1-6}$-alkoxy, halo, or —OH; and
each $R^1$ is, independently for each occurrence, selected from the group consisting of H, $C_{1-6}$-alkyl, $C_{3-8}$-cycloalkyl, $C_{3-7}$-heterocycloalkyl, aryl, heteroaryl, $C_{1-6}$-alkyl-cycloalkyl, $C_{1-6}$-alkyl-heterocycloalkyl, $C_{1-6}$-alkyl-aryl, and $C_{1-6}$-alkyl-heteroaryl, wherein $C_{3-8}$-cycloalkyl, $C_{3-7}$-heterocycloalkyl, aryl, heteroaryl, $C_{1-6}$-alkyl-cycloalkyl, $C_{1-6}$-alkyl-heterocycloalkyl, $C_{1-6}$-alkyl-aryl, and $C_{1-6}$-alkyl-heteroaryl may be optionally substituted by one or more groups selected from $C_{1-6}$-alkyl, $C_{1-6}$-alkoxy, —OH, halo, and haloalkyl.

2. The compound of claim 1, having the structure of Formula II:

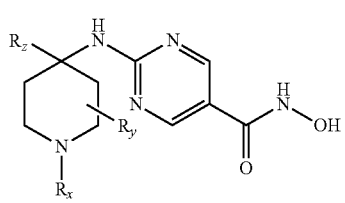

or a pharmaceutically acceptable salt thereof,
wherein,
$R_x$ is independently selected from the group consisting of aryl, —C(O)$R^1$, —CO$_2R^1$, —C(O)N($R^1$)$_2$, —C(S)N($R^1$)$_2$, and S(O)$_2R^1$;

$R_y$ is selected from the group consisting of H, $C_{1-6}$-alkyl, or, halo; and $R_z$ is selected from the group consisting of $C_{1-6}$-alkyl, $C_{3-8}$-cycloalkyl, $C_{3-7}$-heterocycloalkyl, aryl, and heteroaryl.

3. The compound of any one of claims 1-2, wherein $R_z$ is $C_{1-6}$-alkyl or aryl.

4. The compound of any one of claims 1-3, wherein $R_z$ is isopropyl or methyl.

5. The compound of any one of claims 1-3, wherein $R_z$ is phenyl.

6. The compound of any of claims 1-5, wherein $R_x$ is —C(O)NHR$^1$.

7. The compound of any of claims 1-5, wherein $R_x$ is —C(O)R$^1$ or —CO$_2$R$^1$.

8. The compound of any of claims 1-5, wherein $R_x$ is —C(S)NHR$^1$ or S(O)$_2$R$^1$.

9. The compound of any one of claims 1-8, wherein at least one of R$^1$ is selected from the group consisting of $C_{1-6}$-alkyl, aryl, $C_{1-6}$-alkyl-aryl and $C_{1-6}$-alkyl-heteroaryl, wherein aryl, $C_{1-6}$-alkyl-aryl and $C_{1-6}$-alkyl-heteroaryl may be optionally substituted by one or more groups selected from $C_{1-6}$-alkyl, $C_{1-6}$-alkoxy, —OH, halo, and haloalkyl.

10. The compound of any one of claims 1-8, wherein at least one of R$^1$ is —CH$_3$, —CH$_2$CH$_3$, phenyl, —CH$_2$-phenyl, or —CH$_2$-indolyl, wherein phenyl, —CH$_2$-phenyl, or —CH$_2$-indolyl may be optionally substituted by one or more groups selected from $C_{1-6}$-alkyl or halo.

11. The compound of any one of claims 1-8, wherein at least one of R$^1$ is phenyl, and wherein phenyl is optionally substituted by one or more groups selected from $C_{1-6}$-alkyl, $C_{1-6}$-alkoxy, halo, and haloalkyl.

12. The compound of claim any one of claims 1-11, wherein $R_y$ is H.

13. The compound of any one of claims 1-12, selected from the following:

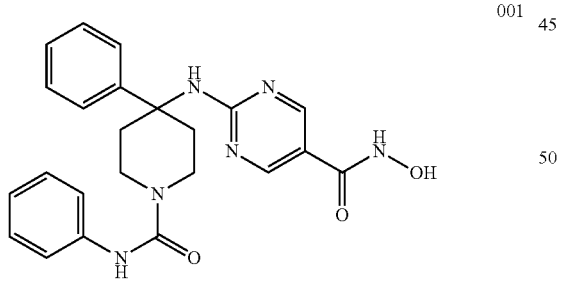

001

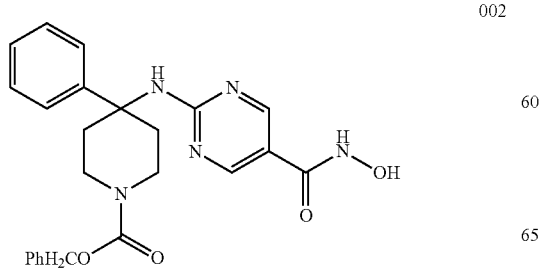

002

-continued

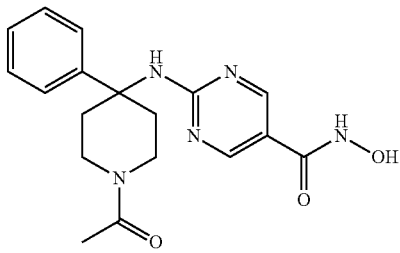

003

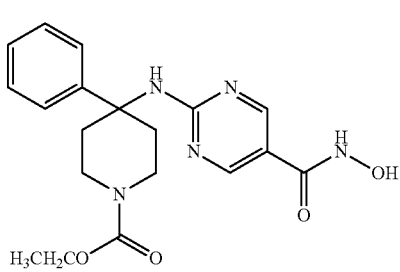

004

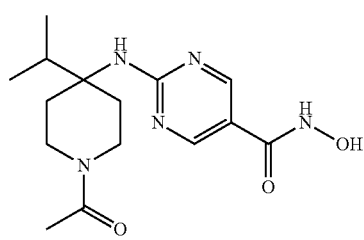

005

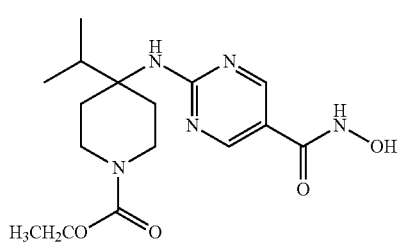

006

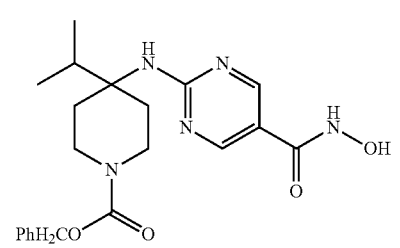

007

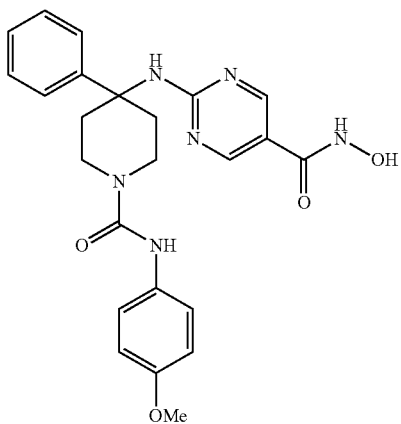
008
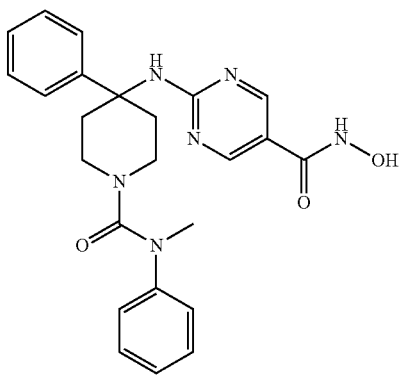
012
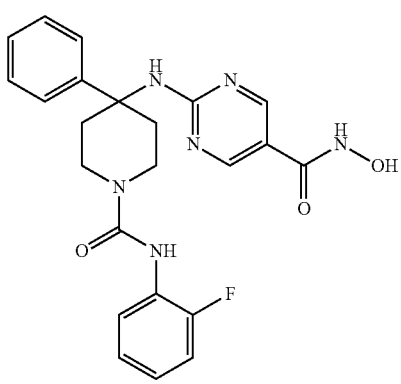
009
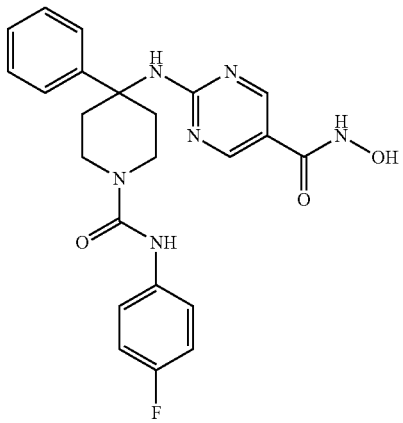
013
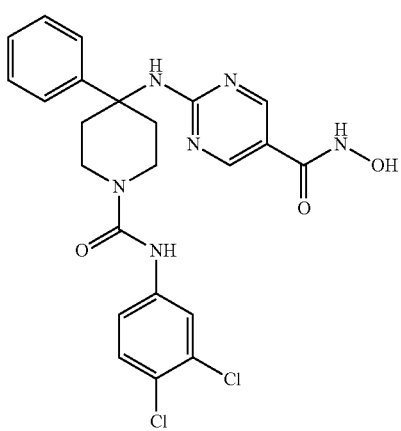
010
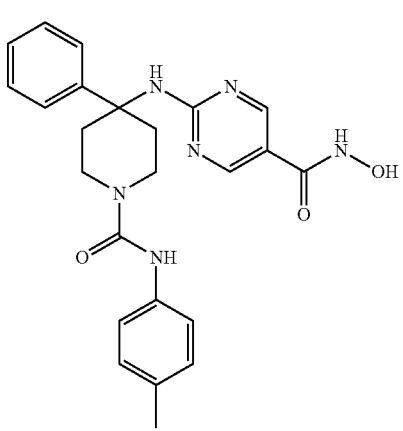
014
011
015

016
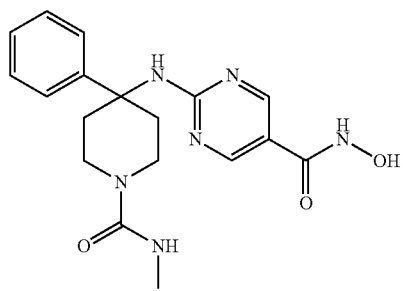
017
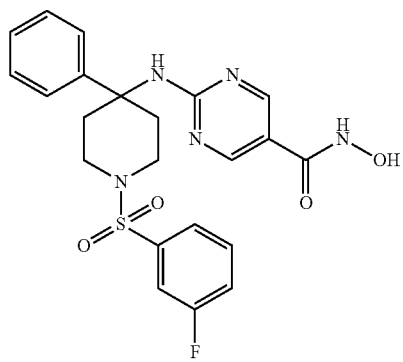
018
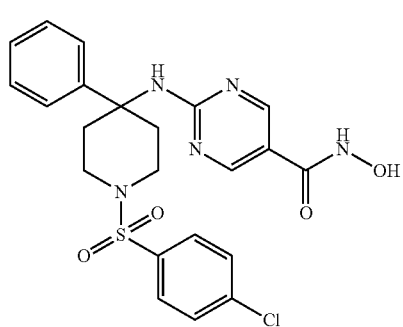
019
020
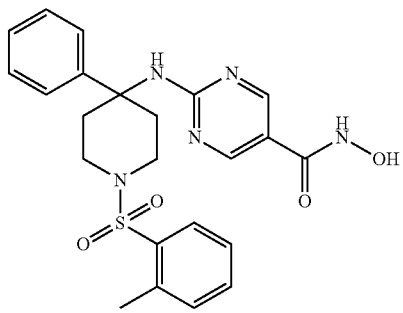
021
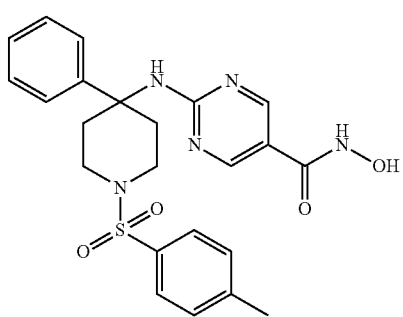
022
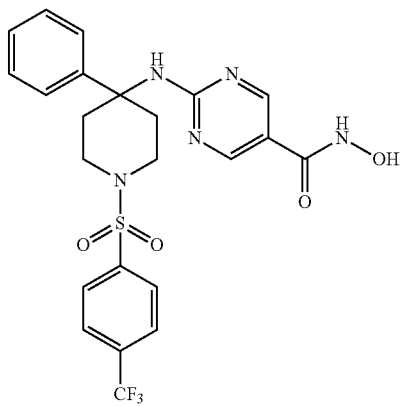
023
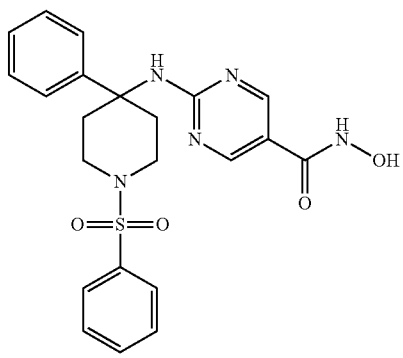

024
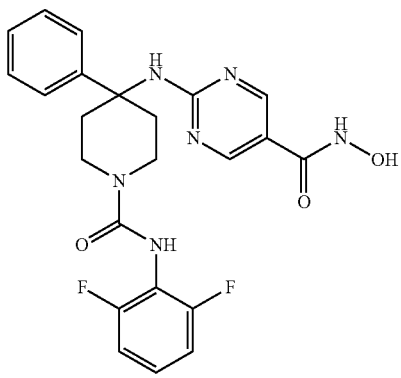
025
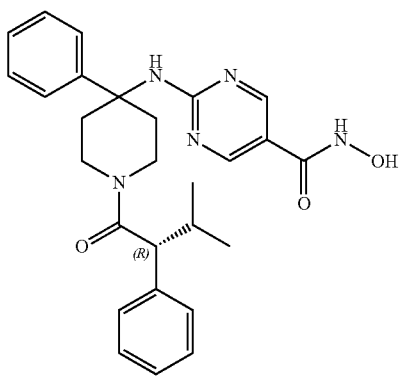
026
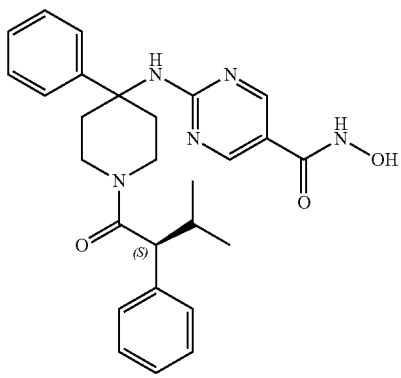
027
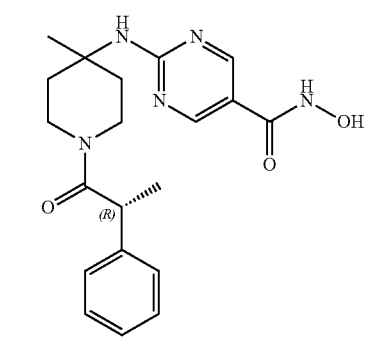
028
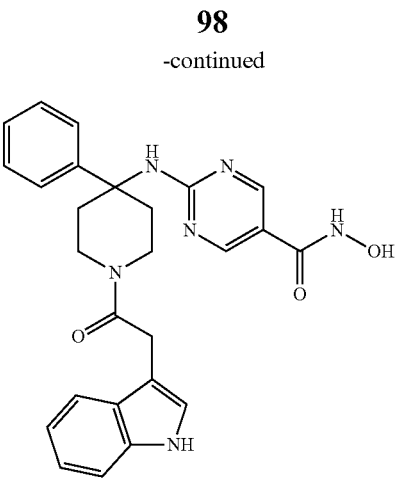
029
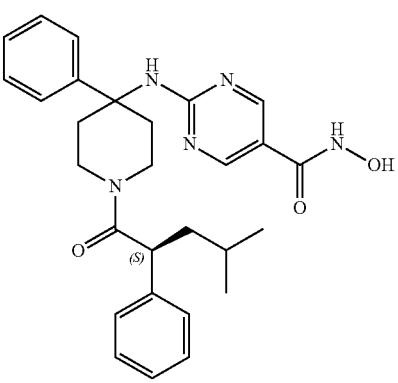
030
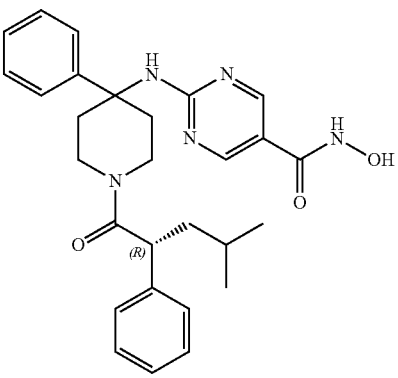
031
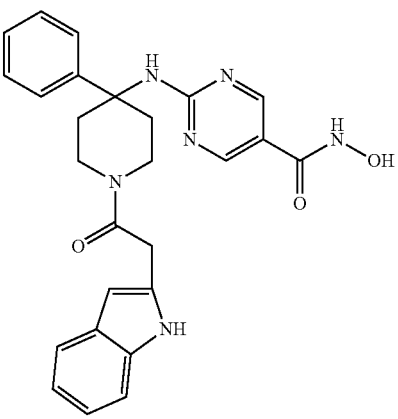
or pharmaceutically acceptable salts thereof.

14. A pharmaceutical composition comprising a compound of any one of claims 1-13, or a pharmaceutically acceptable salt thereof, together with a pharmaceutically acceptable carrier.

15. A method of treating hemoglobinopathy in a human subject in need thereof comprising administering to the subject a compound of any one of claims 1-13, or a pharmaceutically acceptable salt thereof, or the pharmaceutical composition of claim 14.

16. A method of treating sickle-cell disease in a human subject in need thereof comprising administering to the subject a compound of any one of claims 1-13, or a pharmaceutically acceptable salt thereof, or the pharmaceutical composition of claim 14.

17. A method of treating beta-thalassemia in a human subject in need thereof comprising administering to the subject a compound of any one of claims 1-13, or a pharmaceutically acceptable salt thereof, or the pharmaceutical composition of claim 14.

18. A method of treating a neurodegenerative disease selected from the group consisting of Alzheimer's disease, frontotemporal lobe dementia, progressive supranuclear palsy, corticobasal dementia, Parkinson's disease, Huntington's disease, amytrophic lateral sclerosis, Charcot-Marie-Tooth disease and peripheral neuropathy in a human subject in need thereof comprising administering to the subject a compound of any one of claims 1-13, or a pharmaceutically acceptable salt thereof, or the pharmaceutical composition of claim 14.

19. A method of treating cancer in a human subject in need thereof comprising administering to the subject a compound of any one of claims 1-13, or a pharmaceutically acceptable salt thereof, or the pharmaceutical composition of claim 14.

20. The method of claim 19, wherein the cancer is selected from the group consisting of lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors.

21. The method of claim 19, wherein the cancer is lung cancer, colon cancer, breast cancer, leukemia, or a lymphoma.

22. The method of claim 19, wherein the cancer is neuroblastoma.

23. The method of claim 19, wherein the cancer is non-small cell lung cancer (NSCLC).

24. A method of treating a human subject suffering from Hodgkin's lymphoma comprising administering to the subject a therapeutically effective amount of a compound of any one of claims 1-13, or a pharmaceutically acceptable salt thereof, or the pharmaceutical composition of claim 14, to thereby treat the subject suffering from Hodgkin's lymphoma.

* * * * *